US011402372B2

(12) United States Patent
Matyskiela et al.

(10) Patent No.: US 11,402,372 B2
(45) Date of Patent: Aug. 2, 2022

(54) METHODS FOR SCREENING CEREBLON MODIFYING COMPOUNDS

(71) Applicant: CELGENE CORPORATION, Summit, NJ (US)

(72) Inventors: Mary Matyskiela, San Diego, CA (US); Philip Chamberlain, San Diego, CA (US); Suzana Sturlini Couto, La Jolla, CA (US); Katherine Stamp, Montclair, NJ (US); Philip J. Sherratt, Scotch Plains, NJ (US); Gang Lu, San Diego, CA (US); Julia Hui, Basking Ridge, NJ (US)

(73) Assignee: CELGENE CORPORATION, Summit, NJ (US)

( * ) Notice: Subject to any disclaimer, the term of this patent is extended or adjusted under 35 U.S.C. 154(b) by 326 days.

(21) Appl. No.: 16/244,667

(22) Filed: Jan. 10, 2019

(65) Prior Publication Data

US 2019/0219562 A1    Jul. 18, 2019

Related U.S. Application Data

(60) Provisional application No. 62/710,401, filed on Feb. 16, 2018, provisional application No. 62/617,112, filed on Jan. 12, 2018.

(51) Int. Cl.
*G01N 33/50* (2006.01)
*G01N 33/68* (2006.01)

(52) U.S. Cl.
CPC ....... *G01N 33/502* (2013.01); *G01N 33/5014* (2013.01); *G01N 33/5017* (2013.01); *G01N 33/6872* (2013.01); *G01N 2333/46* (2013.01); *G01N 2800/385* (2013.01)

(58) Field of Classification Search
CPC ............. G01N 33/502; G01N 33/5014; G01N 33/5017; G01N 33/6872; G01N 2333/46; G01N 2800/385
See application file for complete search history.

(56) References Cited

U.S. PATENT DOCUMENTS

| 2004/0265230 | A1 | 12/2004 | Martinez et al. |
| 2008/0241110 | A1 | 10/2008 | Ma |
| 2020/0348285 | A1* | 11/2020 | Fischer ............... C07K 14/4702 |

FOREIGN PATENT DOCUMENTS

| WO | WO 2017161119 A1 | 9/2017 |
| WO | WO 2019094718 A1 | 5/2019 |

OTHER PUBLICATIONS

International Search Report and Written Opinion of corresponding Interantional Patent Application No. PCT/US2019/013049 dated May 23, 2019 (20 pages).

Knobloch et al., 2008, "Shedding light on an old mystery", Cell Cycle, 7(9): 1121-1127.
An et al., 2017, "pSILAC mass spectrometry reveals ZFP91 as IMiD-dependent substrate of the CRL4 CRBN ubiquitin ligase", Nat Commun., 8:15398 (11 pages).
Chamberlain et al., 2014, "Structure of the human Cereblon-DDB1-lenalidomide complex reveals basis for responsiveness to thalidomide analogs", Nat Struct Mol Biol., 21(9):803-809.
Donovan et al., 2018, "Thalidomide promotes degradation of SALL4, a transcription factor implicated in Duane Radial Ray syndrome", Elife, 7:e38430 (25 pages).
Emsley et al., 2010, "Features and development of Coot", Acta Crystallogr D Biol Crystallogr, 66(Pt4):486-501.
Fratta et al., 1965, "Teratogenic Effects of Thalidomide in Rabbits, Rats, Hamsters, and Mice", Toxicol Appl Pharmacol., 7:268-286.
Gandhi et al., 2014, "Immunomodulatory agents lenalidomide and pomalidomide co-stimulate T cells by inducing degradation of T cell repressors Ikaros and Aiolos via modulation of the E3 ubiquitin ligase complex CRL4(CRBN,)", Br J Haematol., 164(6):811-821 (Epub 2013),.
Hagner et al., 2015, "CC-122, a pleiotropic pathway modifier, mimics an interferon response and has antitumor activity in DLBCL", Blood, 126(6):779-789.
Harder et al., 2016, "OPLS3: A Force Field Providing Broad Coverage of Drug-like Small Molecules and Proteins", J Chem Theory Comput., 12(1):281-296 (Epub 2015).
Humphrey et al., 1996, "VMD: visual molecular dynamics", J Mol Graph, 14(1):33-38.
Kohlhase et al., 2003, "Mutations at the SALL4 locus on chromosome 20 result in a range of clinically overlapping phenotypes, including Okihiro syndrome, Holt-Oram syndrome, acro-renal-ocular syndrome, and patients previously reported to represent thalidomide embryopathy" J Med Genet, 40(7):473-478.
Kohlhase et al., 2004, "Mutations in SALL4 in malformed father and daughter postulated previously due to reflect mutagenesis by thalidomide", Birth Defects Res A Clin Mol Teratol, 70(8):550-551.
Kronke et al., 2014, "Lenalidomide causes selective degradation of IKZF1 and IKZF3 in multiple myeloma cells", Science, 343(6168):301-305 (Epub 2013).
Kronke et al., 2015, "Lenalidomide induces ubiquitination and degradation of CK1α in del(5q) MDS", Nature, 523(7559): 183-188 and supplemental materials (20 pages).

(Continued)

*Primary Examiner* — Shafiqul Haq
(74) *Attorney, Agent, or Firm* — Jones Day

(57) ABSTRACT

A method of screening a cereblon modifying compound for treating a disease or disorder, comprising: obtaining a sample; determining a first protein level of SALL4; administering the cereblon modifying compound to the sample; determining a second protein level of SALL4; comparing the first level and the second protein level of SALL4 to determine if the cereblon modifying compound induces degradation of SALL4; and selecting the cereblon modifying compound that does not induce degradation of SALL4.

2 Claims, 20 Drawing Sheets
Specification includes a Sequence Listing.

(56) References Cited

OTHER PUBLICATIONS

Lu et al., 2014, "The myeloma drug lenalidomide promotes the cereblon-dependent destruction of Ikaros proteins", Science, 343(6168):305-309 (Epub 2013).
Lu et al., 2015, "Hijacking the E3 Ubiquitin Ligase Cereblon to Efficiently Target BRD4", Chem Biol., 22(6):755-763.
Matysktfla et al., 2016, "A novel cereblon modulator recruits GSPT1 to the CRL4(CRBN) ubiquitin ligase", Nature, 535(7611):252-257 and supplemental materials (24 pages).
Matyskiela et al., 2018, "A Cereblon Modulator (CC-220) with Improved Degradation of Ikaros and Aiolos", J Med Chem., 61(2):535-542 (Epub 2017).
Matyskiela et al., 2018, "SALL4 mediates teratogenicity as a thalidomide-dependent cereblon substrate", Nat Chem Biol., 14(10):981-987 and supplemental materials (12 pages).
McCoy et al., 2007, "Phaser crystallographic software", J Appl Crystallogr., 40(Pt 4):658-674.
Murshudov et al., 2011, "REFMAC5 for the refinement of macromolecular crystal structures", Acta Crystallogr D Biol Crystallogr., 67(Pt 4) :355-367.
Petzold et al., 2016, "Structural basis of lenalidomide-induced CK1α degradation by the CRL4(CRBN) ubiquitin ligase", Nature, 532(7597): 127-130 and supplemental materials (16 pages).
Schafer et al., 2018, "Cereblon modulator iberdomide induces degradation of the transcription factors Ikaros and Aiolos: immunomodulation in healthy volunteers and relevance to systemic lupus erythematosus", Ann Rheum Dis., 77(10):1516-1523,.
Sievers et al., 2018, "Defining the human C2H2 zinc finger degrome targeted by thalidomide analogs through CRBN", Science, 362(6414):eaat0572 (11 pages).
Vargesson, 2019, "The teratogenic effects of thalidomide on limbs", J Hand Surg Eur vol. 44(l):88-95 (Epub 2018).
Winter et al., 2015, "Drug Development. Phthalimide conjugation as a strategy for in vivo target protein degradation", Science, 348(6241):1376-1381.

* cited by examiner

| | | |
|---|---|---|
| Ikaros(a.a.145-167) | FQCNQCGASFTQKGNLLRHIKLH | SEQ ID NO: 8 |
| ZFP91(a.a.400-422) | LQCEICGFTCRQRASLNWHMKKH | SEQ ID NO: 9 |
| Sall4-ZF1 | HKCKYCSKVFGTDSSLQIHLRSH | SEQ ID NO: 10 |
| Sall4-ZF2 | FVCSVCCHRFTTKGNLKVHFHRH | SEQ ID NO: 11 |
| Sall4-ZF3 | NECLICHRVLSCQSSLKMHYRTH | SEQ ID NO: 12 |
| Sall4-ZF4 | FQCKICGRAFSTKGNLKTHLGVH | SEQ ID NO: 14 |
| Sall4-ZF5 | HSCPICQKKFTNAVMLQQHIRMH | SEQ ID NO: 15 |
| Sall4-ZF6 | HGCTRCGKNFSSASALQIHERTH | SEQ ID NO: 16 |
| Sall4-ZF7 | FVCNICGRAFTTKGNLKVHYMTH | SEQ ID NO: 17 |

FIG. 1B

Alignment of Human Cereblon (SEQ ID NO: 18), Rabbit Cereblon (SEQ ID NO: 19) and Mouse Cereblon (SEQ ID NO: 20)

FIG. 1E

Alignment of Human SALL4A (SEQ ID NO: 21), Rabbit SALL4A (SEQ ID NO: 22) and Mouse SALL4A (SEQ ID NO: 23)

SEQUENCE LISTING

```
<160> NUMBER OF SEQ ID NOS: 23

<210> SEQ ID NO 1
<211> LENGTH: 1053
<212> TYPE: PRT
<213> ORGANISM: Artificial Sequence
<220> FEATURE:
<223> OTHER INFORMATION: amino acid sequences of human SALL4A

<400> SEQUENCE: 1

Met Ser Arg Arg Lys Gln Ala Lys Pro Gln His Ile Asn Ser Glu Glu
1               5                   10                  15

Asp Gln Gly Glu Gln Gln Pro Gln Gln Thr Pro Glu Phe Ala Asp
            20                  25                  30

Ala Ala Pro Ala Ala Pro Ala Ala Gly Glu Leu Gly Ala Pro Val Asn
        35                  40                  45

His Pro Gly Asn Asp Glu Val Ala Ser Glu Asp Glu Ala Thr Val Lys
    50                  55                  60

Arg Leu Arg Arg Glu Glu Thr His Val Cys Glu Lys Cys Cys Ala Glu
65                  70                  75                  80

Phe Phe Ser Ile Ser Glu Phe Leu Glu His Lys Lys Asn Cys Thr Lys
                85                  90                  95
```

```
Asn Pro Pro Val Leu Ile Met Asn Asp Ser Glu Gly Pro Val Pro Ser
                100                 105                 110

Glu Asp Phe Ser Gly Ala Val Leu Ser His Gln Pro Thr Ser Pro Gly
            115                 120                 125

Ser Lys Asp Cys His Arg Glu Asn Gly Gly Ser Ser Glu Asp Met Lys
        130                 135                 140

Glu Lys Pro Asp Ala Glu Ser Val Val Tyr Leu Lys Thr Glu Thr Ala
145                 150                 155                 160

Leu Pro Pro Thr Pro Gln Asp Ile Ser Tyr Leu Ala Lys Gly Lys Val
                165                 170                 175

Ala Asn Thr Asn Val Thr Leu Gln Ala Leu Arg Gly Thr Lys Val Ala
            180                 185                 190

Val Asn Gln Arg Ser Ala Asp Ala Leu Pro Ala Pro Val Pro Gly Ala
        195                 200                 205

Asn Ser Ile Pro Trp Val Leu Glu Gln Ile Leu Cys Leu Gln Gln Gln
210                 215                 220

Gln Leu Gln Gln Ile Gln Leu Thr Glu Gln Ile Arg Ile Gln Val Asn
225                 230                 235                 240

Met Trp Ala Ser His Ala Leu His Ser Ser Gly Ala Gly Ala Asp Thr
                245                 250                 255

Leu Lys Thr Leu Gly Ser His Met Ser Gln Gln Val Ser Ala Ala Val
            260                 265                 270

Ala Leu Leu Ser Gln Lys Ala Gly Ser Gln Gly Leu Ser Leu Asp Ala
        275                 280                 285

Leu Lys Gln Ala Lys Leu Pro His Ala Asn Ile Pro Ser Ala Thr Ser
290                 295                 300

Ser Leu Ser Pro Gly Leu Ala Pro Phe Thr Leu Lys Pro Asp Gly Thr
305                 310                 315                 320

Arg Val Leu Pro Asn Val Met Ser Arg Leu Pro Ser Ala Leu Leu Pro
                325                 330                 335

Gln Ala Pro Gly Ser Val Leu Phe Gln Ser Pro Phe Ser Thr Val Ala
            340                 345                 350

Leu Asp Thr Ser Lys Lys Gly Lys Gly Lys Pro Pro Asn Ile Ser Ala
        355                 360                 365

Val Asp Val Lys Pro Lys Asp Glu Ala Ala Leu Tyr Lys His Lys Cys
370                 375                 380

Lys Tyr Cys Ser Lys Val Phe Gly Thr Asp Ser Ser Leu Gln Ile His
385                 390                 395                 400

Leu Arg Ser His Thr Gly Glu Arg Pro Phe Val Cys Ser Val Cys Gly
                405                 410                 415

His Arg Phe Thr Thr Lys Gly Asn Leu Lys Val His Phe His Arg His
            420                 425                 430

Pro Gln Val Lys Ala Asn Pro Gln Leu Phe Ala Glu Phe Gln Asp Lys
        435                 440                 445

Val Ala Ala Gly Asn Gly Ile Pro Tyr Ala Leu Ser Val Pro Asp Pro
450                 455                 460

Ile Asp Glu Pro Ser Leu Ser Leu Asp Ser Lys Pro Val Leu Val Thr
465                 470                 475                 480

Thr Ser Val Gly Leu Pro Gln Asn Leu Ser Ser Gly Thr Asn Pro Lys
                485                 490                 495

Asp Leu Thr Gly Gly Ser Leu Pro Gly Asp Leu Gln Pro Gly Pro Ser
            500                 505                 510

Pro Glu Ser Glu Gly Gly Pro Thr Leu Pro Gly Val Gly Pro Asn Tyr
```

```
            515                 520                 525
Asn Ser Pro Arg Ala Gly Gly Phe Gln Gly Ser Gly Thr Pro Glu Pro
    530                 535                 540

Gly Ser Glu Thr Leu Lys Leu Gln Gln Leu Val Glu Asn Ile Asp Lys
545                 550                 555                 560

Ala Thr Thr Asp Pro Asn Glu Cys Leu Ile Cys His Arg Val Leu Ser
                565                 570                 575

Cys Gln Ser Ser Leu Lys Met His Tyr Arg Thr His Thr Gly Glu Arg
            580                 585                 590

Pro Phe Gln Cys Lys Ile Cys Gly Arg Ala Phe Ser Thr Lys Gly Asn
        595                 600                 605

Leu Lys Thr His Leu Gly Val His Arg Thr Asn Thr Ser Ile Lys Thr
    610                 615                 620

Gln His Ser Cys Pro Ile Cys Gln Lys Lys Phe Thr Asn Ala Val Met
625                 630                 635                 640

Leu Gln Gln His Ile Arg Met His Met Gly Gly Gln Ile Pro Asn Thr
                645                 650                 655

Pro Leu Pro Glu Asn Pro Cys Asp Phe Thr Gly Ser Glu Pro Met Thr
            660                 665                 670

Val Gly Glu Asn Gly Ser Thr Gly Ala Ile Cys His Asp Val Ile
        675                 680                 685

Glu Ser Ile Asp Val Glu Val Ser Ser Gln Glu Ala Pro Ser Ser
    690                 695                 700

Ser Ser Lys Val Pro Thr Pro Leu Pro Ser Ile His Ser Ala Ser Pro
705                 710                 715                 720

Thr Leu Gly Phe Ala Met Met Ala Ser Leu Asp Ala Pro Gly Lys Val
                725                 730                 735

Gly Pro Ala Pro Phe Asn Leu Gln Arg Gln Gly Ser Arg Glu Asn Gly
            740                 745                 750

Ser Val Glu Ser Asp Gly Leu Thr Asn Asp Ser Ser Ser Leu Met Gly
        755                 760                 765

Asp Gln Glu Tyr Gln Ser Arg Ser Pro Asp Ile Leu Glu Thr Thr Ser
    770                 775                 780

Phe Gln Ala Leu Ser Pro Ala Asn Ser Gln Ala Glu Ser Ile Lys Ser
785                 790                 795                 800

Lys Ser Pro Asp Ala Gly Ser Lys Ala Glu Ser Ser Glu Asn Ser Arg
                805                 810                 815

Thr Glu Met Glu Gly Arg Ser Ser Leu Pro Ser Thr Phe Ile Arg Ala
            820                 825                 830

Pro Pro Thr Tyr Val Lys Val Glu Val Pro Gly Thr Phe Val Gly Pro
        835                 840                 845

Ser Thr Leu Ser Pro Gly Met Thr Pro Leu Leu Ala Ala Gln Pro Arg
    850                 855                 860

Arg Gln Ala Lys Gln His Gly Cys Thr Arg Cys Gly Lys Asn Phe Ser
865                 870                 875                 880

Ser Ala Ser Ala Leu Gln Ile His Glu Arg Thr His Thr Gly Glu Lys
                885                 890                 895

Pro Phe Val Cys Asn Ile Cys Gly Arg Ala Phe Thr Thr Lys Gly Asn
            900                 905                 910

Leu Lys Val His Tyr Met Thr His Gly Ala Asn Asn Asn Ser Ala Arg
        915                 920                 925

Arg Gly Arg Lys Leu Ala Ile Glu Asn Thr Met Ala Leu Leu Gly Thr
    930                 935                 940
```

Asp Gly Lys Arg Val Ser Glu Ile Phe Pro Lys Glu Ile Leu Ala Pro
945                 950                 955                 960

Ser Val Asn Val Asp Pro Val Val Trp Asn Gln Tyr Thr Ser Met Leu
            965                 970                 975

Asn Gly Gly Leu Ala Val Lys Thr Asn Glu Ile Ser Val Ile Gln Ser
        980                 985                 990

Gly Gly Val Pro Thr Leu Pro Val  Ser Leu Gly Ala Thr  Ser Val Val
        995                 1000                1005

Asn Asn  Ala Thr Val Ser Lys  Met Asp Gly Ser Gln  Ser Gly Ile
    1010                1015                1020

Ser Ala  Asp Val Glu Lys Pro  Ser Ala Thr Asp Gly  Val Pro Lys
    1025                1030                1035

His Gln  Phe Pro His Phe Leu  Glu Glu Asn Lys Ile  Ala Val Ser
    1040                1045                1050

<210> SEQ ID NO 2
<211> LENGTH: 3162
<212> TYPE: DNA
<213> ORGANISM: Artificial Sequence
<220> FEATURE:
<223> OTHER INFORMATION: nucleic acid sequence of human SALL4A

<400> SEQUENCE: 2
atgtcgaggc gcaagcaggc gaaaccccag cacatcaact cggaggagga ccagggcgag      60
cagcagccgc agcagcagac cccggagttt gcagatgcgg ccccagcggc gcccgcggcg     120
ggggagctgg gtgctccagt gaaccaccca gggaatgacg aggtggcgag tgaggatgaa     180
gccacagtaa agcggcttcg tcgggaggag acgcacgtct gtgagaaatg ctgtgcggag     240
ttcttcagca tctctgagtt cctggaacat aagaaaaatt gcactaaaaa tccacctgtc     300
ctcatcatga atgacagcga ggggcctgtg ccttcagaag acttctccgg agctgtactg     360
agccaccagc ccaccagtcc cggcagtaag gactgtcaca gggagaatgg cggcagctca     420
gaggacatga aggagaagcc ggatgcggag tctgtggtgt acctaaagac agagacagcc     480
ctgccaccca ccccccagga cataagctat ttagccaaag caaagtggc caacactaat     540 gtgaccttgc aggcactacg gggcaccaag gtggcggtga atcagcggag cgcggatgca     600
ctccctgccc ccgtgcctgg tgccaacagc atcccgtggg cctcgagca gatcttgtgt     660 ctgcagcagc agcagctaca gcagatccag ctcaccgagc agatccgcat ccaggtgaac     720
atgtgggcct cccacgccct ccactcaagc ggggcagggg ccgacactct gaagaccttg     780
ggcagccaca tgtctcagca ggtttctgca gctgtggctt gctcagcca aaagctgga     840 agccaaggtc tgtctctgga tgccttgaaa caagccaagc tacctcacgc caacatccct     900
tctgccacca gctccctgtc cccagggctg gcacccttca ctctgaagcc ggatgggacc     960
cgggtgctcc cgaacgtcat gtcccgcctc ccgagcgctt gcttcctca ggccccgggc    1020 tcggtgctct tccagagccc tttctccact gtggcgctag acacatccaa gaaagggaag    1080
gggaagccac cgaacatctc cgcggtggat gtcaaaccca agacgaggc ggccctctac    1140 aagcacaagt gtaagtactg tagcaaggtt tttgggactg atagctcctt gcagatccac    1200
ctccgctccc acactggaga gagacccttc gtgtgctctc tctgtggtca tcgcttcacc    1260
accaagggca acctcaaggt gcactttcac cgacatcccc aggtgaaggc aaaccccag    1320 ctgtttgccg agttccagga caaagtggcg gccggcaatg catcccta tgcactctct    1380 gtacctgacc ccatagatga accgagtctt ttctttagaca gcaaacctgt ccttgtaacc    1440

-continued

```
acctctgtag ggctacctca gaatctttct tcggggacta atcccaagga cctcacgggt    1500
ggctccttgc ccggtgacct gcagcctggg ccttctccag aaagtgaggg tggacccaca    1560
ctccctgggg tgggaccaaa ctataattcc caagggctg gtggcttcca agggagtggg     1620
acccctgagc cagggtcaga gaccctgaaa ttgcagcagt tggtggagaa cattgacaag    1680
gccaccactg atcccaacga atgtctcatt tgccaccgag tcttaagctg tcagagctcc    1740
ctcaagatgc attatcgcac ccacaccggg gagagaccgt tccagtgtaa gatctgtggc    1800
cgagcctttt ctaccaaagg taacctgaag acacaccttg ggttcaccg aaccaacaca     1860 tccattaaga cgcagcattc gtgccccatc tgccagaaga agttcactaa tgccgtgatg    1920
ctgcagcaac atattcggat gcacatgggc ggtcagattc ccaacacgcc cctgccagag    1980
aatccctgtg actttacggg ttctgagcca atgaccgtgg gtgagaacgg cagcaccggc    2040
gctatctgcc atgatgatgt catcgaaagc atcgatgtag aggaagtcag ctcccaggag    2100
gctcccagca gctcctccaa ggtccccacg cctcttccca gcatccactc ggcatcaccc    2160
acgctagggt ttgccatgat ggcttcctta gatgccccag ggaaagtggg tcctgcccct    2220
tttaacctgc agcgccaggg cagcagaaa acggttccg tggagagcga tggcttgacc      2280
aacgactcat cctcgctgat gggagaccag gagtatcaga gccgaagccc agatatcctg    2340
gaaaccacat ccttccaggc actctccccg gccaatagtc aagccgaaag catcaagtca    2400
aagtctcccg atgctgggag caaagcagag agctccgaga acagccgcac tgagatggaa    2460
ggtcggagca gtctcccttc cacgtttatc cgagccccgc cgacctatgt caaggttgaa    2520
gttcctggca catttgtggg accctcgaca ttgtccccag ggatgacccc tttgttagca    2580
gcccagccac gccgacaggc caagcaacat ggctgcacac ggtgtgggaa gaacttctcg    2640
tctgctagcg ctcttcagat ccacgagcgg actcacactg gagagaagcc ttttgtgtgc    2700
aacatttgtg ggcgagcttt taccaccaaa ggcaacttaa aggttcacta catgacacac    2760
ggggcgaaca ataactcagc ccgccgtgga aggaagttgg ccatcgagaa caccatggct    2820
ctgttaggta cggacggaaa aagagtctca gaaatctttc caaggaaat cctggcccct     2880 tcagtgaatg tggaccctgt tgtgtggaac cagtacacca gcatgctcaa tggcggtctg    2940
gccgtgaaga ccaatgagat ctctgtgatc cagagtgggg gggttcctac cctcccggtt    3000
tccttggggg ccacctccgt tgtgaataac gccactgtct ccaagatgga tggctcccag    3060
tcgggtatca gtgcagatgt ggaaaaacca agtgcactg acggcgttcc caaacaccag    3120
tttcctcact tcctggaaga aaacaagatt gcggtcagct aa                       3162
```

<210> SEQ ID NO 3
<211> LENGTH: 28
<212> TYPE: PRT
<213> ORGANISM: Artificial Sequence
<220> FEATURE:
<223> OTHER INFORMATION: first zinc finger domain encompasses amino acid
      residues 405-432

<400> SEQUENCE: 3

Thr Gly Glu Arg Pro Phe Val Cys Ser Val Cys Gly His Arg Phe Thr
1               5                   10                  15

Thr Lys Gly Asn Leu Lys Val His Phe His Arg His
            20                  25

<210> SEQ ID NO 4
<211> LENGTH: 28

```
<212> TYPE: PRT
<213> ORGANISM: Artificial Sequence
<220> FEATURE:
<223> OTHER INFORMATION: second zinc finger domain encompasses amino
      acid residues 589-616

<400> SEQUENCE: 4

Thr Gly Glu Arg Pro Phe Gln Cys Lys Ile Cys Gly Arg Ala Phe Ser
1               5                   10                  15

Thr Lys Gly Asn Leu Lys Thr His Leu Gly Val His
            20                  25

<210> SEQ ID NO 5
<211> LENGTH: 28
<212> TYPE: PRT
<213> ORGANISM: Artificial Sequence
<220> FEATURE:
<223> OTHER INFORMATION: third zinc finger domain encompasses amino acid
      residues 865-892

<400> SEQUENCE: 5

Arg Gln Ala Lys Gln His Gly Cys Thr Arg Cys Gly Lys Asn Phe Ser
1               5                   10                  15

Ser Ala Ser Ala Leu Gln Ile His Glu Arg Thr His
            20                  25

<210> SEQ ID NO 6
<211> LENGTH: 28
<212> TYPE: PRT
<213> ORGANISM: Artificial Sequence
<220> FEATURE:
<223> OTHER INFORMATION: fourth zinc finger domain encompasses amino
      acid residues 893-920

<400> SEQUENCE: 6

Thr Gly Glu Lys Pro Phe Val Cys Asn Ile Cys Gly Arg Ala Phe Thr
1               5                   10                  15

Thr Lys Gly Asn Leu Lys Val His Tyr Met Thr His
            20                  25

<210> SEQ ID NO 7
<211> LENGTH: 29
<212> TYPE: PRT
<213> ORGANISM: Artificial Sequence
<220> FEATURE:
<223> OTHER INFORMATION: Ikaros zinc finger domain (amino acid residues
      140-168)

<400> SEQUENCE: 7

Thr Gly Glu Arg Pro Phe Gln Cys Asn Gln Cys Gly Ala Ser Phe Thr
1               5                   10                  15

Gln Lys Gly Asn Leu Leu Arg His Ile Lys Leu His Ser
            20                  25

<210> SEQ ID NO 8
<211> LENGTH: 23
<212> TYPE: PRT
<213> ORGANISM: Artificial Sequence
<220> FEATURE:
<223> OTHER INFORMATION: Ikaros (amino acid residues 145-167)

<400> SEQUENCE: 8

Phe Gln Cys Asn Gln Cys Gly Ala Ser Phe Thr Gln Lys Gly Asn Leu
1               5                   10                  15

Leu Arg His Ile Lys Leu His
```

```
<210> SEQ ID NO 9
<211> LENGTH: 23
<212> TYPE: PRT
<213> ORGANISM: Artificial Sequence
<220> FEATURE:
<223> OTHER INFORMATION: ZFP91 (amino acid residues 400-422)

<400> SEQUENCE: 9

Leu Gln Cys Glu Ile Cys Gly Phe Thr Cys Arg Gln Lys Ala Ser Leu
1               5                   10                  15

Asn Trp His Met Lys Lys His
            20

<210> SEQ ID NO 10
<211> LENGTH: 23
<212> TYPE: PRT
<213> ORGANISM: Artificial Sequence
<220> FEATURE:
<223> OTHER INFORMATION: SALL4-ZF1

<400> SEQUENCE: 10

His Lys Cys Lys Tyr Cys Ser Lys Val Phe Gly Thr Asp Ser Ser Leu
1               5                   10                  15

Gln Ile His Leu Arg Ser His
            20

<210> SEQ ID NO 11
<211> LENGTH: 23
<212> TYPE: PRT
<213> ORGANISM: Artificial Sequence
<220> FEATURE:
<223> OTHER INFORMATION: SALL4-ZF2

<400> SEQUENCE: 11

Phe Val Cys Ser Val Cys Gly His Arg Phe Thr Thr Lys Gly Asn Leu
1               5                   10                  15

Lys Val His Phe His Arg His
            20

<210> SEQ ID NO 12
<211> LENGTH: 23
<212> TYPE: PRT
<213> ORGANISM: Artificial Sequence
<220> FEATURE:
<223> OTHER INFORMATION: SALL4-ZF3

<400> SEQUENCE: 12

Asn Glu Cys Leu Ile Cys His Arg Val Leu Ser Cys Gln Ser Ser Leu
1               5                   10                  15

Lys Met His Tyr Arg Thr His
            20

<210> SEQ ID NO 13

<400> SEQUENCE: 13

000

<210> SEQ ID NO 14
<211> LENGTH: 23
<212> TYPE: PRT
<213> ORGANISM: Artificial Sequence
<220> FEATURE:
```

<223> OTHER INFORMATION: SALL4-ZF4

<400> SEQUENCE: 14

Phe Gln Cys Lys Ile Cys Gly Arg Ala Phe Ser Thr Lys Gly Asn Leu
1               5                   10                  15

Lys Thr His Leu Gly Val His
            20

<210> SEQ ID NO 15
<211> LENGTH: 23
<212> TYPE: PRT
<213> ORGANISM: Artificial Sequence
<220> FEATURE:
<223> OTHER INFORMATION: SALL4-ZF5

<400> SEQUENCE: 15

His Ser Cys Pro Ile Cys Gln Lys Lys Phe Thr Asn Ala Val Met Leu
1               5                   10                  15

Gln Gln His Ile Arg Met His
            20

<210> SEQ ID NO 16
<211> LENGTH: 23
<212> TYPE: PRT
<213> ORGANISM: Artificial Sequence
<220> FEATURE:
<223> OTHER INFORMATION: SALL4-ZF6

<400> SEQUENCE: 16

His Gly Cys Thr Arg Cys Gly Lys Asn Phe Ser Ser Ala Ser Ala Leu
1               5                   10                  15

Gln Ile His Glu Arg Thr His
            20

<210> SEQ ID NO 17
<211> LENGTH: 23
<212> TYPE: PRT
<213> ORGANISM: Artificial Sequence
<220> FEATURE:
<223> OTHER INFORMATION: SALL4-ZF7

<400> SEQUENCE: 17

Phe Val Cys Asn Ile Cys Gly Arg Ala Phe Thr Thr Lys Gly Asn Leu
1               5                   10                  15

Lys Val His Tyr Met Thr His
            20

<210> SEQ ID NO 18
<211> LENGTH: 442
<212> TYPE: PRT
<213> ORGANISM: Homo sapiens
<220> FEATURE:
<223> OTHER INFORMATION: Human Cereblon

<400> SEQUENCE: 18

Met Ala Gly Glu Gly Asp Gln Gln Asp Ala Ala His Asn Met Gly Asn
1               5                   10                  15

His Leu Pro Leu Leu Pro Ala Glu Ser Glu Glu Glu Asp Glu Met Glu
            20                  25                  30

Val Glu Asp Gln Asp Ser Lys Glu Ala Lys Lys Pro Asn Ile Ile Asn
        35                  40                  45

Phe Asp Thr Ser Leu Pro Thr Ser His Thr Tyr Leu Gly Ala Asp Met
    50                  55                  60

Glu Phe His Gly Arg Thr Leu His Asp Asp Ser Cys Gln Val
65                  70                  75                  80

Ile Pro Val Leu Pro Gln Val Met Met Ile Leu Ile Pro Gly Gln Thr
                85                  90                  95

Leu Pro Leu Gln Leu Phe His Pro Gln Glu Val Ser Met Val Arg Asn
                100                 105                 110

Leu Ile Gln Lys Asp Arg Thr Phe Ala Val Leu Ala Tyr Ser Asn Val
                115                 120                 125

Gln Glu Arg Glu Ala Gln Phe Gly Thr Thr Ala Glu Ile Tyr Ala Tyr
            130                 135                 140

Arg Glu Glu Gln Asp Phe Gly Ile Glu Ile Val Lys Val Lys Ala Ile
145                 150                 155                 160

Gly Arg Gln Arg Phe Lys Val Leu Glu Leu Arg Thr Gln Ser Asp Gly
                165                 170                 175

Ile Gln Gln Ala Lys Val Gln Ile Leu Pro Glu Cys Val Leu Pro Ser
            180                 185                 190

Thr Met Ser Ala Val Gln Leu Glu Ser Leu Asn Lys Cys Gln Ile Phe
            195                 200                 205

Pro Ser Lys Pro Val Ser Arg Glu Asp Gln Cys Ser Tyr Lys Trp Trp
210                 215                 220

Gln Lys Tyr Gln Lys Arg Lys Phe His Cys Ala Asn Leu Thr Ser Trp
225                 230                 235                 240

Pro Arg Trp Leu Tyr Ser Leu Tyr Asp Ala Glu Thr Leu Met Asp Arg
                245                 250                 255

Ile Lys Lys Gln Leu Arg Glu Trp Asp Glu Asn Leu Lys Asp Asp Ser
                260                 265                 270

Leu Pro Ser Asn Pro Ile Asp Phe Ser Tyr Arg Val Ala Ala Cys Leu
                275                 280                 285

Pro Ile Asp Asp Val Leu Arg Ile Gln Leu Leu Lys Ile Gly Ser Ala
290                 295                 300

Ile Gln Arg Leu Arg Cys Glu Leu Asp Ile Met Asn Lys Cys Thr Ser
305                 310                 315                 320

Leu Cys Cys Lys Gln Cys Gln Glu Thr Glu Ile Thr Thr Lys Asn Glu
                325                 330                 335

Ile Phe Ser Leu Ser Leu Cys Gly Pro Met Ala Ala Tyr Val Asn Pro
                340                 345                 350

His Gly Tyr Val His Glu Thr Leu Thr Val Tyr Lys Ala Cys Asn Leu
                355                 360                 365

Asn Leu Ile Gly Arg Pro Ser Thr Glu His Ser Trp Phe Pro Gly Tyr
                370                 375                 380

Ala Trp Thr Val Ala Gln Cys Lys Ile Cys Ala Ser His Ile Gly Trp
385                 390                 395                 400

Lys Phe Thr Ala Thr Lys Lys Asp Met Ser Pro Gln Lys Phe Trp Gly
                405                 410                 415

Leu Thr Arg Ser Ala Leu Leu Pro Thr Ile Pro Asp Thr Glu Asp Glu
                420                 425                 430

Ile Ser Pro Asp Lys Val Ile Leu Cys Leu
                435                 440

<210> SEQ ID NO 19
<211> LENGTH: 487
<212> TYPE: PRT
<213> ORGANISM: Oryctolagus cuniculus
<220> FEATURE:

<223> OTHER INFORMATION: Rabbit Cereblon

<400> SEQUENCE: 19

Met Asp Ser Trp Arg Pro Leu Asp Arg Leu Ser Gln Ala Gly Ala Asp
1               5                   10                  15

Gly Glu Asp Glu Ser Glu Asp Glu Met Glu Val Glu Asp Gln
            20                  25                  30

Asp Ser Lys Glu Ala Lys Lys Pro Asn Ile Ile Asn Phe Asp Thr Ser
            35                  40                  45

Leu Pro Thr Ser His Thr Tyr Leu Gly Ala Asp Met Glu Glu Phe His
        50                  55                  60

Gly Arg Thr Leu His Asp Asp Ser Cys Pro Val Ile Pro Val Leu
65                  70                  75                  80

Pro Gln Val Val Met Ile Leu Ile Pro Gly Gln Thr Leu Pro Leu Gln
                85                  90                  95

Leu Ser His Pro Pro Glu Val Ser Met Val Arg Ser Leu Ile Gln Lys
            100                 105                 110

Asp Arg Thr Phe Ala Val Leu Ala Tyr Ser Asn Val Gln Glu Arg Glu
            115                 120                 125

Ala Gln Phe Gly Thr Thr Ala Glu Ile Tyr Ala Tyr Arg Glu Glu Gln
        130                 135                 140

Asp Phe Gly Ile Glu Ile Val Lys Val Lys Ala Val Gly Arg Gln Arg
145                 150                 155                 160

Phe Lys Val Leu Glu Leu Arg Thr Gln Ser Asp Gly Ile Gln Gln Ala
                165                 170                 175

Lys Val Gln Ile Leu Pro Glu Cys Val Leu Pro Ser Thr Met Ser Ala
            180                 185                 190

Val Gln Leu Glu Ser Leu Asn Lys Cys Gln Ile Phe Pro Ser Lys Pro
        195                 200                 205

Val Ser Trp Glu Asp Gln Cys Ser Tyr Lys Trp Trp Gln Lys Tyr Gln
    210                 215                 220

Lys Arg Lys Phe His Cys Ala Asn Leu Thr Ser Trp Pro Arg Trp Leu
225                 230                 235                 240

Tyr Ser Leu Tyr Asp Ala Glu Thr Leu Met Asp Arg Ile Lys Lys Gln
                245                 250                 255

Leu Arg Glu Trp Asp Glu Asn Leu Lys Asp Asp Ser Leu Pro Ser Asn
            260                 265                 270

Pro Ile Asp Phe Ser Tyr Arg Val Ala Ala Cys Leu Pro Ile Asp Asp
        275                 280                 285

Val Leu Arg Ile Gln Leu Leu Lys Ile Gly Ser Ala Ile Gln Arg Leu
    290                 295                 300

Arg Cys Glu Leu Asp Ile Met Asn Lys Cys Thr Ser Leu Cys Cys Lys
305                 310                 315                 320

Gln Cys Gln Glu Thr Glu Ile Thr Thr Lys Asn Glu Ile Phe Ser Leu
                325                 330                 335

Ser Leu Cys Gly Pro Met Ala Ala Tyr Val Asn Pro His Gly Tyr Val
            340                 345                 350

His Glu Thr Leu Thr Val Tyr Lys Ala Cys Asn Leu Asn Leu Ile Gly
        355                 360                 365

Arg Pro Ser Thr Glu His Ser Trp Phe Pro Gly Tyr Ala Trp Thr Val
    370                 375                 380

Ala Gln Cys Lys Ile Cys Ala Ser His Ile Gly Trp Lys Phe Thr Ala
385                 390                 395                 400

```
Thr Lys Lys Asp Met Ser Pro Gln Lys Phe Trp Gly Leu Thr Arg Ser
                405                 410                 415
Ala Leu Leu Pro Thr Ile Pro Asp Thr Glu Asp Glu Leu Ser Pro Asp
            420                 425                 430
Arg Ser Val Arg Leu Arg Gln His Thr Trp Asp Arg Gln Met His Ser
        435                 440                 445
Arg His Thr Arg Asp Pro Thr Tyr Val Ala Arg Gly Arg Arg Pro Val
    450                 455                 460
Gly Ser Ala Val Leu Gly Arg Lys Arg Trp Leu Cys Val Ala Val Asp
465                 470                 475                 480
Ser Gln Gly Cys Val Thr Pro
                485

<210> SEQ ID NO 20
<211> LENGTH: 445
<212> TYPE: PRT
<213> ORGANISM: Mus
<220> FEATURE:
<223> OTHER INFORMATION: Mouse Cereblon

<400> SEQUENCE: 20

Met Ala Gly Glu Gly Asp Gln Gln Asp Ala Ala His Asn Met Gly Asn
1               5                   10                  15
His Leu Pro Leu Leu Pro Ala Asp Ser Glu Asp Glu Asp Asp Glu Ile
            20                  25                  30
Glu Met Glu Val Glu Asp Gln Asp Ser Lys Glu Ala Arg Lys Pro Asn
        35                  40                  45
Ile Ile Asn Phe Asp Thr Ser Leu Pro Thr Ser His Thr Tyr Leu Gly
    50                  55                  60
Ala Asp Met Glu Glu Phe His Gly Arg Thr Leu His Asp Asp Asp Ser
65                  70                  75                  80
Cys Gln Val Ile Pro Val Leu Pro Glu Val Leu Met Ile Leu Ile Pro
                85                  90                  95
Gly Gln Thr Leu Pro Leu Gln Leu Ser His Pro Gln Glu Val Ser Met
            100                 105                 110
Val Arg Asn Leu Ile Gln Lys Asp Arg Thr Phe Ala Val Leu Ala Tyr
        115                 120                 125
Ser Asn Val Gln Glu Arg Glu Ala Gln Phe Gly Thr Thr Ala Glu Ile
    130                 135                 140
Tyr Ala Tyr Arg Glu Glu Gln Glu Phe Gly Ile Glu Val Val Lys Val
145                 150                 155                 160
Lys Ala Ile Gly Arg Gln Arg Phe Lys Val Leu Glu Leu Arg Thr Gln
                165                 170                 175
Ser Asp Gly Ile Gln Gln Ala Lys Val Gln Ile Leu Pro Glu Cys Val
            180                 185                 190
Leu Pro Ser Thr Met Ser Ala Val Gln Leu Glu Ser Leu Asn Lys Cys
        195                 200                 205
Gln Val Phe Pro Ser Lys Pro Ile Ser Trp Glu Asp Gln Tyr Ser Cys
    210                 215                 220
Lys Trp Trp Gln Lys Tyr Gln Lys Arg Lys Phe His Cys Ala Asn Leu
225                 230                 235                 240
Thr Ser Trp Pro Arg Trp Leu Tyr Ser Leu Tyr Asp Ala Glu Thr Leu
                245                 250                 255
Met Asp Arg Ile Lys Lys Gln Leu Arg Glu Trp Asp Glu Asn Leu Lys
            260                 265                 270
```

```
Asp Asp Ser Leu Pro Glu Asn Pro Ile Asp Phe Ser Tyr Arg Val Ala
            275                 280                 285

Ala Cys Leu Pro Ile Asp Asp Val Leu Arg Ile Gln Leu Leu Lys Ile
    290                 295                 300

Gly Ser Ala Ile Gln Arg Leu Arg Cys Glu Leu Asp Ile Met Asn Lys
305                 310                 315                 320

Cys Thr Ser Leu Cys Cys Lys Gln Cys Gln Glu Thr Glu Ile Thr Thr
                325                 330                 335

Lys Asn Glu Ile Phe Ser Leu Ser Leu Cys Gly Pro Met Ala Ala Tyr
                340                 345                 350

Val Asn Pro His Gly Tyr Val His Glu Thr Leu Thr Val Tyr Lys Ala
            355                 360                 365

Ser Asn Leu Asn Leu Ile Gly Arg Pro Ser Thr Val His Ser Trp Phe
    370                 375                 380

Pro Gly Tyr Ala Trp Thr Ile Ala Gln Cys Lys Ile Cys Ala Ser His
385                 390                 395                 400

Ile Gly Trp Lys Phe Thr Ala Thr Lys Lys Asp Met Ser Pro Gln Lys
                405                 410                 415

Phe Trp Gly Leu Thr Arg Ser Ala Leu Leu Pro Thr Ile Pro Glu Thr
            420                 425                 430

Glu Asp Glu Ile Ser Pro Asp Lys Val Ile Leu Cys Leu
    435                 440                 445

<210> SEQ ID NO 21
<211> LENGTH: 1053
<212> TYPE: PRT
<213> ORGANISM: Homo sapiens
<220> FEATURE:
<223> OTHER INFORMATION: Human SALL4A

<400> SEQUENCE: 21

Met Ser Arg Arg Lys Gln Ala Lys Pro Gln His Ile Asn Ser Glu Glu
1               5                   10                  15

Asp Gln Gly Glu Gln Gln Pro Gln Gln Gln Thr Pro Glu Phe Ala Asp
                20                  25                  30

Ala Ala Pro Ala Ala Pro Ala Ala Gly Glu Leu Gly Ala Pro Val Asn
            35                  40                  45

His Pro Gly Asn Asp Glu Val Ala Ser Glu Asp Glu Ala Thr Val Lys
        50                  55                  60

Arg Leu Arg Arg Glu Glu Thr His Val Cys Glu Lys Cys Cys Ala Glu
65                  70                  75                  80

Phe Phe Ser Ile Ser Glu Phe Leu Glu His Lys Lys Asn Cys Thr Lys
                85                  90                  95

Asn Pro Pro Val Leu Ile Met Asn Asp Ser Glu Gly Pro Val Pro Ser
            100                 105                 110

Glu Asp Phe Ser Gly Ala Val Leu Ser His Gln Pro Thr Ser Pro Gly
        115                 120                 125

Ser Lys Asp Cys His Arg Glu Asn Gly Gly Ser Ser Glu Asp Met Lys
    130                 135                 140

Glu Lys Pro Asp Ala Glu Ser Val Val Tyr Leu Lys Thr Glu Thr Ala
145                 150                 155                 160

Leu Pro Pro Thr Pro Gln Asp Ile Ser Tyr Leu Ala Lys Gly Lys Val
                165                 170                 175

Ala Asn Thr Asn Val Thr Leu Gln Ala Leu Arg Gly Thr Lys Val Ala
            180                 185                 190
```

```
Val Asn Gln Arg Ser Ala Asp Ala Leu Pro Ala Pro Val Pro Gly Ala
            195                 200                 205
Asn Ser Ile Pro Trp Val Leu Glu Gln Ile Leu Cys Leu Gln Gln Gln
        210                 215                 220
Gln Leu Gln Gln Ile Gln Leu Thr Glu Gln Ile Arg Ile Gln Val Asn
225                 230                 235                 240
Met Trp Ala Ser His Ala Leu His Ser Ser Gly Ala Gly Ala Asp Thr
                245                 250                 255
Leu Lys Thr Leu Gly Ser His Met Ser Gln Gln Val Ser Ala Ala Val
            260                 265                 270
Ala Leu Leu Ser Gln Lys Ala Gly Ser Gln Gly Leu Ser Leu Asp Ala
        275                 280                 285
Leu Lys Gln Ala Lys Leu Pro His Ala Asn Ile Pro Ser Ala Thr Ser
290                 295                 300
Ser Leu Ser Pro Gly Leu Ala Pro Phe Thr Leu Lys Pro Asp Gly Thr
305                 310                 315                 320
Arg Val Leu Pro Asn Val Met Ser Arg Leu Pro Ser Ala Leu Leu Pro
                325                 330                 335
Gln Ala Pro Gly Ser Val Leu Phe Gln Ser Pro Phe Ser Thr Val Ala
            340                 345                 350
Leu Asp Thr Ser Lys Lys Gly Lys Gly Lys Pro Pro Asn Ile Ser Ala
        355                 360                 365
Val Asp Val Lys Pro Lys Asp Glu Ala Ala Leu Tyr Lys His Lys Cys
370                 375                 380
Lys Tyr Cys Ser Lys Val Phe Gly Thr Asp Ser Ser Leu Gln Ile His
385                 390                 395                 400
Leu Arg Ser His Thr Gly Glu Arg Pro Phe Val Cys Ser Val Cys Gly
                405                 410                 415
His Arg Phe Thr Thr Lys Gly Asn Leu Lys Val His Phe His Arg His
            420                 425                 430
Pro Gln Val Lys Ala Asn Pro Gln Leu Phe Ala Glu Phe Gln Asp Lys
        435                 440                 445
Val Ala Ala Gly Asn Gly Ile Pro Tyr Ala Leu Ser Val Pro Asp Pro
450                 455                 460
Ile Asp Glu Pro Ser Leu Ser Leu Asp Ser Lys Pro Val Leu Val Thr
465                 470                 475                 480
Thr Ser Val Gly Leu Pro Gln Asn Leu Ser Gly Thr Asn Pro Lys
                485                 490                 495
Asp Leu Thr Gly Gly Ser Leu Pro Gly Asp Leu Gln Pro Gly Pro Ser
            500                 505                 510
Pro Glu Ser Glu Gly Gly Pro Thr Leu Pro Gly Val Gly Pro Asn Tyr
        515                 520                 525
Asn Ser Pro Arg Ala Gly Gly Phe Gln Gly Ser Gly Thr Pro Glu Pro
530                 535                 540
Gly Ser Glu Thr Leu Lys Leu Gln Gln Leu Val Glu Asn Ile Asp Lys
545                 550                 555                 560
Ala Thr Thr Asp Pro Asn Glu Cys Leu Ile Cys His Arg Val Leu Ser
                565                 570                 575
Cys Gln Ser Ser Leu Lys Met His Tyr Arg Thr His Thr Gly Glu Arg
            580                 585                 590
Pro Phe Gln Cys Lys Ile Cys Gly Arg Ala Phe Ser Thr Lys Gly Asn
        595                 600                 605
Leu Lys Thr His Leu Gly Val His Arg Thr Asn Thr Ser Ile Lys Thr
```

```
                610             615             620
Gln His Ser Cys Pro Ile Cys Gln Lys Lys Phe Thr Asn Ala Val Met
625             630             635             640

Leu Gln Gln His Ile Arg Met His Met Gly Gly Gln Ile Pro Asn Thr
                645             650             655

Pro Leu Pro Glu Asn Pro Cys Asp Phe Thr Gly Ser Glu Pro Met Thr
                660             665             670

Val Gly Glu Asn Gly Ser Thr Gly Ala Ile Cys His Asp Val Ile
            675             680             685

Glu Ser Ile Asp Val Glu Val Ser Ser Gln Glu Ala Pro Ser Ser
690             695             700

Ser Ser Lys Val Pro Thr Pro Leu Pro Ser Ile His Ser Ala Ser Pro
705             710             715             720

Thr Leu Gly Phe Ala Met Met Ala Ser Leu Asp Ala Pro Gly Lys Val
                725             730             735

Gly Pro Ala Pro Phe Asn Leu Gln Arg Gln Gly Ser Arg Glu Asn Gly
                740             745             750

Ser Val Glu Ser Asp Gly Leu Thr Asn Asp Ser Ser Leu Met Gly
            755             760             765

Asp Gln Glu Tyr Gln Ser Arg Ser Pro Asp Ile Leu Glu Thr Thr Ser
770             775             780

Phe Gln Ala Leu Ser Pro Ala Asn Ser Gln Ala Glu Ser Ile Lys Ser
785             790             795             800

Lys Ser Pro Asp Ala Gly Ser Lys Ala Glu Ser Glu Asn Ser Arg
            805             810             815

Thr Glu Met Glu Gly Arg Ser Ser Leu Pro Ser Thr Phe Ile Arg Ala
                820             825             830

Pro Pro Thr Tyr Val Lys Val Glu Val Pro Gly Thr Phe Val Gly Pro
                835             840             845

Ser Thr Leu Ser Pro Gly Met Thr Pro Leu Leu Ala Ala Gln Pro Arg
                850             855             860

Arg Gln Ala Lys Gln His Gly Cys Thr Arg Cys Gly Lys Asn Phe Ser
865             870             875             880

Ser Ala Ser Ala Leu Gln Ile His Glu Arg Thr His Thr Gly Glu Lys
                885             890             895

Pro Phe Val Cys Asn Ile Cys Gly Arg Ala Phe Thr Thr Lys Gly Asn
                900             905             910

Leu Lys Val His Tyr Met Thr His Gly Ala Asn Asn Asn Ser Ala Arg
                915             920             925

Arg Gly Arg Lys Leu Ala Ile Glu Asn Thr Met Ala Leu Leu Gly Thr
930             935             940

Asp Gly Lys Arg Val Ser Glu Ile Phe Pro Lys Glu Ile Leu Ala Pro
945             950             955             960

Ser Val Asn Val Asp Pro Val Val Trp Asn Gln Tyr Thr Ser Met Leu
                965             970             975

Asn Gly Gly Leu Ala Val Lys Thr Asn Glu Ile Ser Val Ile Gln Ser
                980             985             990

Gly Gly Val Pro Thr Leu Pro Val  Ser Leu Gly Ala Thr  Ser Val Val
                995             1000            1005

Asn Asn  Ala Thr Val Ser Lys  Met Asp Gly Ser Gln  Ser Gly Ile
        1010            1015            1020

Ser Ala  Asp Val Glu Lys Pro  Ser Ala Thr Asp Gly  Val Pro Lys
        1025            1030            1035
```

His Gln Phe Pro His Phe Leu Glu Glu Asn Lys Ile Ala Val Ser
            1040                1045                1050

<210> SEQ ID NO 22
<211> LENGTH: 993
<212> TYPE: PRT
<213> ORGANISM: Oryctolagus cuniculus
<220> FEATURE:
<223> OTHER INFORMATION: Rabbit SALL4A

<400> SEQUENCE: 22

Gly Ala Ala Met Asn Gln Pro Gly Thr Gly Asp Asp Ala Pro Gly Asp
1               5                   10                  15

Arg Val Pro Gly Lys Arg Pro Arg Arg Glu Glu Thr His Ile Cys Glu
            20                  25                  30

Lys Cys Cys Ala Glu Phe Phe Ser Leu Ser Glu Phe Leu Glu His Lys
        35                  40                  45

Lys Asn Cys Thr Lys Asn Pro Pro Val Leu Ile Met Ser Asp Ser Glu
    50                  55                  60

Gly Pro Val Pro Ser Glu Asp Phe Ser Gly Ala Val Leu Ser Pro Gly
65                  70                  75                  80

Gly Arg Asp Ser His Arg Glu Ser Gly Gly Ser Ser Gly Asp Thr Lys
                85                  90                  95

Glu Lys Leu Gly Ala Glu Ser Val Val His Leu Lys Ala Glu Thr Thr
            100                 105                 110

Leu Pro Pro Pro Pro Gln Asp Ile Ser Tyr Val Pro Lys Gly Lys Val
        115                 120                 125

Ala Ser Thr Asn Val Thr Leu Gln Ala Leu Arg Gly Thr Lys Val Ala
    130                 135                 140

Val Asn Gln Arg Ser Ala Asp Ala Pro Ala Pro Val Pro Gly Ala
145                 150                 155                 160

Asn Ser Ile Pro Trp Val Leu Glu Gln Ile Leu Cys Leu Gln Gln Gln
                165                 170                 175

Gln Leu Gln Gln Ile Gln Leu Thr Glu Gln Ile Arg Ile Gln Val Asn
            180                 185                 190

Met Trp Ala Ser His Ala Leu His Ser Gly Val Ala Gly Ala Asp Ala
        195                 200                 205

Leu Lys Thr Leu Gly Gly His Val Ser Gln Gln Val Ser Ala Ala Val
    210                 215                 220

Ala Leu Leu Ser Gln Lys Ala Gly Ser Gln Gly Leu Ser Leu Glu Ala
225                 230                 235                 240

Leu Lys Gln Gly Lys Leu Pro His Ala Ser Ile Pro Ser Ala Ala Gly
                245                 250                 255

Ser Leu Ser Ser Gly Leu Thr Pro Phe Ala Leu Lys Pro Asp Gly Ala
            260                 265                 270

Arg Val Leu Pro Ser Val Met Ser Arg Leu Pro Ser Ala Leu Leu Pro
        275                 280                 285

Gln Thr Pro Gly Pro Ala Leu Phe Gln Gly Pro Phe Ser Thr Val Ala
    290                 295                 300

Leu Asp Pro Ser Lys Lys Gly Lys Gly Lys Pro Pro Ser Val Ser Ala
305                 310                 315                 320

Val Asp Val Lys Thr Lys Asp Glu Thr Gly Leu Cys Lys His Lys Cys
                325                 330                 335

Lys Tyr Cys Ser Lys Val Phe Gly Thr Asp Ser Ser Leu Gln Ile His
            340                 345                 350

```
Leu Arg Ser His Thr Gly Glu Arg Pro Phe Val Cys Ser Val Cys Gly
            355                 360                 365

His Arg Phe Thr Thr Lys Gly Asn Leu Lys Val His Phe His Arg His
        370                 375                 380

Pro Gln Val Lys Ala Asn Pro Gln Leu Phe Ala Glu Phe Gln Asp Lys
385                 390                 395                 400

Val Ala Ala Gly Ser Gly Val Pro Phe Ala Leu Ser Val Pro Val Pro
                405                 410                 415

Val Asp Gly Ala Ser Leu Ser Val Asp Ser Lys Pro Val Leu Ala Thr
            420                 425                 430

Gly Ala Pro Ser Val Gly Leu Pro Gln Asn Leu Ser Ser Gly Thr Asn
            435                 440                 445

Pro Lys Asp Leu Leu Gly Ala Pro Leu Pro Ser Asp Leu Gln Pro Pro
        450                 455                 460

Gly Pro Ser Pro Glu Ser Glu Gly Gly Leu Ala Leu Ala Gly Val Gly
465                 470                 475                 480

Pro Asn His Ile Ser Pro Arg Val Gly Gly Phe Gln Gly Ser Ala Val
                485                 490                 495

Pro Glu Pro Gly Ser Glu Thr Leu Lys Leu Gln Gln Leu Val Glu Asn
            500                 505                 510

Ile Asp Lys Ala Thr Thr Asp Pro Asn Glu Cys Leu Ile Cys His Arg
        515                 520                 525

Val Leu Ser Cys Gln Ser Ser Leu Lys Met His Tyr Arg Thr His Thr
        530                 535                 540

Gly Glu Arg Pro Phe Gln Cys Lys Val Cys Gly Arg Ala Phe Ser Thr
545                 550                 555                 560

Gly Asn Leu Lys Thr His Leu Gly Val His Arg Thr Asn Pro Ala Val
                565                 570                 575

Lys Thr Gln His Ser Cys Pro Ile Cys Gln Lys Lys Phe Thr Asn Ala
            580                 585                 590

Val Leu Leu Gln Gln His Ile Arg Met His Met Gly Gly Gln Ile Pro
        595                 600                 605

Asn Thr Pro Leu Pro Glu Gly Pro Cys Asp Phe Cys His Asp Asp Ser
        610                 615                 620

Glu Gly Val Asp Leu Asp Glu Val Ser Leu Gln Asp Val Pro Ser Gly
625                 630                 635                 640

Ser Ser Lys Val Pro Ala Pro Leu Pro Gly Val His Ser Ala Ser Pro
                645                 650                 655

Thr Leu Gly Phe Pro Val Arg Ala Ser Leu Asp Ala Ala Gly Lys Ala
            660                 665                 670

Gly Ala Ala Pro Leu Gly Leu Gln Arg Gln Ser Ser Arg Glu Asn Gly
        675                 680                 685

Ser Val Glu Ser Asp Gly Leu Thr Asn Asp Ser Ser Ser Leu Ile Glu
        690                 695                 700

Asp Pro Glu Tyr Gln Ser Arg Ser Pro Asp Ala Ala Glu Ser Ala Ser
705                 710                 715                 720

Phe Gln Ala Pro Ser Pro Ala Asn Ser Gln Ala Glu Ser Val Lys Ser
                725                 730                 735

Arg Ser Pro Asp Ala Gly Ser Arg Ala Glu Ser Ser Glu Met Gly Gly
            740                 745                 750

His Cys Ser Leu Ala Thr Glu Pro Gly Arg Ser Ser Leu Pro Ser Thr
        755                 760                 765
```

-continued

```
Phe Ile Arg Thr Gln Pro Thr Tyr Val Lys Val Glu Val Pro Gly Pro
    770                 775                 780

Phe Val Gly Pro Ser Thr Leu Ser Pro Gly Thr Thr Pro Leu Leu Val
785                 790                 795                 800

Ala Gln Pro Arg Arg Gln Ala Lys Gln His Gly Cys Thr Arg Cys Gly
                805                 810                 815

Lys Asn Phe Ser Ser Ala Ser Ala Leu Gln Ile His Glu Arg Thr His
                820                 825                 830

Thr Gly Glu Lys Pro Phe Val Cys Asn Ile Cys Gly Arg Ala Phe Thr
            835                 840                 845

Thr Lys Gly Asn Leu Lys Val His Tyr Met Thr His Gly Ala Asn Asn
    850                 855                 860

Asn Ser Ala Arg Arg Gly Arg Lys Leu Ala Ile Glu Asn Thr Met Ala
865                 870                 875                 880

Leu Leu Gly Thr Asp Gly Lys Arg Val Ser Glu Met Phe Pro Lys Glu
                885                 890                 895

Ile Leu Ala Pro Ser Val Asn Val Asp Pro Val Met Trp Thr Gln Tyr
                900                 905                 910

Thr Ser Met Leu Asn Gly Gly Met Ala Val Lys Thr Asn Glu Ile Ser
            915                 920                 925

Val Ile Gln Ser Gly Gly Leu Pro Thr Leu Pro Val Ser Leu Gly Ala
    930                 935                 940

Ser Ser Val Val Ser Asn Ala Thr Val Ser Lys Leu Asp Gly Ser Gln
945                 950                 955                 960

Ser Gly Ile Ser Ala Asp Ala Glu Lys Pro Gly Ala Ala Asp Gly Val
                965                 970                 975

Ala Lys His Gln Phe Pro His Phe Leu Glu Glu Lys Lys Ile Ala Val
            980                 985                 990

Ser
```

<210> SEQ ID NO 23
<211> LENGTH: 1067
<212> TYPE: PRT
<213> ORGANISM: Mus
<220> FEATURE:
<223> OTHER INFORMATION: Mouse SALL4A

<400> SEQUENCE: 23

```
Met Ser Arg Arg Lys Gln Ala Lys Pro Gln His Ile Asn Trp Glu Glu
1               5                   10                  15

Gly Gln Gly Glu Gln Pro Gln Gln Leu Pro Ser Pro Asp Leu Ala Glu
                20                  25                  30

Ala Leu Ala Ala Glu Glu Pro Gly Ala Pro Val Asn Ser Pro Gly Asn
            35                  40                  45

Cys Asp Glu Ala Ser Glu Asp Ser Ile Pro Val Lys Arg Pro Arg Arg
    50                  55                  60

Glu Asp Thr His Ile Cys Asn Lys Cys Cys Ala Glu Phe Phe Ser Leu
65                  70                  75                  80

Ser Glu Phe Met Glu His Lys Lys Ser Cys Thr Lys Thr Pro Pro Val
                85                  90                  95

Leu Ile Met Asn Asp Ser Glu Gly Pro Val Pro Ser Glu Asp Phe Ser
            100                 105                 110

Arg Ala Ala Leu Ser His Gln Leu Gly Ser Pro Ser Asn Lys Asp Ser
        115                 120                 125

Leu Gln Glu Asn Gly Ser Ser Ser Gly Asp Leu Lys Lys Leu Gly Thr
```

```
              130                 135                 140
Asp Ser Ile Leu Tyr Leu Lys Thr Glu Ala Thr Gln Pro Ser Thr Pro
145                 150                 155                 160

Gln Asp Ile Ser Tyr Leu Pro Lys Gly Lys Val Ala Asn Thr Asn Val
                165                 170                 175

Thr Leu Gln Ala Leu Arg Gly Thr Lys Val Ala Val Asn Gln Arg Gly
            180                 185                 190

Ala Glu Ala Pro Met Ala Pro Met Pro Ala Ala Gln Gly Ile Pro Trp
        195                 200                 205

Val Leu Glu Gln Ile Leu Cys Leu Gln Gln Gln Gln Leu Gln Gln Ile
    210                 215                 220

Gln Leu Thr Glu Gln Ile Arg Val Gln Val Asn Met Trp Ala Ala His
225                 230                 235                 240

Ala Leu His Ser Gly Val Ala Gly Ala Asp Thr Leu Lys Ala Leu Ser
                245                 250                 255

Ser His Val Ser Gln Gln Val Ser Val Ser Gln Gln Val Ser Ala Ala
                260                 265                 270

Val Ala Leu Leu Ser Gln Lys Ala Ser Asn Pro Ala Leu Ser Leu Asp
            275                 280                 285

Ala Leu Lys Gln Ala Lys Leu Pro His Ala Ser Val Pro Ser Ala Ala
        290                 295                 300

Ser Pro Leu Ser Ser Gly Leu Thr Ser Phe Thr Leu Lys Pro Asp Gly
305                 310                 315                 320

Thr Arg Val Leu Pro Asn Phe Val Ser Arg Leu Pro Ser Ala Leu Leu
                325                 330                 335

Pro Gln Thr Pro Gly Ser Val Leu Leu Gln Ser Pro Phe Ser Ala Val
            340                 345                 350

Thr Leu Asp Gln Ser Lys Lys Gly Lys Gly Lys Pro Gln Asn Leu Ser
        355                 360                 365

Ala Ser Ala Ser Val Leu Asp Val Lys Ala Lys Asp Glu Val Val Leu
    370                 375                 380

Gly Lys His Lys Cys Arg Tyr Cys Pro Lys Val Phe Gly Thr Asp Ser
385                 390                 395                 400

Ser Leu Gln Ile His Leu Arg Ser His Thr Gly Glu Arg Pro Tyr Val
                405                 410                 415

Cys Pro Ile Cys Gly His Arg Phe Thr Thr Lys Gly Asn Leu Lys Val
            420                 425                 430

His Leu Gln Arg His Pro Glu Val Lys Ala Asn Pro Gln Leu Leu Ala
        435                 440                 445

Glu Phe Gln Asp Lys Gly Ala Val Ser Ala Ser His Tyr Ala Leu
    450                 455                 460

Pro Val Pro Val Pro Ala Asp Glu Ser Ser Leu Ser Val Asp Ala Glu
465                 470                 475                 480

Pro Val Pro Val Thr Gly Thr Pro Ser Leu Gly Leu Pro Gln Lys Leu
                485                 490                 495

Thr Ser Gly Pro Asn Ser Arg Asp Leu Met Gly Gly Ser Leu Pro Asn
            500                 505                 510

Asp Met Gln Pro Gly Pro Ser Glu Ser Glu Ala Gly Leu Pro Leu
        515                 520                 525

Leu Gly Val Gly Met Ile His Asn Pro Pro Lys Ala Gly Gly Phe Gln
    530                 535                 540

Gly Thr Gly Ala Pro Glu Ser Gly Ser Glu Thr Leu Lys Leu Gln Gln
545                 550                 555                 560
```

-continued

```
Leu Val Glu Asn Ile Asp Lys Ala Thr Thr Asp Pro Asn Glu Cys Leu
                565                 570                 575
Ile Cys His Arg Val Leu Ser Cys Gln Ser Ser Leu Lys Met His Tyr
            580                 585                 590
Arg Thr His Thr Gly Glu Arg Pro Phe Gln Cys Lys Ile Cys Gly Arg
        595                 600                 605
Ala Phe Ser Thr Lys Gly Asn Leu Lys Thr His Leu Gly Val His Arg
    610                 615                 620
Thr Asn Thr Thr Val Lys Thr Gln His Ser Cys Pro Ile Cys Gln Lys
625                 630                 635                 640
Lys Phe Thr Asn Ala Val Met Leu Gln Gln His Ile Arg Met His Met
                645                 650                 655
Gly Gly Gln Ile Pro Asn Thr Pro Leu Pro Glu Ser Pro Cys Asp Phe
            660                 665                 670
Thr Ala Pro Glu Pro Val Ala Val Ser Glu Asn Gly Ser Ala Ser Gly
        675                 680                 685
Val Cys Gln Asp Asp Ala Ala Glu Gly Met Glu Ala Glu Glu Val Cys
    690                 695                 700
Ser Gln Asp Val Pro Ser Gly Pro Ser Thr Val Ser Leu Pro Val Pro
705                 710                 715                 720
Ser Ala His Leu Ala Ser Pro Ser Leu Gly Phe Ser Val Leu Ala Ser
                725                 730                 735
Leu Asp Thr Gln Gly Lys Gly Ala Leu Pro Ala Leu Ala Leu Gln Arg
            740                 745                 750
Gln Ser Ser Arg Glu Asn Ser Ser Leu Glu Gly Gly Asp Thr Gly Pro
        755                 760                 765
Ala Asn Asp Ser Ser Leu Leu Val Gly Asp Gln Glu Cys Gln Ser Arg
    770                 775                 780
Ser Pro Asp Ala Thr Glu Thr Met Cys Tyr Gln Ala Val Ser Pro Ala
785                 790                 795                 800
Asn Ser Gln Ala Gly Ser Val Lys Ser Arg Ser Pro Glu Gly His Lys
                805                 810                 815
Ala Glu Gly Val Glu Ser Cys Arg Val Asp Thr Glu Gly Arg Thr Ser
            820                 825                 830
Leu Pro Pro Thr Phe Ile Arg Ala Gln Pro Thr Phe Val Lys Val Glu
        835                 840                 845
Val Pro Gly Thr Phe Val Gly Pro Pro Ser Met Pro Ser Gly Met Pro
    850                 855                 860
Pro Leu Leu Ala Ser Gln Pro Gln Pro Arg Arg Gln Ala Lys Gln His
865                 870                 875                 880
Cys Cys Thr Arg Cys Gly Lys Asn Phe Ser Ser Ala Ser Ala Leu Gln
                885                 890                 895
Ile His Glu Arg Thr His Thr Gly Glu Lys Pro Phe Val Cys Asn Ile
            900                 905                 910
Cys Gly Arg Ala Phe Thr Thr Lys Gly Asn Leu Lys Val His Tyr Met
        915                 920                 925
Thr His Gly Ala Asn Asn Asn Ser Ala Arg Arg Gly Arg Lys Leu Ala
    930                 935                 940
Ile Glu Asn Pro Met Ala Ala Leu Ser Ala Glu Gly Lys Arg Ala Pro
945                 950                 955                 960
Glu Val Phe Ser Lys Glu Leu Leu Ser Pro Ala Val Ser Val Asp Pro
                965                 970                 975
```

```
Ala Ser Trp Asn Gln Tyr Thr Ser Val Leu Asn Gly Gly Leu Ala Met
            980                 985                 990

Lys Thr Asn Glu Ile Ser Val Ile  Gln Ser Gly Gly Ile  Pro Thr Leu
        995             1000                 1005

Pro Val  Ser Leu Gly Ala Ser  Ser Val Val Ser Asn  Gly Thr Ile
    1010             1015             1020

Ser Lys  Leu Asp Gly Ser Gln  Thr Gly Val Ser Met  Pro Met Ser
    1025             1030             1035

Gly Asn  Gly Glu Lys Leu Ala  Val Pro Asp Gly Met  Ala Lys His
    1040             1045             1050

Gln Phe  Pro His Phe Leu Glu  Glu Asn Lys Ile Ala  Val Ser
    1055             1060             1065
```

METHODS FOR SCREENING CEREBLON MODIFYING COMPOUNDS

CROSS-REFERENCE TO RELATED APPLICATIONS

This application claims the benefit of priority of U.S. Provisional Patent Application No. 62/617,112, filed Jan. 12, 2018 and U.S. Provisional Patent Application No. 62/710, 401, filed Feb. 16, 2018, the disclosure of each of which is incorporated by reference herein in its entirety.

SEQUENCE LISTING

This application incorporates by reference in its entirety the Computer Readable Form (CRF) of a Sequence Listing in ASCII text format submitted via EFS-Web. The Sequence Listing text file submitted via EFS-Web, entitled 14247-269-999_SEQ_LISTING.txt, created on Jan. 8, 2019, and is 57,330 bytes in size

1. FIELD

Provided herein, in certain embodiments, are methods for screening cereblon modifying compounds with reduced risk of inducing teratogenicity. Further provided herein, in certain embodiments, are methods for determining if a cereblon modifying compound induces teratogenic effects.

2. BACKGROUND

At least two isoforms of the protein cereblon (CRBN) exist, which are 442 and 441 amino acids long, respectively, and CRBN is conserved from plant to human. In humans, the CRBN gene has been identified as a candidate gene of an autosomal recessive nonsyndromic mental retardation (ARNSMR). See Higgins, J. J. et al., *Neurology*, 2004, 63:1927-1931. CRBN was initially characterized as an RGS-containing novel protein that interacted with a calcium-activated potassium channel protein (SLO1) in the rat brain, and was later shown to interact with a voltage-gated chloride channel (CIC-2) in the retina with AMPK1 and DDB1. See Jo, S. et al., *J. Neurochem,* 2005, 94:1212-1224; Hohberger B. et al., *FEBS Lett,* 2009, 583:633-637; Angers S. et al., *Nature,* 2006, 443:590-593. DDB1 was originally identified as a nucleotide excision repair protein that associates with damaged DNA binding protein 2 (DDB2). Its defective activity causes the repair defect in the patients with xeroderma pigmentosum complementation group E (XPE). DDB1 also appears to function as a component of numerous distinct DCX (DDB1-CUL4-X-box) E3 ubiquitin-protein ligase complexes which mediate the ubiquitination and subsequent proteasomal degradation of target proteins. CRBN has also been identified as a target for the development of therapeutic agents for diseases of the cerebral cortex. See WO 2010/137547 A1.

CRBN has been identified as a key molecular target that binds to therapeutic compounds, such as thalidomide, pomalidomide, and lenalidomide. These drugs target CRBN, and alter the substrate specificity of the ubiquitin ligase, driving the clinical activity in certain cancer cells. Bound substrates are ubiquitinated by the CRBN-CRL4 complex, leading to their degradation by the 26S proteasome. Identification of CRBN downstream substrates and understanding the interactions of CRBN with these substrates will allow the definition of the molecular mechanisms of efficacy and/or toxicity and may lead to drugs with improved efficacy and toxicity profiles.

3. SUMMARY OF THE INVENTION

In one aspect, provided herein is a method comprising: (a) administering a cereblon modifying compound to a sample; and (b) determining if the compound induces degradation of SALL4 protein.

In another aspect, provided herein is a method of screening a cereblon modifying compound for treating a disease or disorder, comprising: (a) obtaining a sample; (b) determining a first protein level of SALL4 in the sample; (c) administering the compound to the sample; (d) determining a second protein level of SALL4 in the sample; (e) comparing the first level and the second protein level of SALL4 to determine if the compound induces degradation of SALL4; and (f) selecting the compound that does not induce degradation of SALL44.

In another aspect, provided herein is a method of screening a cereblon modifying compound for treating a disease or disorder, comprising: (a) obtaining a sample; (b) determining a first protein level of SALL4 in the sample; (c) administering the compound to the sample; (d) determining a second protein level of SALL4 in the sample; (e) comparing the first level and the second protein level of SALL4 to determine the level of SALL4 degradation; and (f) selecting the compound that shows (or induces) reduced degradation of SALL4 as compared with a reference compound. In some embodiments, the reference compound is a cereblon modifying compound that induces degradation of SALL4. In some embodiments, the reference compound is thalidomide. In other embodiments, the reference compound is pomalidomide. In yet other embodiments, the reference compound is lenalidomide. In a specific embodiment, the SALL4 degradation is reduced compared to the SALL4 degradation by thalidomide.

In another aspect, provided herein is a method of screening a cereblon modifying compound for treating a disease or disorder, comprising: (a) administering the compound to a sample; (b) determining the interaction between SALL4 and cereblon in the sample; (c) selecting the compound that does not induce the interaction between SALL4 and cereblon.

In another aspect, provided herein is a method of screening a cereblon modifying compound for treating a disease or disorder, comprising: (a) administering the compound to a sample; (b) determining the interaction between SALL4 and cereblon; (c) selecting the compound that results in (or induces) reduced interaction between SALL4 and cereblon as compared with a reference compound. In some embodiments, the reference compound is a cereblon modifying compound that induces interaction (or binding) SALL4 and cereblon. In some embodiments, the reference compound is thalidomide. In other embodiments, the reference compound is pomalidomide. In yet other embodiments, the reference compound is lenalidomide. In a specific embodiment, the SALL4 degradation is reduced compared to the SALL4 degradation by thalidomide.

In one embodiment, the interaction between SALL4 and cereblon is reduced compared to the interaction between SALL4 and cereblon in the presence of thalidomide.

In some embodiments, the interaction between SALL4 and cereblon is determined by the interaction between amino acid residues 405-432 of SALL4 protein (SEQ ID NO: 3) and cereblon. In some embodiments, the interaction between SALL4 and cereblon is determined by the interaction between amino acid residues 410-432 of SALL4 protein and cereblon.

In another aspect, provided herein is a method of screening a cereblon modifying compound for treating a disease or disorder, comprising: (a) administering the compound to a sample; (b) determining the level of ubiquitination of SALL4 in the sample; (c) selecting the compound that does not induce ubiquitination of SALL44.

In another aspect, provided herein is a method of screening a cereblon modifying compound for treating a disease or disorder, comprising: (a) administering the compound to a sample; (b) determining the level of ubiquitination of SALL4 in the sample; (c) selecting the compound that shows (induces) reduced level of ubiquitination of SALL4 as compared with a reference compound. In some embodiments, the reference compound is a cereblon modifying compound that induces ubiquitination of SALL4. In some embodiments, the reference compound is thalidomide. In other embodiments, the reference compound is pomalidomide. In yet other embodiments, the reference compound is lenalidomide. In one specific embodiment, the SALL4 ubiquitination is reduced compared to the SALL4 ubiquitination by thalidomide.

In some embodiments of the various methods provided herein, the disease or disorder is a cancer. In some embodiments, the cancer is a hematological cancer. In other embodiments, the cancer is a solid cancer. In some embodiments, the cancer is selected from a group consisting of multiple myeloma, lymphoma and leukemia. In a specific embodiment, the cancer is multiple myeloma. In another specific embodiment, the cancer is lymphoma. In yet another specific embodiment, the cancer is leukemia. In other embodiments, the disease or disorder is not a cancer. In one embodiment, the disease or disorder is a disease or disorder requiring a non-teratogenic treatment, for example treatment with a cereblon modifying compound that is non-teratogenic or with reduced teratogenicity compared to treatment with a reference compound. In some embodiments, the reference compound is thalidomide. In other embodiments, the reference compound is pomalidomide. In yet other embodiments, the reference compound is lenalidomide. In a specific embodiment, the teratogenicity is reduced compared to treatment with thalidomide.

In another embodiment, the disease or disorder is a disease or disorder requiring a treatment with a cereblon modifying compound that does not induce SALL4 cereblon interaction, or induces a reduced SALL4 cereblon interaction, compared to treatment with a reference compound. In some embodiments, the reference compound is thalidomide. In other embodiments, the reference compound is pomalidomide. In yet other embodiments, the reference compound is lenalidomide. In a specific embodiment, the SALL4 cereblon interaction is reduced compared to treatment with thalidomide.

In another embodiment, the disease or disorder is a disease or disorder requiring a treatment with a cereblon modifying compound that does not induce a SALL4 ubiquitination, or induces a reduced SALL4 ubiquitination, compared to treatment with a reference compound. In some embodiments, the reference compound is thalidomide. In other embodiments, the reference compound is pomalidomide. In yet other embodiments, the reference compound is lenalidomide. In a specific embodiment, the SALL4 ubiquitination is reduced compared to treatment with thalidomide.

In another embodiment, the disease or disorder is a disease or disorder requiring a treatment with a cereblon modifying compound that does not induce SALL4 degradation, or induces a reduced SALL4 degradation, compared to treatment with a reference compound. In some embodiments, the reference compound is thalidomide. In other embodiments, the reference compound is pomalidomide. In yet other embodiments, the reference compound is lenalidomide. In a specific embodiment, the SALL4 degradation is reduced compared to treatment with thalidomide.

In another aspect, provided herein is a method of determining if a cereblon modifying compound induces a teratogenic effect, comprising: (a) obtaining a sample; (b) determining a first protein level of SALL4 in the sample; (c) administering the compound to the sample; (d) determining a second protein level of SALL4 in the sample; (e) comparing the first level and the second protein level of SALL4 to determine if the compound induces degradation of SALL4; thereby determining the teratogenicity of the compound.

In yet another aspect, provided herein is a method of determining if a cereblon modifying compound induces a teratogenic effect, comprising: (a) administering the cereblon modifying compound to a sample; (b) determining the level of ubiquitination of SALL4 in the sample, thereby determining the teratogenicity of the compound.

In yet another aspect, provided herein is a method of determining if a cereblon modifying compound induces a teratogenic effect, comprising: (a) administering the compound to a sample; (b) determining the interaction between SALL4 and cereblon, wherein the interaction between SALL4 and cereblon indicates the potential for teratogenicity. In some embodiments, the interaction between SALL4 and cereblon is a physical binding between SALL4 and cereblon.

In some embodiments, the interaction between SALL4 and cereblon is determined by the interaction between amino acid residues 405-432 of SALL4 protein (SEQ ID NO: 3) and cereblon. In some embodiments, the interaction between SALL4 and cereblon is determined by the interaction between amino acid residues 410-432 of SALL4 protein (SEQ ID NO: 11) and cereblon.

4. BRIEF DESCRIPTION OF THE FIGURES

Figure 1A:
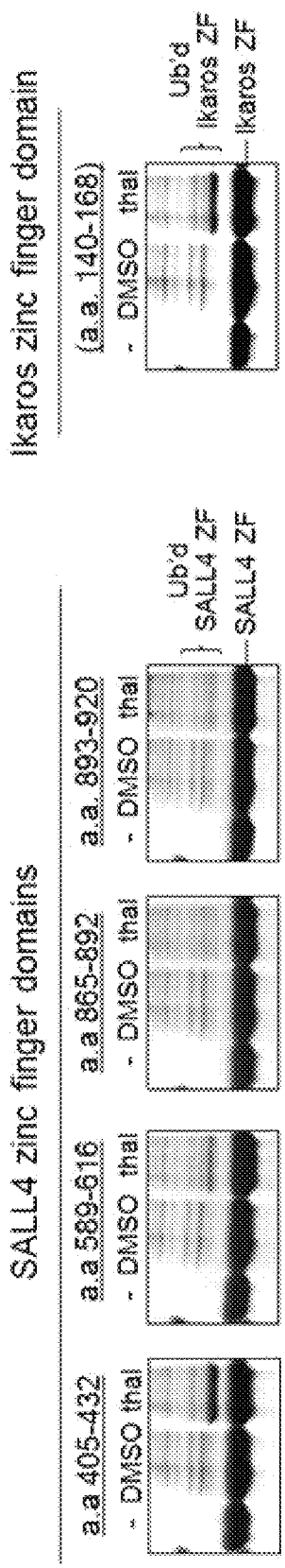
FIG. 1A shows that a particular SALL4 zinc finger domain (a.a. 405-432) is predominantly ubiquitinated by cereblon-CRL4 in a thalidomide-dependent manner (DMSO is negative control). Ubiquitination of the Ikaros zinc finger domain (a.a. 140-168) was used as a positive control.
Figure 1C:
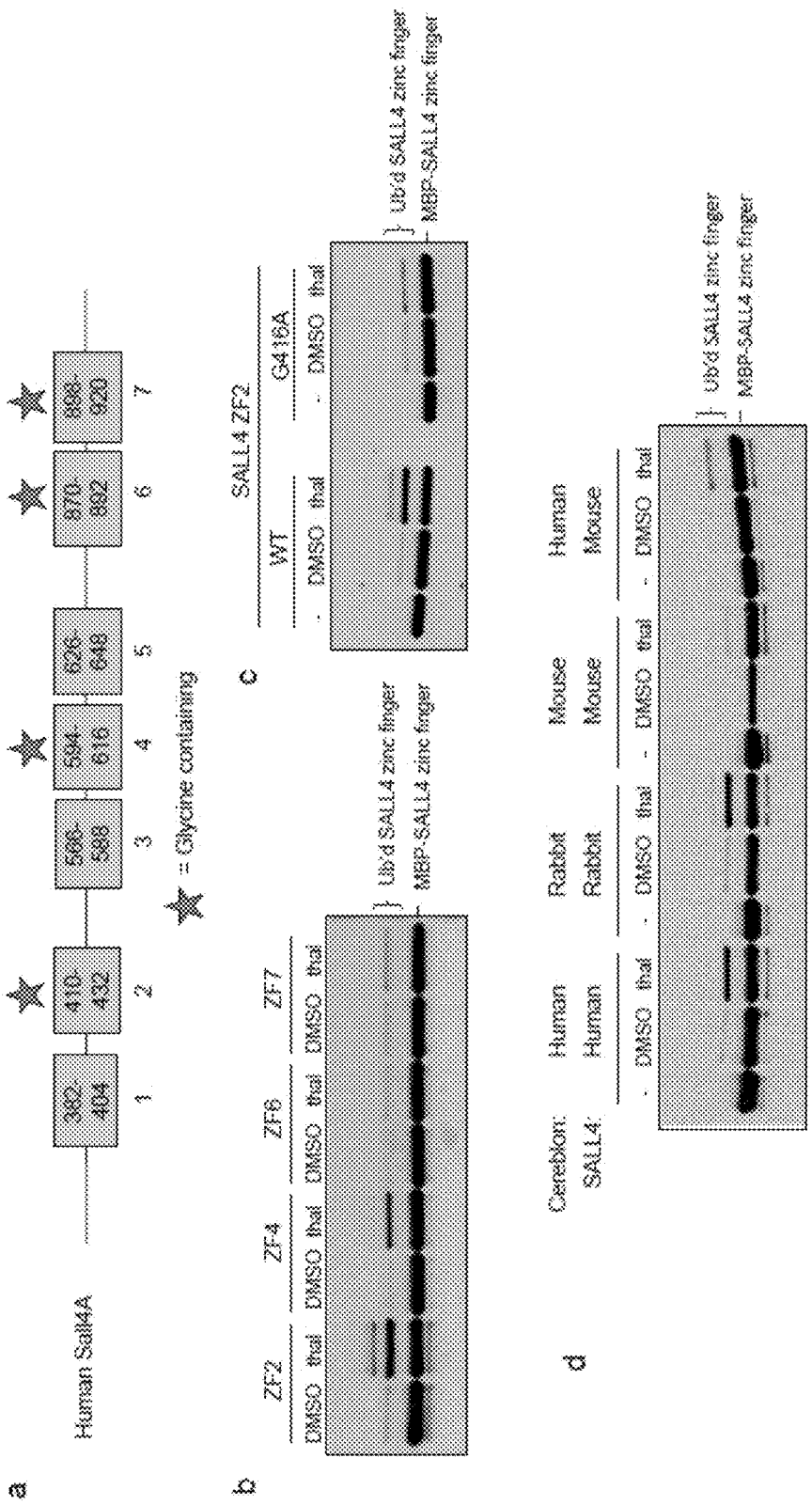
FIG. 1B shows alignment of individual SALL4 zinc fingers with cereblon-binding Ikaros and ZFP91 zinc fingers. The position of the key glycine is highlighted.

FIG. 1C shows human and rabbit SALL4 zinc fingers are direct, thalidomide-dependent substrates of cereblon-CRL4 in vitro, while mouse SALL4 is not recognized. Panel a is a schematic of the SALL4 A protein with zinc finger domains boxed. Glycine degron-containing zinc fingers are highlighted with stars. Panel b shows individual MBP-tagged SALL4 zinc fingers were tested for ubiquitination by cereblon-CRL4 in the absence (DMSO, vehicle control) or presence (thal) of thalidomide. Ubiquitination reactions were separated by SDS-PAGE followed by anti-MBP western blot. SALL4 zinc finger 2 (ZF2, a.a. 410-432) was efficiently ubiquitinated by cereblon-CRL4 in a thalidomide-dependent manner, with weak ubiquitination of SALL4 zinc finger 4 (ZF4, a.a. 594-616). Panel c shows ubiquitination of SALL4 zinc fingers is dependent upon the key glycine in the beta-hairpin cereblon binding motif MBP-tagged WT and G416A SALL4 zinc finger 2 was tested for ubiquitination before separation by SDS-PAGE and western blotting with an anti-MBP antibody. Mutation of the key glycine significantly reduced ubiquitination, indicating that this SALL4 zinc finger binds cereblon using the established glycine-containing beta-hairpin motif. "–" denotes complete reactions including thalidomide but lacking ATP. Panel d shows that rabbit SALL4 can be targeted by rabbit cereblon, while mouse SALL4 cannot be targeted by either mouse or human cereblon. Human SALL4 zinc finger 2 or orthologous rabbit and mouse zinc fingers were tested for in vitro ubiquitination by human, rabbit, or mouse cereblon as indicated. Rabbit zinc finger 2 (a.a. 362-389) ubiquitinatation by rabbit cereblon has similar efficiency to human SALL4 ubiquitination is by human cereblon. In contrast, mouse SALL4 zinc finger 2 (a.a. 415-437) is not efficiently ubiquitinated by mouse or human cereblon. "–" denotes complete reactions including thalidomide but lacking ATP. Results in panels b-d are each representative of 3 independent experiments.

Figure 1D:
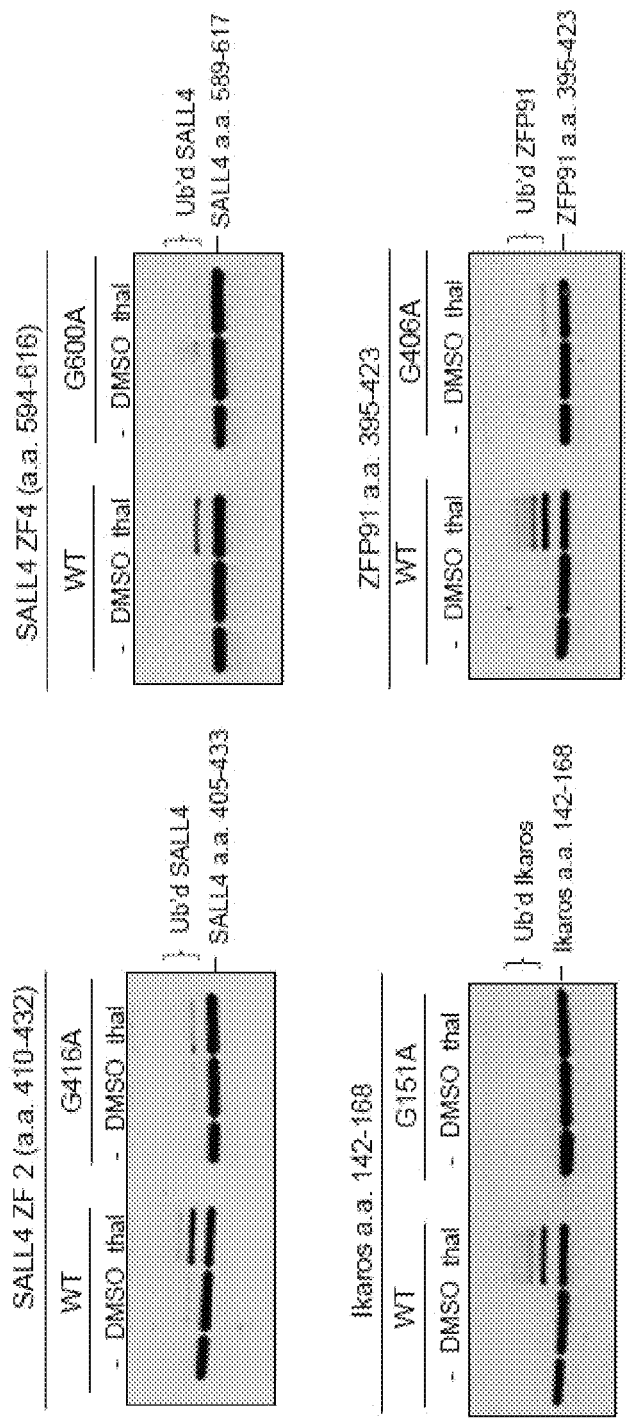

FIG. 1D shows that mutation of G416A in SALL4 zinc finger 2 (a.a. 410-432) and G600A in SALL4 zinc finger 4 (a.a. 594-616) significantly reduced the ubiquitination of the respective zinc finger, similar to the analogous mutation in Ikaros and ZFP91 cereblon-binding zinc fingers, indicating that SALL4 zinc fingers bind to cereblon using the established glycine-containing motif. MBP-tagged wild-type and glycine mutant SALL4 zinc fingers were individually purified and tested for in vitro ubiquitination by purified cereblon-CRL4 before separation by SDS-PAGE and western blotting with an anti-MBP antibody. Results are representative of 3 independent experiments.

FIG. 1E shows alignment of human, rabbit and mouse cereblon showing amino acid differences between the species. E377 and V388 have been shown to be critical for substrate binding in humans and disruptive to substrate binding in mice, and are highlighted. Rabbit has the human amino acids at these positions. Multiple sequence alignment were generated using CLUSTAL 0 (1.2.4).

FIG. 1F shows alignment of human, rabbit, and mouse SALL4 showing amino acid differences between the species. Human zinc finger 2 that is strongly ubiquitinated by cereblon-CRL4+thalidomide is highlighted. The key glycine residue for cereblon binding is indicated. Multiple sequence alignment were generated using CLUSTAL 0 (1.2.4).

Figure 1G:
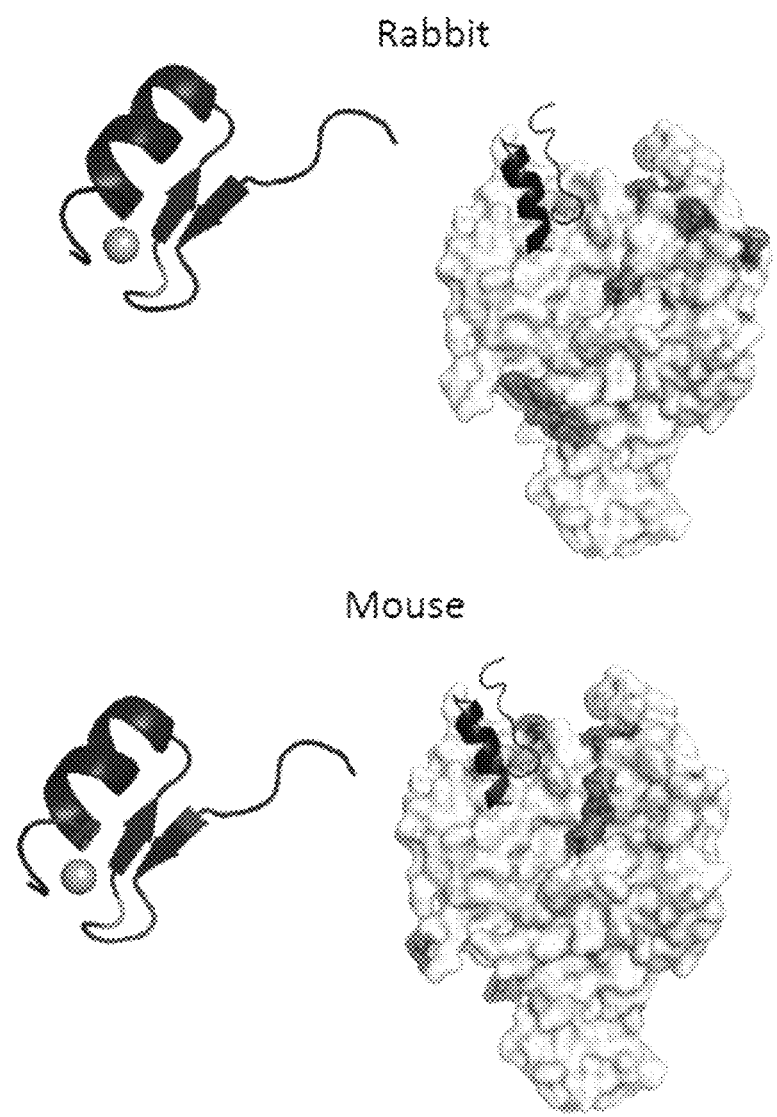

FIG. 1G shows structural models of the SALL4 zinc finger 2 backbone (left), and cereblon with SALL4 zinc finger bound in the presence of thalidomide (right), with amino acid sequence differences from human highlighted. SALL4 zinc finger 2 is 100% conserved in rabbit, but has 5 amino acid differences in the mouse. Rabbit cereblon shows no amino acid differences in the region surrounding the substrate binding site, while mouse cereblon contains two amino acid differences that surround the thalidomide-binding pocket (E377V and V388I) and disrupt cereblon neosubstrate binding.

Figure 1H:
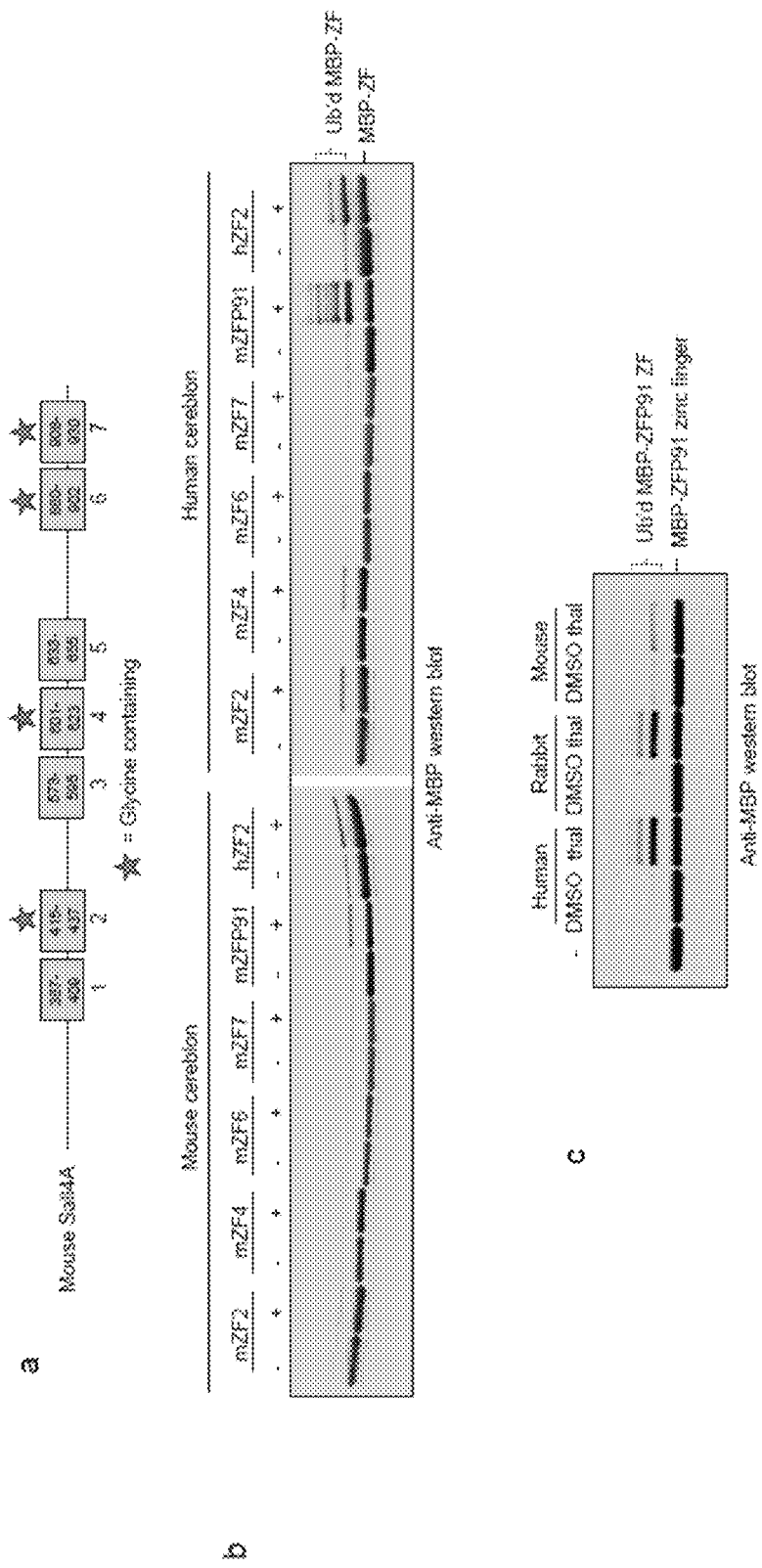

FIG. 1H shows mouse SALL4 zinc fingers are not efficiently ubiquitinated by human or mouse cereblon. Panel a shows a schematic of the mouse SALL4 A protein with zinc finger domains boxed. Glycine degron-containing zinc fingers are highlighted with stars. Panel b shows that individual MBP-tagged SALL4 zinc fingers were tested for ubiquitination by either mouse cereblon (left panel) or human cereblon (right panel), absence (DMSO, vehicle control) or presence (thal) of thalidomide. Ubiquitination reactions were separated by SDS-PAGE followed by anti-MBP western blot. The ZFP91 cereblon-binding zinc finger (a.a. 395-423), which is 100% conserved between human, rabbit, and mouse, and the human SALL4 zinc finger 2 (ZF2, a.a. 410-432) are shown for comparison, both are efficiently ubiquitinated by human cereblon in a thalidomide-dependent manner. Panel c shows that the ZFP91 cereblon-binding zinc finger (a.a. 395-423), which is 100% conserved between human, rabbit, and mouse, was tested for ubiquitination by human, rabbit, and mouse cereblon. ZFP91 can be efficiently ubiquitinated by human and rabbit cereblon, but not by mouse cereblon. This indicates that ZFP91 will be degraded in humans, rabbit, and the humanized cereblon mouse, but not in wild-type mice. Results in panels b and c are representative of 3 independent experiments.

Figure 2:
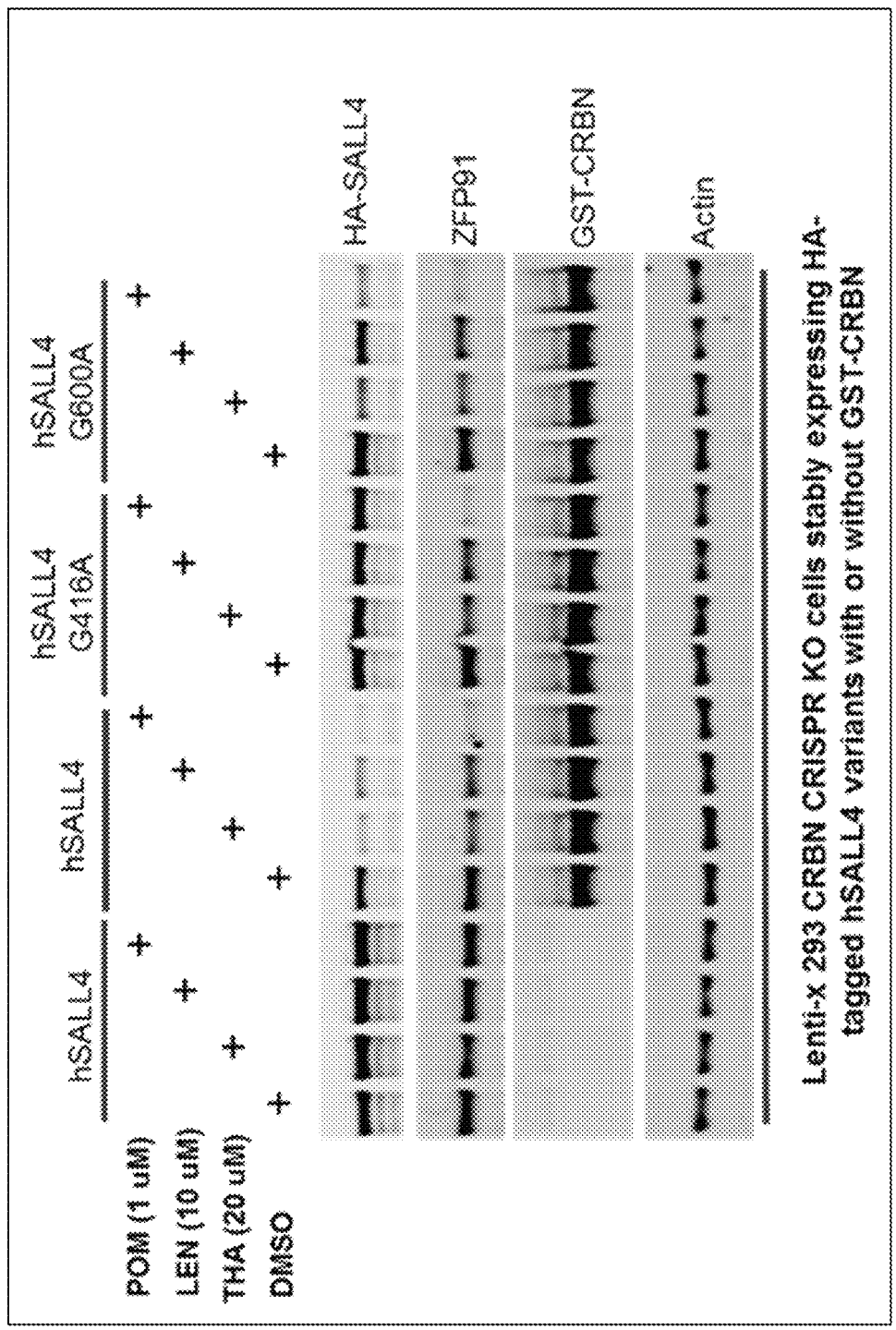

FIG. 2 shows that SALL4 degradation in cells is compound- and cereblon-dependent, and mutation of G416 to A416 disrupts this degradation of SALL4.

Figure 3:
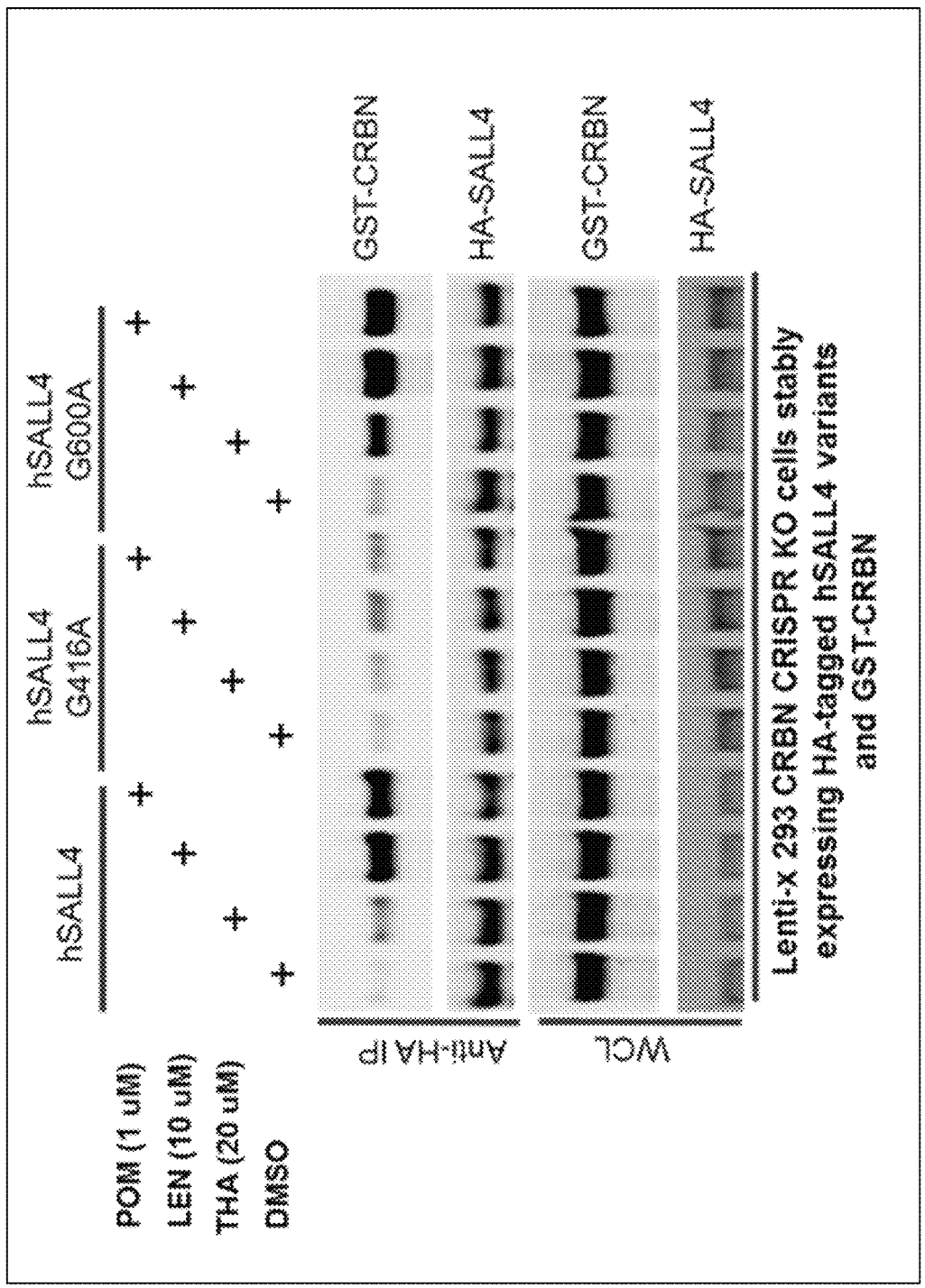

FIG. 3 shows that SALL4 binding to cereblon in cells is compound-dependent and disrupted by mutation of G416, as demonstrated by co-immunoprecipitation.

Figure 4:
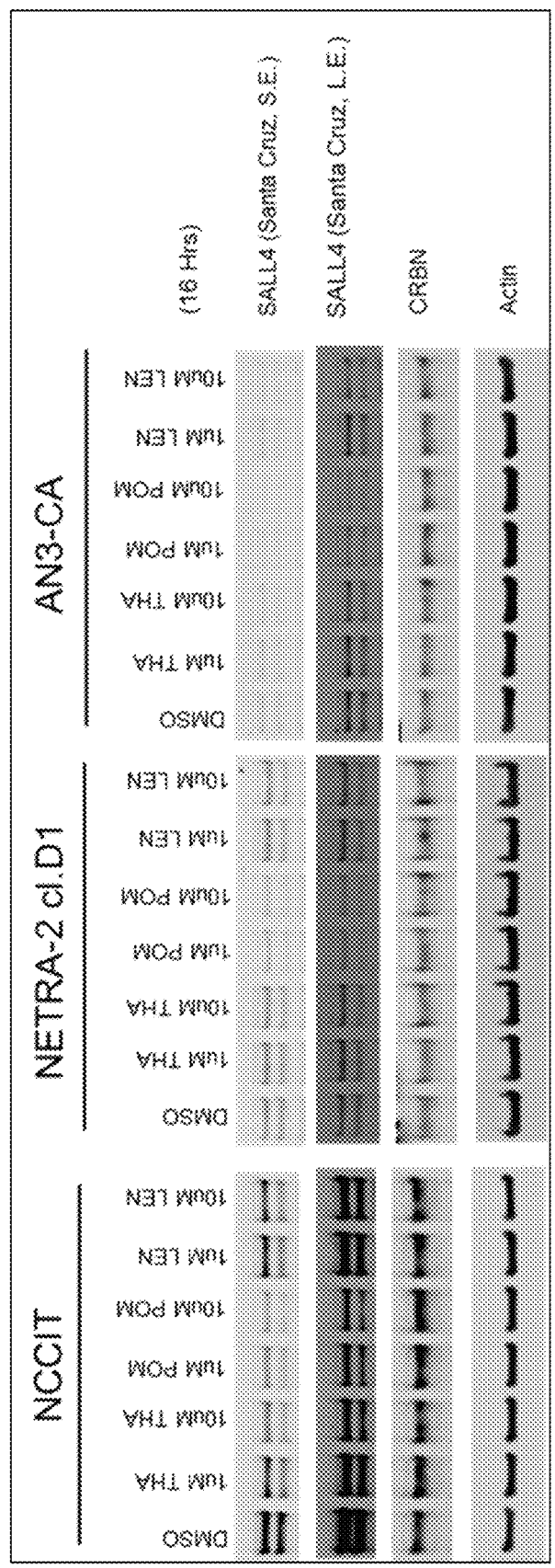

FIG. 4 shows compound-dependent degradation of endogenous SALL4 in various cancer cell lines after short or long exposure (S.E and L.E. respectively).

Figure 5:
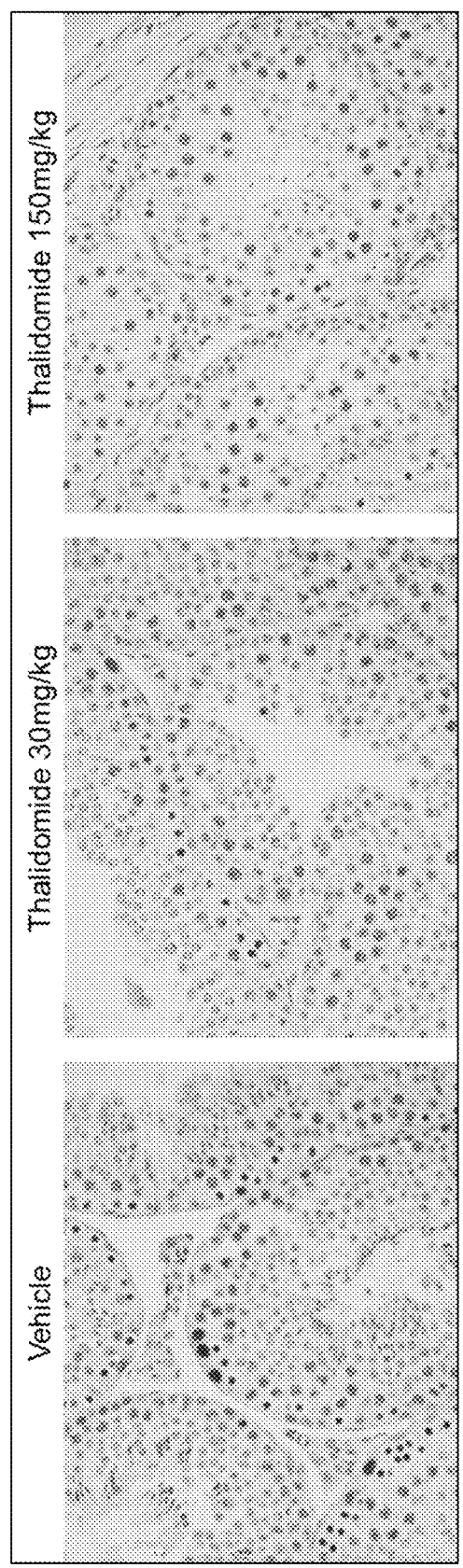

FIG. 5 shows that thalidomide causes a dose dependent decrease in SALL4 levels in rabbit testis, as indicated by SALL4 IHC staining.

Figure 6:
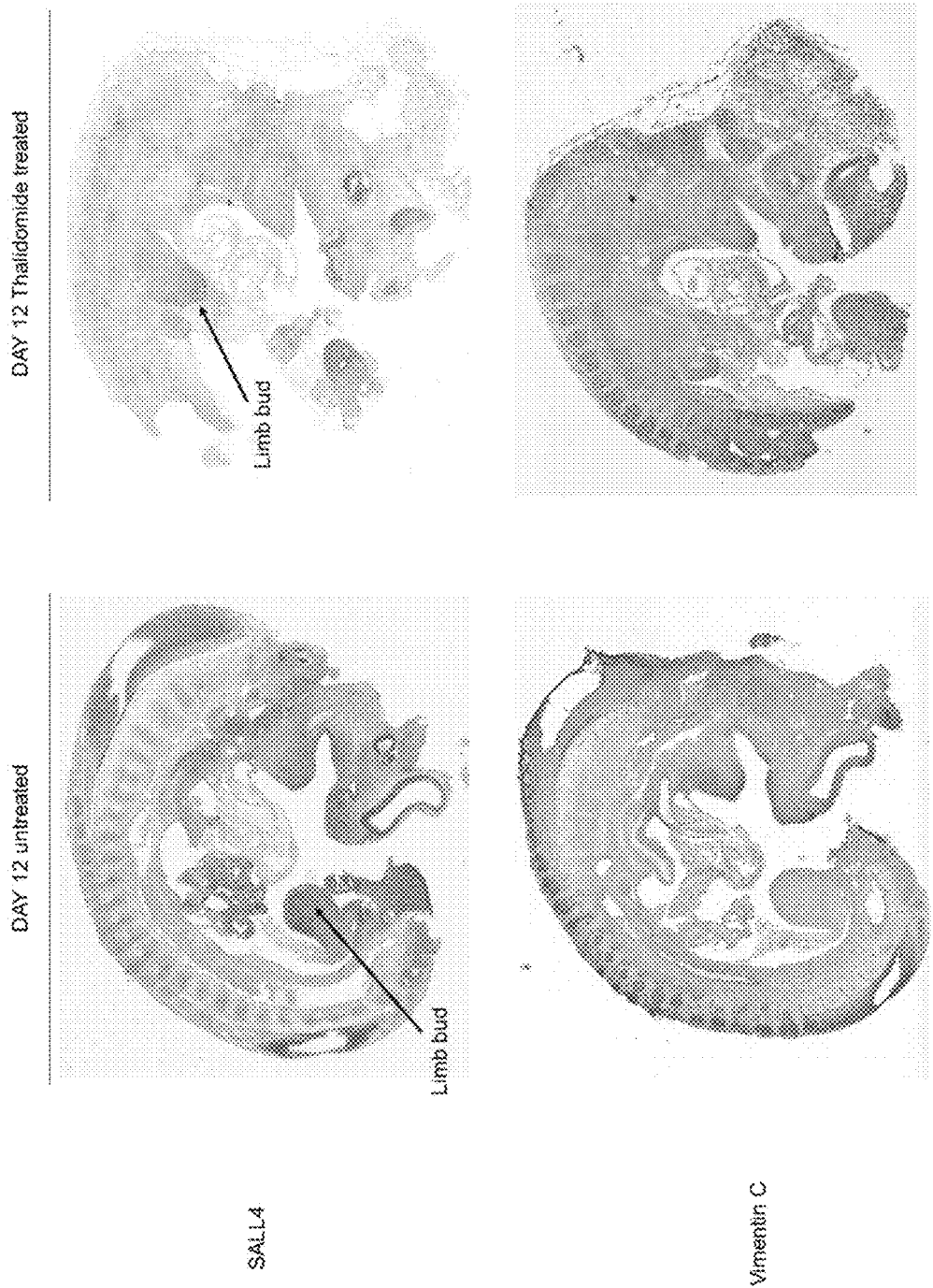

FIG. 6 shows that thalidomide causes downregulation of SALL4 levels in rabbit embryos, as indicated by SALL4 IHC staining. Pregnant female rabbits were treated with 180 mg/kg thalidomide and embryos examined 12 days after fertilization. Embryos were fixed and stained with SALL4 (top panel) and Vimentin C (bottom panel) and examined by immunohistochemistry. All tissues counterstained with hematoxylin blue. Images are representative of n=10 embryos for each group.

Figure 7A:
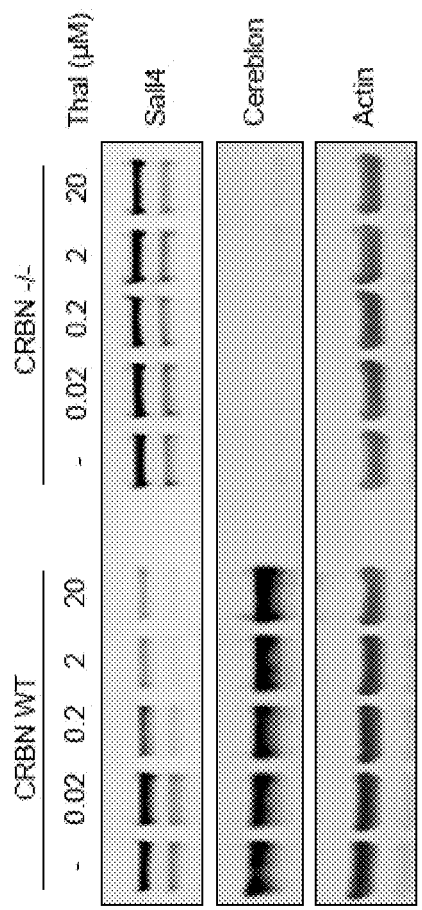

FIG. 7A shows the decrease in SALL4 protein level in iPS cells is dependent on thalidomide and cerelon. Immunoblot analysis of whole cell lysates of CRBN wild-type (WT) and CRBN knock-out (–/–) human iPS cells was performed. Cells were treated with DMSO vehicle control (–) or thalidomide (Thal) at indicated concentrations for 16 hours (n=4, biological replicates).

Figure 7B:
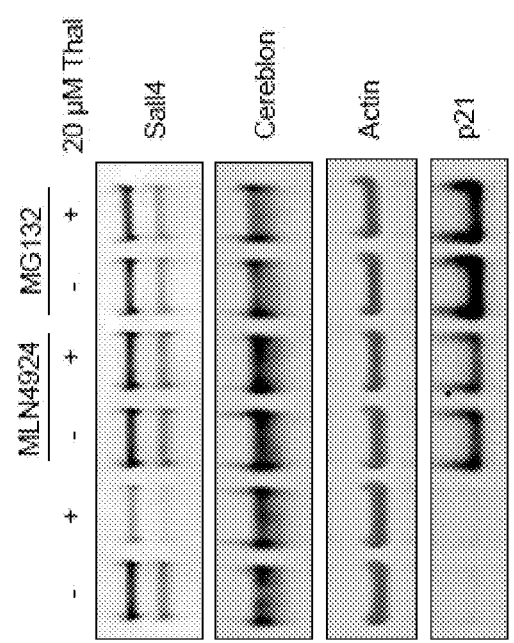

FIG. 7B shows that the thalidomide-dependent decrease in SALL4 protein levels in iPS cells is both neddylation and proteasome dependent. Immunoblot analysis of whole cell lysates of human iPS cells treated with DMSO (–) or Thal (+) in the presence or absence of 1 µM MLN4924 or 10 µM MG132 for 6 hours were performed (n=2, biological replicates).

Figures 7C, 7D:
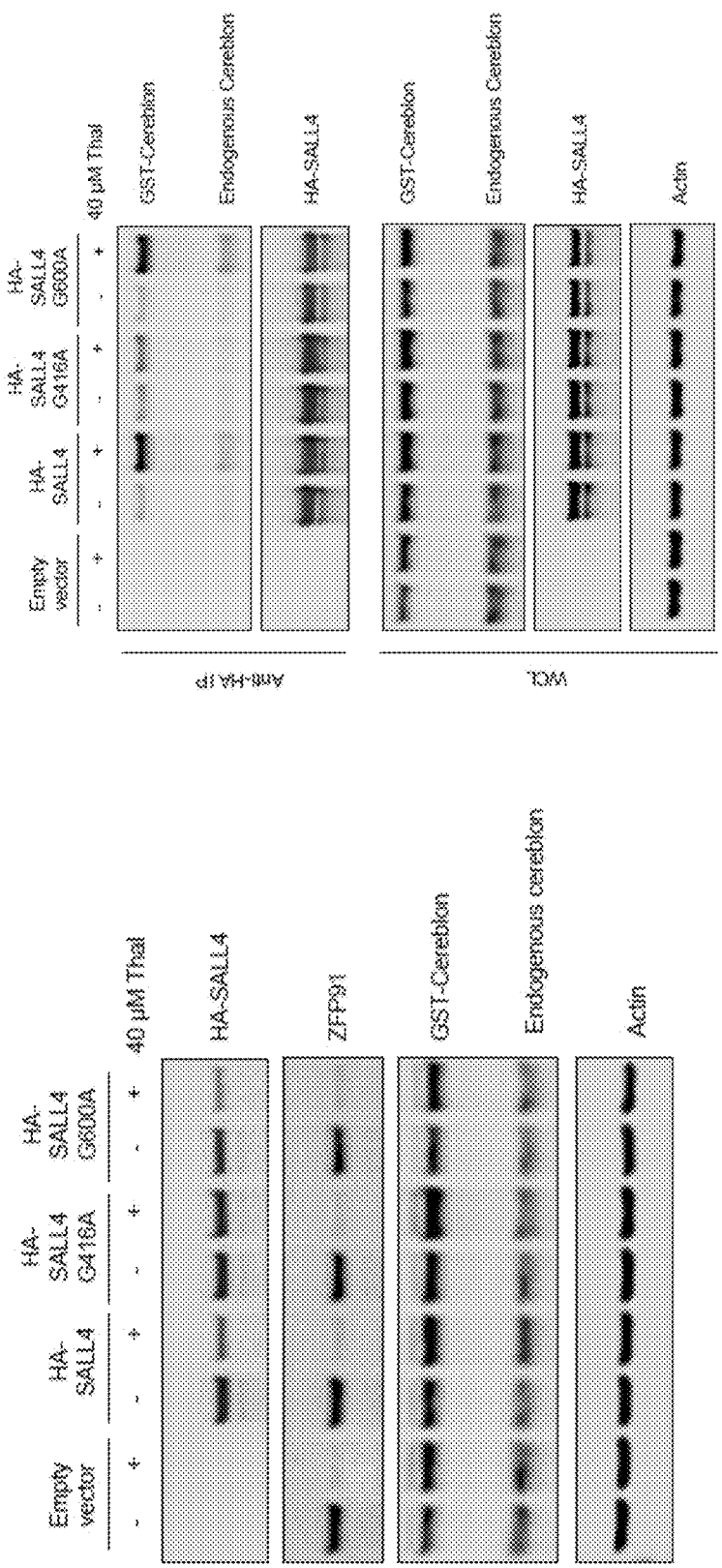

FIG. 7C shows the immunoblot analysis of whole cell lysates of lenti-X-293 HEK cells stably expressing GST-CRBN and SALL4 variants. Cells were treated with 40 µM thalidomide (+) or DMSO vehicle control (–) as indicated for 16 hours (n=2, biological replicates).

FIG. 7D shows the immunoblot analysis of anti-HA immunoprecipitates (top panel) and whole cell lysates (bottom panel) of lenti-X-293 HEK cells stably expressing GST-CRBN and SALL4 variants. All cells were treated with 1 µM MLN4924, and either 40 µM thalidomide (+) or DMSO vehicle control (–) as indicated for 8 hours (n=2 biological replicates).

Figure 7E:
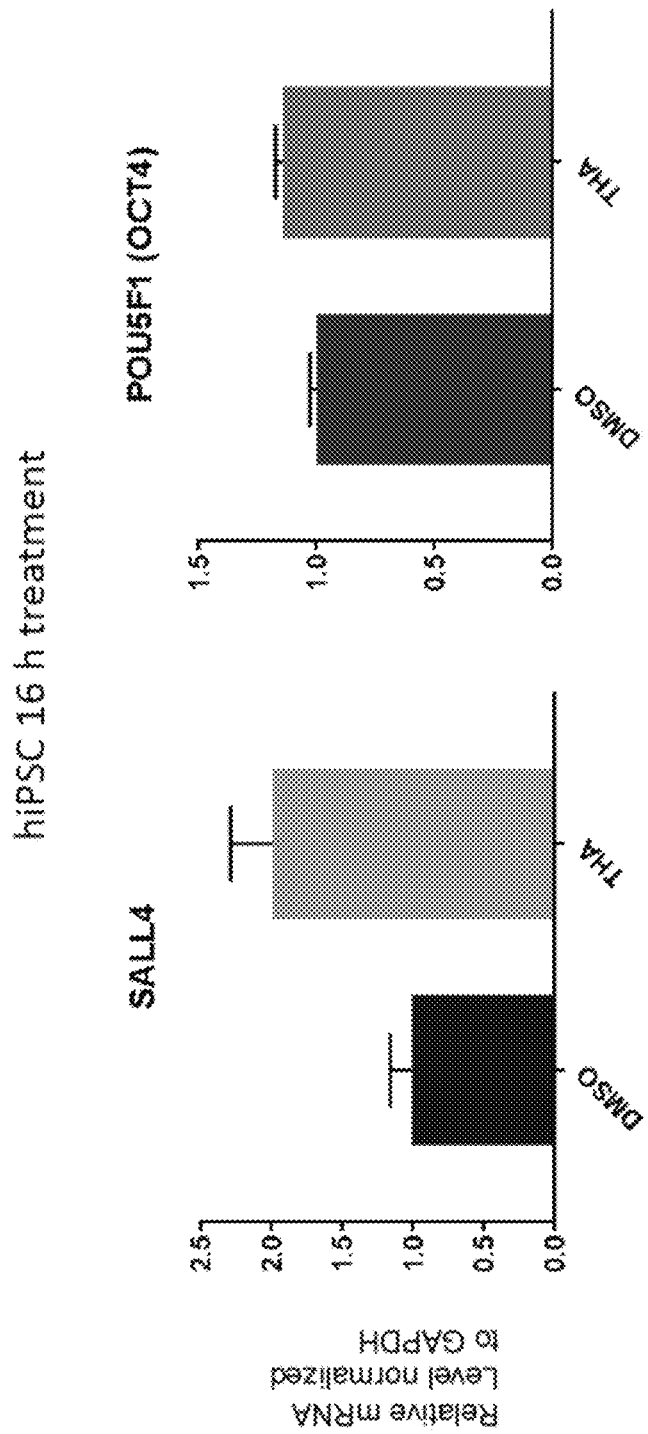

FIG. 7E shows that qRT-PCR analysis of SALL4 mRNA level in human iPS cells demonstrates decrease in SALL4 protein levels is not due to transcriptional downregulation. Quantitative RT-PCR analysis was performed to human iPS cells treated with DMSO or 20 µM thalidomide (THA) for 16 hours. The relative mRNA level of SALL4 and POU5F1 (OCT4) was normalized with GAPDH (n=2, biological replicates).

Figure 8:
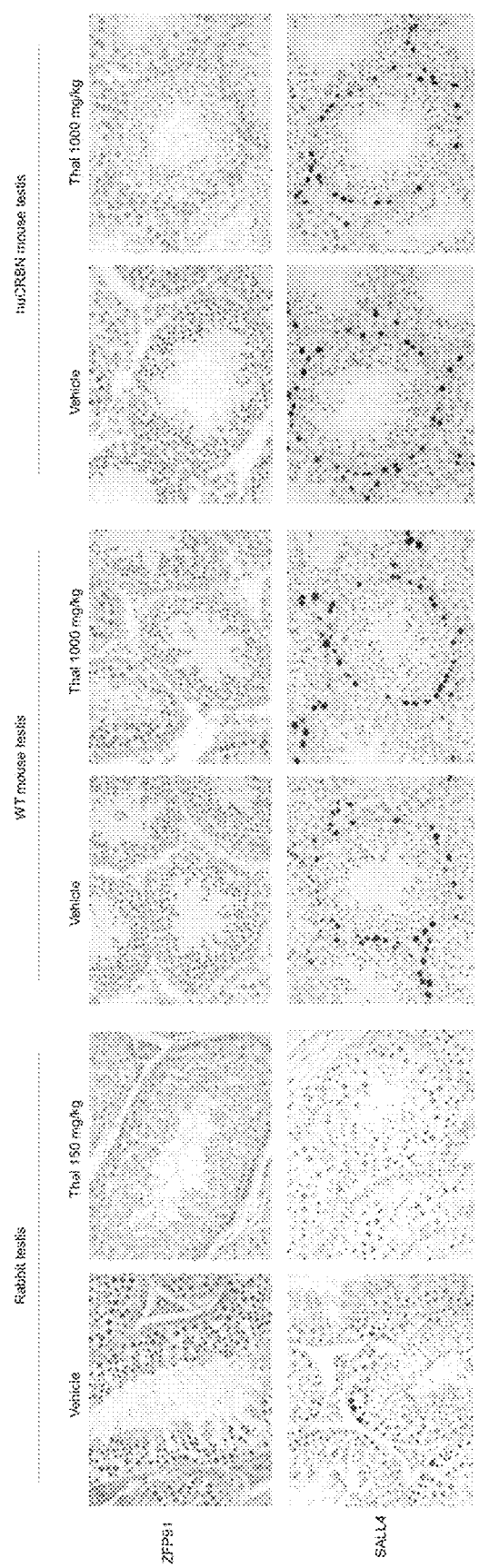

FIG. 8 shows the SALL4 protein levels decrease in vivo upon thalidomide treatment in rabbits, but not in wild-type mice or mice expressing human cereblon. The SALL4 and ZFP91 protein levels were examined by immunohistochemistry in rabbit, wild-type mouse, and humanized cereblon mouse testes. Left panels show that treatment of rabbits with 150 mg/kg thalidomide caused degradation of both ZFP91 and SALL4. Middle panels show that treatment of wild type mice with 1000 mg/kg thalidomide did not cause significant degradation of either ZFP91 or SALL4. Right panels show that treatment of huCRBN mice with 1000 mg/kg thalidomide caused degradation of ZFP91 but not SALL4. HuCRBN Mice were treated for 7 days and testis were collected and examined by immunohistochemistry (n=3 animals per treatment group per species).

Figure 9:
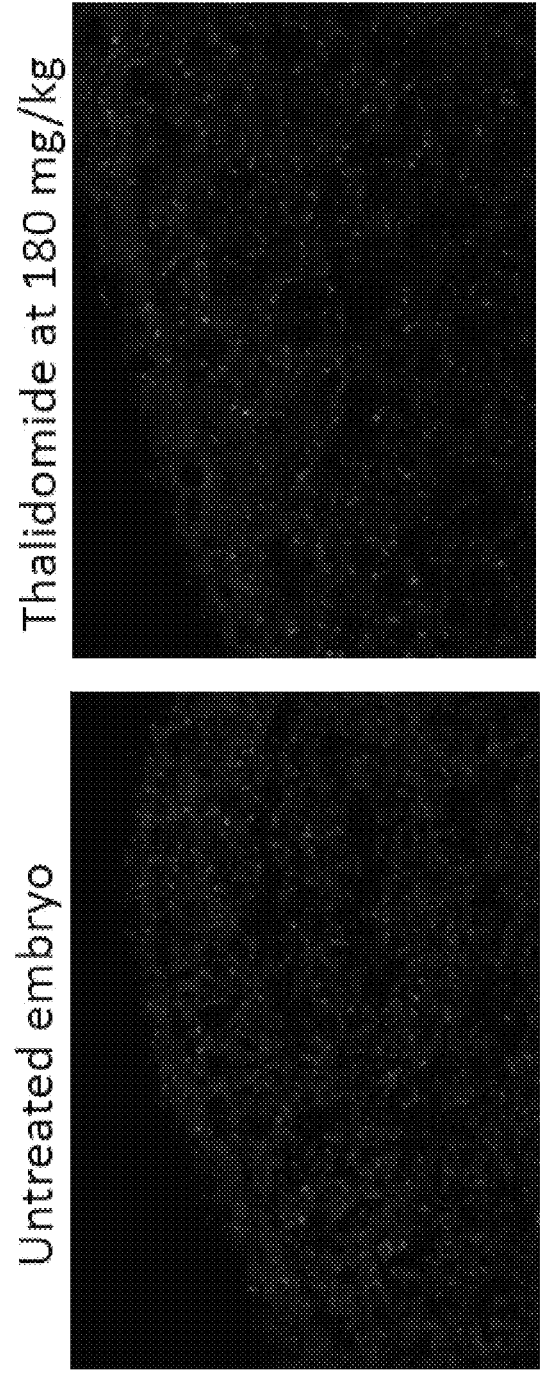

FIG. 9 shows that SALL4 mRNA levels were similar in the limb buds of untreated and thalidomide-treated rabbit embryos. SALL4 mRNA transcripts were visualized by in situ hybridization (ISH) in rabbit embryo limb buds.

Figure 10:
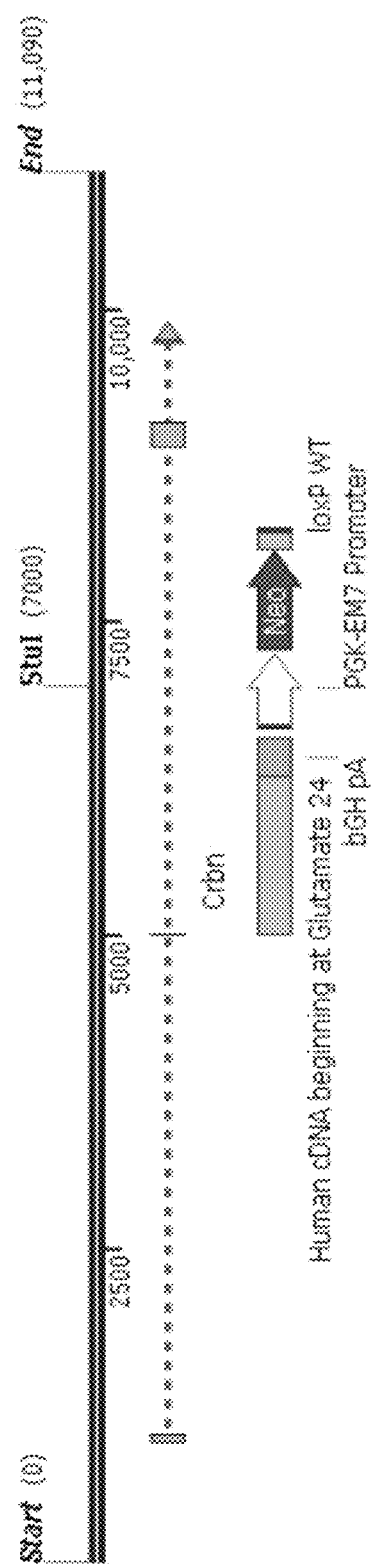

FIG. 10 shows a schematic of humanized cereblon knock-in mouse.

Figure 11:
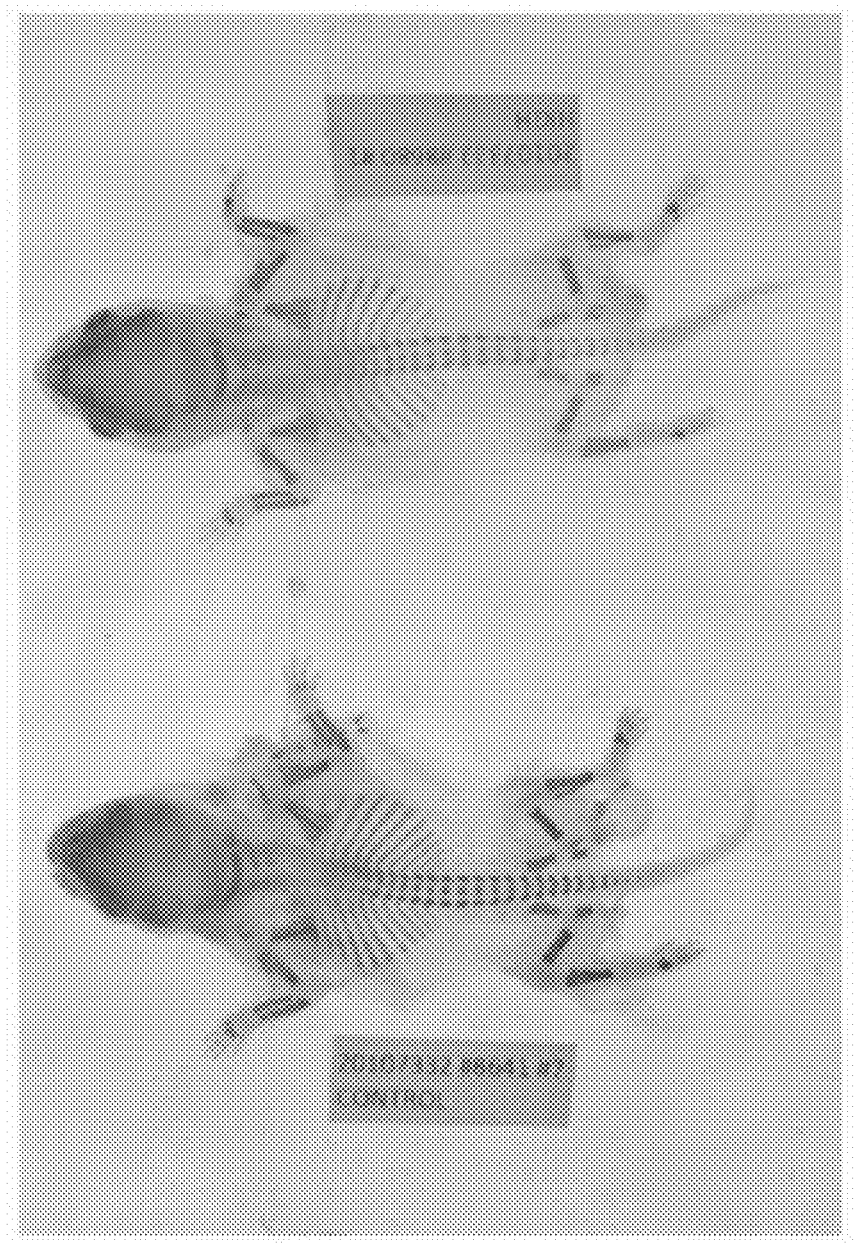

FIG. 11 shows that limb defects were not observed in huCRBN mice treated with thalidomide. Photograph of the skeleton from a vehicle treated mouse is shown on the left, and a huCRBN transgenic mouse treated with 1000 mg/kg thalidomide is shown on the right. Fetuses were prepared with alizarin red S for bone visualization.

5. DETAILED DESCRIPTION OF THE INVENTION

The methods provided herein are based, in part, on the finding that SALL4 is a direct and compound-dependent substrate of cereblon-CRL4 ubiquitination. For example, as shown in the examples in Section 6 below, SALL4 is downregulated by thalidomide treatment in rabbit testis and in rabbit embryos during development. The data presented herein indicate that SALL4 downregulation is a major driver of the teratogenic effects induced by treatment with cereblon modifying compounds such as thalidomide. Thus, SALL4 levels can be used to determine the toxicity of cereblon modifying compounds, thereby allowing for the screening and selection of compounds with reduced risk of reproductive toxicities and/or embryopathy.

5.1 Definitions

The terms "cereblon" or "CRBN" and similar terms refers to the polypeptides ("polypeptides," "peptides," and "proteins" are used interchangeably herein) comprising the amino acid sequence of any CRBN, such as a human CRBN protein (e.g., human CRBN isoform 1, GenBank Accession No. NP_057386; or human CRBN isoforms 2, GenBank Accession No. NP_001166953, each of which is herein incorporated by reference in its entirety), and related polypeptides, including SNP variants thereof. Related CRBN polypeptides include allelic variants (e.g., SNP variants), splice variants, fragments, derivatives, substitution variant, deletion variant, insertion variant, fusion polypeptides, and interspecies homologs, which, in certain embodiments, retain CRBN activity and/or are sufficient to generate an anti-CRBN immune response.

As used herein, the terms "compound" and "treatment compound" are used interchangeably. Non-limiting examples of compounds include those disclosed in Section 5.4 below. Exemplary compounds or treatment compounds of the present disclosure are cereblon modifying compounds.

The term "cereblon modifying compound" (or "CRBN modifying agent") refers to a molecule that directly or indirectly modulates the CRBN E3 ubiquitin-ligase complex. In some embodiments, the "cereblon modifying compound" can bind directly to CRBN, induce a conformational change in the CRBN protein, or result in a change in the CRBN protein surface. In other embodiments, the cereblon modifying compound can bind directly to other subunits in the CRBN E3 ubiquitin-ligase complex.

As used herein, the term "immunomodulatory compound" or "immunomodulatory drug" refers generally to a molecule or agent capable of altering the immune response in some way.

As used herein, the term "cancer" includes, but is not limited to, solid cancer and blood borne cancer. The term "cancer" refers to disease of tissues or organs, including but not limited to, cancers of the bladder, bone, blood, brain, breast, cervix, chest, colon, endrometrium, esophagus, eye, head, kidney, liver, lymph nodes, lung, mouth, neck, ovaries, pancreas, prostate, rectum, skin, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, colorectal cancer, including stage 3 and stage 4 colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

As used herein, "blood borne cancer" or "hematologic cancer" refers to cancer of the body's blood-forming and immune system—the bone marrow and lymphatic tissue. Such cancers include leukemias, lymphomas (Non-Hodgkin's Lymphoma), Hodgkin's disease (also called Hodgkin's Lymphoma) and myeloma. In one embodiment, the myeloma is multiple myeloma. In some embodiments, the leukemia is, for example, acute myelogenous leukemia (AML), acute lymphocytic leukemia (ALL), adult T-cell leukemia, chronic lymphocytic leukemia (CLL), hairy cell leukemia, myelodysplasia, myeloproliferative disorders, chronic myelogenous leukemia (CIVIL), myelodysplastic syndrome (MDS), human lymphotropic virus-type 1 (HTLV-1) leukemia, mastocytosis, or B-cell acute lymphoblastic leukemia. In some embodiments, the lymphoma is, for example, diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin lymphoma (HL), non-Hodgkin lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, or ALK-positive large B-cell lymphoma. In one embodiment, the hematological cancer is indolent lymphoma including, for example, DLBCL, follicular lymphoma, or marginal zone lymphoma. The lymphoma can be newly diagnosed, relapsed, refractory and/or resistant to conventional therapy.

The term "leukemia" refers to malignant neoplasms of the blood-forming tissues. The leukemia includes, but is not limited to, chronic lymphocytic leukemia, chronic myelocytic leukemia, acute lymphoblastic leukemia, acute myeloid leukemia, and acute myeloblastic leukemia. The leukemia can be newly diagnosed, relapsed, refractory and/or resistant to conventional therapy.

The term "myelodysplastic syndrome" refers to hematological conditions characterized by abnormalities in the production of one or more of the cellular components of blood (red cells, white cells (other than lymphocytes) and platelets (or their progenitor cells, megakaryocytes)), and includes the following disorders: refractory anemia (RA); RA with ringed sideroblasts (RARS); RA with excess of blasts (RAEB); refractory cytopenia with multilineage dysplasia (RCMD), refractory cytopenia with unilineage dysplasia (RCUD); unclassifiable myelodysplastic syndrome (MDS-U), myelodysplastic syndrome associated with an isolated del(5q) chromosome abnormality, therapy-related myeloid neoplasms and chronic myelomonocytic leukemia (CMML).

As used herein, "promyelocytic leukemia" or "acute promyelocytic leukemia" refers to a malignancy of the bone marrow in which there is a deficiency of mature blood cells in the myeloid line of cells and an excess of immature cells called promyelocytes. It is usually marked by an exchange of regions of chromosomes 15 and 17.

As used herein, "acute lymphocytic leukemia (ALL)", also known as "acute lymphoblastic leukemia" refers to a malignant disease caused by the abnormal growth and development of early nongranular white blood cells, or lymphocytes.

As used herein, "T-cell leukemia" refers to a disease in which certain cells of the lymphoid system called T lymphocytes or T cells are malignant. T cells are white blood cells that normally can attack virus-infected cells, foreign cells, and cancer cells and produce substances that regulate the immune response.

As used herein, and unless otherwise specified, the terms "treat," "treating," and "treatment" refer to an action that occurs while a patient is suffering from the specified disease or disorder, which reduces the severity of the disease or disorder, the symptoms of the disease or disorder, or retards or slows the progression of the disease or disorder. In one embodiment, the disease or disorder is cancer.

As used herein, the term "therapeutically effective amount" of a compound is an amount sufficient to provide a therapeutic benefit in the treatment or management of a disease or disorder, or to delay or minimize one or more symptoms associated with the presence of the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent. The term also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "regulate" as used herein refers to controlling the activity of a molecule or biological function, such as enhancing or diminishing the activity or function.

The terms "polypeptide" and "protein," as used interchangeably herein, refer to a polymer of three or more amino acids in a serial array, linked through peptide bonds. The term "polypeptide" includes proteins, protein fragments, protein analogues, oligopeptides, and the like. The term "polypeptide" as used herein can also refer to a peptide. The amino acids making up the polypeptide may be naturally derived, or may be synthetic. The polypeptide can be purified from a biological sample. The polypeptide, protein, or peptide also encompasses modified polypeptides, proteins, and peptides, e.g., glycopolypeptides, glycoproteins, or glycopeptides; or lipopolypeptides, lipoproteins, or lipopeptides.

The term "level" refers to the amount, accumulation, or rate of a molecule. A level can be represented, for example, by the amount or the rate of synthesis of a messenger RNA (mRNA) encoded by a gene, the amount or the rate of synthesis of a polypeptide or protein encoded by a gene, or the amount or the rate of synthesis of a biological molecule accumulated in a cell or biological fluid. In some embodiments, the term "level" refers to an absolute amount of a molecule in a sample or a relative amount of the molecule, determined under steady-state or non-steady-state conditions.

The terms "determining," "measuring," "evaluating," "assessing," and "assaying" as used herein generally refer to any form of measurement, and include determining whether an element is present or not. These terms include quantitative and/or qualitative determinations. Assessing may be relative or absolute. "Determining the presence of" can include determining the amount of something present, as well as determining whether it is present or absent.

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural nucleotides, nucleotide mimetics such as 2'-modified nucleosides, peptide nucleic acids, oligomeric nucleoside phosphonates, and any polynucleotide that has added substituent groups, such as protecting groups or linking moieties.

As used herein, the term "bind" indicates direct or indirect attachment. The term "bind" means direct physical interaction between two molecules in certain embodiments. In the context of chemical structures, "bind" may refer to the existence of a chemical bond directly joining two moieties or indirectly joining two moieties (e.g., via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bind" includes embodiments where the attachment is direct and embodiments where the attachment is indirect. As used herein, "bind to cereblon" includes both binding directly to cereblon and binding to other subunits in the CRBN E3 ubiquitin-ligase complex.

The term "sample" as used herein relates to a material or mixture of materials, typically, although not necessarily, in fluid form, containing one or more components of interest. A sample can be a "biological sample," which refers to a sample obtained from a biological subject, including a sample of biological tissue or fluid origin, obtained or collected in vivo or in situ. A biological sample also includes samples from a region of a biological subject containing diseased cells or tissues, for example precancerous or cancer cells or tissues. Such samples can be, but are not limited to, organs, tissues, and cells isolated from a mammal. Other exemplary samples include but are not limited to a cell lysate, a cell culture, a cell line, an isolated protein (including in complexes), a synthetic protein (including in complexes), a cell extract, an engineered cell (for example, a genetically modified or transfected cell), a bacterial cell (for example *E. coli* cell), an insect cell (for example, a *spodoptera frugiperda* cell), a fetal cell, a fetal tissue, a zebrafish, a tissue, an oral tissue, a gastrointestinal tissue, an organ, an organelle, a biological fluid, a blood sample, a urine sample, a skin sample, a bone marrow sample, a circulating tumor cell, a tumor cell, and the like, and combinations of one or more thereof.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like. Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts (calcium, magnesium, sodium, or potassium salts in particular). Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "solvate" means a compound provided herein or a salt thereof that further includes a stoichiometric or non-stoichiometric amount of solvent bound by non-covalent intermolecular forces. Where the solvent is water, the solvate is a hydrate.

As used herein and unless otherwise indicated, the term "co-crystal" means a crystalline form that contains more than one compound in a crystal lattice. Co-crystals include crystalline molecular complexes of two or more non-volatile compounds bound together in a crystal lattice through non-ionic interactions. As used herein, co-crystals include pharmaceutical co-crystals wherein the crystalline molecular complexes containing a therapeutic compound and one or more additional non-volatile compound(s) (referred to herein as counter-molecule(s)). A counter-molecule in a pharmaceutical co-crystal is typically a non-toxic pharmaceutically acceptable molecule, such as, for example, food additives, preservatives, pharmaceutical excipients, or other active pharmaceutical ingredients (API). In some embodiments, pharmaceutical co-crystals enhance certain physicochemical properties of drug products (e.g., solubility, dissolution rate, bioavailability, and/or stability) without compromising the chemical structural integrity of the API. See, e.g., Jones et al., *MRS Bulletin* 2006, 31,875-879; Trask, *Mol. Pharmaceutics* 2007, 4(3):301-309; Schultheiss & Newman, *Crystal Growth & Design* 2009, 9(6):2950-2967; Shan & Zaworotko, *Drug Discovery Today* 2008, 13(9/10):440-446; and Vishweshwar et al., *J. Pharm. Sci.* 2006, 95(3):499-516.

As used herein, and unless otherwise specified, the term "stereoisomer" encompasses all enantiomerically/stereomerically pure and enantiomerically/stereomerically enriched compounds of this invention.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

As used herein, and unless otherwise specified, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise —NO, —$NO_2$, —ONO, or —$ONO_2$ moieties. Prodrugs can typically be prepared using well-known methods, such as those described in *Burger's Medicinal Chemistry and Drug Discovery*, 172-178, 949-982 (Manfred E. Wolff, ed., 5th ed. 1995), and *Design of Prodrugs* (H. Bundgaard, ed., Elsevier, New York 1985).

It should also be noted that compounds can contain unnatural proportions of atomic isotopes at one or more of the atoms. For example, the compounds may be radiolabeled with radioactive isotopes, such as for example tritium ($^3H$), iodine-125 ($^{125}I$) sulfur-35 ($^{35}S$), or carbon-14 ($^{14}C$), or may be isotopically enriched, such as with deuterium ($^2H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds, for example, the isotopologues are deuterium, carbon-13, or nitrogen-15 enriched compounds. In some embodiments, isotopologues provided herein are deuterium enriched compounds. In some embodiments, isotopologues provided herein are deuterium enriched compounds, where the deuteration occurs on the chiral center. In some embodiments, provided herein are isotopologues of the compounds provided herein, where deuteration occurs on the chiral center. In some embodiments, provided herein are isotopologues of Compound C, where deuteration occurs on the chiral center.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein, the terms "subject" and "patient" are used interchangeably. As used herein, a subject can be a mammal such as a non-primate (e.g., cows, pigs, horses, cats, dogs, rats, etc.) or a primate (e.g., monkey and human). In specific embodiments, the subject is a human. In one embodiment, the subject is a mammal (e.g., a human) having a disease, disorder or condition. In another embodiment, the subject is a mammal (e.g., a human) at risk of developing a disease, disorder or condition.

As used herein, "selecting" and "selected" in reference to a compound is used to mean that a particular compound is specifically chosen from a group of compounds on the basis of (due to) the particular compound having a predetermined criteria. A compound can be selected by screening libraries or collection of compounds.

It should be noted that if there is a discrepancy between a depicted structure and a name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al., *Molecular Cloning: A Laboratory Manual* (2d ed. 1989); Glover, ed., *DNA Cloning*, Volumes I and II (1985); Gait, ed., *Oligonucleotide Synthesis* (1984); Hames & Higgins, eds., *Nucleic Acid Hybridization* (1984); Hames & Higgins, eds., *Transcription and Translation* (1984); Freshney, ed., *Animal Cell Culture: Immobilized Cells and Enzymes* (IRL Press, 1986); *Immunochemical Methods in Cell and Molecular Biology* (Academic Press, London); Scopes, *Protein Purification: Principles and Practice* (Springer Verlag, N.Y., 2d ed. 1987); and Weir & Blackwell, eds., *Handbook of Experimental Immunology*, Volumes I-IV (1986).

5.2 Methods for Characterizing or Selecting a Compound

Sal-like protein 4 (SALL4) is a transcription factor encoded by a member of the Spalt-like (SALL) gene family, SALL4. SALL4 expression begins early in development, as early as the 7 or 8-cell stage in mice (Elling et al., *PNAS*, 103 (44):16319-16324 (2006); Koshiba-Takeuchi et al., *Nat Genetics*, 38: 175-183 (2006)), and persists through the blastocyst or longer in certain stem cell types, like the testis of adult humans and other mammals (Eildermann et al., *Cells Tissues Organs*, 196(3):206-20 (2012); Gassei et al., Plos One, 8(1):e53976 (2013)).

SALL4 is an embryonic transcription factor that controls limb morphogenesis. A reduced functional SALL4 protein level during development has been shown to be the cause of several human syndromes that are characterized by limb malformations. In humans, loss-of-function mutations in SALL4 cause Okihiro (also known as Duane Radial Ray), IVIC (also known as Oculootoradial), Holt-Oram, and Acrorenal-ocular syndromes, all characterized by forearm abnormalities, along with varying degrees of ear, eye, heart, and kidney defects (Borozdin et al., *J Med Genet*, 41: e113 (2004); Borozdin et al., *J Med Genetics*, 41:e102 (2004); Kholase et al., *Human Mutat.*, 26(3):176-83 (2005); Al-Baradie et al., *Am J Hum Genet.*, 71: 1195-1199 (2002);

Kohlase et al., *J Med Genet.*, 40(7):473-8 (2003); and Kohlase et al., *Birth Defects Res A Clin Mot Teratol.*, 70(8):550-1 (2004)). The SALL4 mutations associated with these syndromes are autosomal dominant, and predicted to cause reduced SALL4 activity (Borozdin et al., *J Med Genet*, 41: e113 (2004); Koshiba-Takeuchi et al., *Nat Genetics*, 38: 175-183 (2006)). Therefore, it is indicated that halploinsufficiency of SALL4 is the pathogenic mechanism, and that even small reduction in Sall4 protein level may be expected to cause developmental abnormalities.

There are at least two isoforms of SALL4—SALL4A and SALL4B. The methods provided herein are based, in part, on the discovery that SALL4A is a direct, compound-dependent substrate of cereblon-CRL4 ubiquitination. The examples in Section 6 below demonstrate that SALL4A is a direct and compound-induced target of cereblon-CRL4 ubiquitination in vitro and in vivo.

Thus, the data disclosed in the present application identify SALL4 (or SALL4A) degradation as a driver of cereblon modifying compound-induced teratogenicity. The level of SALL4 can be used to determine the toxicity of cereblon modifying compounds, thereby allowing for the screening and selection of cereblon modifying compounds with reduced risk of reproductive toxicities. More specifically, the cereblon modifying compounds that do not induce or result in significantly reduced degradation of SALL4 may be preferable for treating certain patients as such compounds may have reduced risk of reproductive toxicities.

As used herein, the term "SALL4" refers to isoform A or SALL4A. The amino acid sequences of human SALL4A (identifier: Q9UJQ4-1) is as follows:

```
                                              (SEQ ID NO: 1)
MSRRKQAKPQ HINSEEDQGE QQPQQQTPEF ADAAPAAPAA

GELGAPVNHP GNDEVASEDE ATVKRLRREE THVCEKCCAE

FFSISEFLEH KKNCTKNPPV LIMNDSEGPV PSEDFSGAVL

SHQPTSPGSK DCHRENGGSS EDMKEKPDAE SVVYLKTETA
```

```
-continued
LPPTPQDISY LAKGKVANTN VTLQALRGTK VAVNQRSADA

LPAPVPGANS IPWVLEQILC LQQQQLQQIQ LTEQIRIQVN

MWASHALHSS GAGADTLKTL GSHMSQQVSA AVALLSQKAG

SQGLSLDALK QAKLPHANIP SATSSLSPGL APFTLKPDGT

RVLPNVMSRL PSALLPQAPG SVLFQSPFST VALDTSKKGK

GKPPNISAVD VKPKDEAALY KHKCKYCSKV FGTDSSLQIH

LRSHTGERPF VCSVCGHRFT TKGNLKVHFH RHPQVKANPQ

LFAEFQDKVA AGNGIPYALS VPDPIDEPSL SLDSKPVLVT

TSVGLPQNLS SGTNPKDLTG GSLPGDLQPG PSPESEGGPT

LPGVGPNYNS PRAGGFQGSG TPEPGSETLK LQQLVENIDK

ATTDPNECLI CHRVLSCQSS LKMHYRTHTG ERPFQCKICG

RAFSTKGNLK THLGVHRTNT SIKTQHSCPI CQKKFTNAVM

LQQHIRMHMG GQIPNTPLPE NPCDFTGSEP MTVGENGSTG

AICHDDVIES IDVEEVSSQE APSSSSKVPT PLPSIHSASP

TLGFAMMASL DAPGKVGPAP FNLQRQGSRE NGSVESDGLT

NDSSSLMGDQ EYQSRSPDIL ETTSFQALSP ANSQAESIKS

KSPDAGSKAE SSENSRTEME GRSSLPSTFI RAPPTYVKVE

VPGTFVGPST LSPGMTPLLA AQPRRQAKQH GCTRCGKNFS

SASALQIHER THTGEKPFVC NICGRAFTTK GNLKVHYMTH

GANNNSARRG RKLAIENTMA LLGTDGKRVS EIFPKEILAP

SVNVDPVVWN QYTSMLNGGL AVKTNEISVI QSGGVPTLPV

SLGATSVVNN ATVSKMDGSQ SGISADVEKP SATDGVPKHQ

FPHFLEENKI AVS.
```

The coding sequence of human SALL4A is as follows:

```
                                              (SEQ ID NO: 2)
  1 atgtcgaggc gcaagcaggc gaaacccag cacatcaact cggaggagga ccagggcgag 61 cagcagccgc agcagcagac cccggagttt gcagatgcgg ccccagcggc gcccgcggcg 121 ggggagctgg gtgctccagt gaaccaccca gggaatgacg aggtggcgag tgaggatgaa 181 gccacagtaa agcggcttcg tcgggaggag acgcacgtct gtgagaaatg ctgtgcggag 241 ttcttcagca tctctgagtt cctggaacat aagaaaaatt gcactaaaaa tccacctgtc 301 ctcatcatga tgacagcga ggggcctgtg ccttcagaag acttctccgg agctgtactg 361 agccaccagc ccaccagtcc cggcagtaag gactgtcaca gggagaatgg cggcagctca 421 gaggacatga aggagaagcc ggatgcggag tctgtggtgt acctaaagac agagacagcc 481 ctgccaccca ccccccagga cataagctat ttagccaaag gcaaagtggc caacactaat 541 gtgaccttgc aggcactacg gggcaccaag gtgcggtga atcagcggag cgcggatgca 601 ctccctgccc ccgtgcctgg tgccaacagc atcccgtggg tcctcgagca gatcttgtgt 661 ctgcagcagc agcagctaca gcagatccag ctcaccgagc agatccgcat ccaggtgaac 721 atgtgggcct cccacgccct ccactcaagc ggggcagggg ccgacactct gaagaccttg 781 ggcagccaca tgtctcagca ggtttctgca gctgtggctt tgctcagcca gaaagctgga 841 agccaaggtc tgtctctgga tgccttgaaa caagccaagc tacctcacgc caacatccct
```

-continued

```
 901 tctgccacca gctccctgtc cccagggctg gcacccttca ctctgaagcc ggatgggacc 961 cgggtgctcc cgaacgtcat gtcccgcctc ccgagcgctt tgcttcctca ggccccgggc 1021 tcggtgctct tccagagccc tttctccact gtggcgctag acacatccaa gaaagggaag 1081 gggaagccac cgaacatctc cgcggtggat gtcaaaccca agacgaggc ggccctctac 1141 aagcacaagt gtaagtactg tagcaaggtt tttgggactg atagctcctt gcagatccac 1201 ctccgctccc acactggaga gagacccttc gtgtgctctg tctgtggtca tcgcttcacc 1261 accaagggca acctcaaggt gcactttcac cgacatcccc aggtgaaggc aaaccccag 1321 ctgtttgccg agttccagga caaagtggcg gccggcaatg gcatccccta tgcactctct 1381 gtacctgacc ccatagatga accgagtctt tctttagaca gcaaacctgt ccttgtaacc 1441 acctctgtag ggctacctca gaatctttct tcggggacta atcccaagga cctcacgggt 1501 ggctccttgc ccggtgacct gcagcctggg ccttctccag aaagtgaggg tggacccaca 1561 ctccctgggg tgggaccaaa ctataattcc ccaagggctg gtggcttcca agggagtggg 1621 acccctgagc cagggtcaga gaccctgaaa ttgcagcagt tggtggagaa cattgacaag 1681 gccaccactg atcccaacga atgtctcatt tgccaccgag tcttaagctg tcagagctcc 1741 ctcaagatgc attatcgcac ccacaccggg gagagaccgt tccagtgtaa gatctgtggc 1801 cgagccttt ctaccaaagg taacctgaag acacaccttg ggttcaccg aaccaacaca 1861 tccattaaga cgcagcattc gtgccccatc tgccagaaga agttcactaa tgccgtgatg 1921 ctgcagcaac atattcggat gcacatgggc ggtcagattc ccaacacgcc cctgccagag 1981 aatccctgtg actttacggg ttctgagcca atgaccgtgg gtgagaacgg cagcaccggc 2041 gctatctgcc atgatgatgt catcgaaagc atcgatgtag aggaagtcag ctcccaggag 2101 gctcccagca gctcctccaa ggtccccacg cctcttccca gcatccactc ggcatcaccc 2161 acgctagggt tgccatgat ggcttcctta gatgccccag ggaaagtggg tcctgcccct 2221 tttaacctgc agcgccaggg cagcagagaa acggttccg tggagagcga tggcttgacc 2281 aacgactcat cctcgctgat gggagaccag gagtatcaga gccgaagccc agatatcctg 2341 gaaaccacat ccttccaggc actctccccg gccaatagtc aagccgaaag catcaagtca 2401 aagtctcccg atgctgggag caaagcagag agctccgaga cagccgcac tgagatggaa 2461 ggtcggagca gtctcccttc cacgtttatc cgagccccgc cgacctatgt caaggttgaa 2521 gttcctggca catttgtggg accctcgaca ttgtccccag gatgaccc tttgttagca 2581 gcccagccac gccgacaggc caagcaacat ggctgcacac ggtgtgggaa gaacttctcg 2641 tctgctagcg ctcttcagat ccacgagcgg actcacactg gagagaagcc ttttgtgtgc 2701 aacatttgtg ggcgagcttt taccaccaaa ggcaacttaa aggttcacta catgacacac 2761 ggggcgaaca ataactcagc ccgccgtgga aggaagttgg ccatcgagaa caccatggct 2821 ctgttaggta cggacggaaa aagagtctca gaaatctttc caaggaaat cctggcccct 2881 tcagtgaatg tggaccctgt tgtgtggaac cagtacacca gcatgctcaa tggcggtctg 2941 gccgtgaaga ccaatgagat ctctgtgatc cagagtgggg gggttcctac cctcccggtt 3001 tccttggggg ccacctccgt tgtgaataac gccactgtct ccaagatgga tggctcccag 3061 tcgggtatca gtgcagatgt ggaaaaacca agtgctactg acggcgttcc caaacaccag 3121 tttcctcact tcctggaaga aaacaagatt gcggtcagct aa.
```

In one aspect, the methods provided herein are based on determining the degradation of SALL4 protein.

In some embodiments, provided herein is a method comprising: (a) administering a cereblon modifying compound to a sample; and (b) determining if the compound induces degradation of SALL4 protein in the sample.

In some embodiments, the method provided herein is for screening a collection of cereblon modifying compounds (or cerblon modifying treatment compounds) to identify the cereblon modifying compound with reduced risk of teratogenic effects. In other embodiments, the method provided herein is for characterizing a cereblon modifying compound, and more specifically, for determining if a cereblon modifying compound (or cereblon modifying treatment compound) can induce teratogenic effects.

Thus, in certain embodiments, provided herein is a method of screening a cereblon modifying compound for treating a disease or disorder, comprising: (a) obtaining a sample; (b) determining a first protein level of SALL4 in the sample; (c) administering the cereblon modifying compound to the sample; (d) determining a second protein level of SALL4 in the sample; (e) comparing the first level and the second protein level of SALL4 to determine if the cereblon modifying compound induces degradation of SALL4; and (f) selecting the cereblon modifying compound that does not induce degradation of SALL4 or the cereblon modifying compound that induces reduced degradation of SALL4 as compared with a reference compound.

In certain embodiments, provided herein is a method of screening a cereblon modifying compound for treating a disease or disorder, comprising: (a) obtaining a sample; (b) determining a first protein level of SALL4 in the sample; (c) administering the compound to the sample; (d) determining a second protein level of SALL4 in the sample; (e) comparing the first level and the second protein level of SALL4 to determine if the compound induces degradation of SALL4; and (f) selecting the compound that does not induce degradation of SALL4.

In other embodiments, provided herein is a method of screening a cereblon modifying compound for treating a disease or disorder, comprising: (a) obtaining a sample; (b) determining a first protein level of SALL4 in the sample; (c) administering the compound to the sample; (d) determining a second protein level of SALL4 in the sample; (e) comparing the first level and the second protein level of SALL4 to determine if the compound induces degradation of SALL4; and (f) selecting the compound that shows reduced degradation of SALL4. In one embodiment, the SALL4 degradation is reduced compared to the SALL4 degradation by thalidomide. In other embodiments, the reference compound is pomalidomide. In yet other embodiments, the reference compound is lenalidomide. In a specific embodiment, the SALL4 degradation is reduced compared to the SALL4 degradation by thalidomide.

In certain embodiments, provided herein is a method of determining if a cereblon modifying compound induces a teratogenic effect, comprising: (a) obtaining a sample; (b) determining a first protein level of SALL4 in the sample; (c) administering the cereblon modifying compound to the sample; (d) determining a second protein level of SALL4 in the sample; (e) comparing the first level and the second protein level of SALL4 to determine the teratogenicity of the compound.

In certain embodiments, provided herein is a method of determining if a cereblon modifying compound induces a teratogenic effect, comprising: (a) obtaining a sample; (b) determining a first protein level of SALL4 in the sample; (c) administering the compound to the sample; (d) determining a second protein level of SALL4 in the sample; (e) comparing the first level and the second protein level of SALL4 to determine if the compound induces degradation of SALL4; thereby determining the teratogenicity of the compound.

In another aspect, the methods provided herein are based on determining the level of ubiquitination of SALL4.

In certain embodiments, provided herein is a method of screening a cereblon modifying compound for treating a disease or disorder, comprising: (a) administering the cereblon modifying compound to a sample; (b) determining the level of ubiquitination of SALL4 in the sample; (c) selecting the cereblon compound that does not induce ubiquitination of SALL4 or the cereblon modifying compound that induces reduced level of ubiquitination of SALL4 as compared with a reference compound.

In some embodiments, provided herein is a method of screening a cereblon modifying compound for treating a disease or disorder, comprising: (a) administering the compound to a sample; (b) determining the level of ubiquitination of SALL4 in the sample; (c) selecting the compound that does not induce ubiquitination of SALL4.

In other embodiments, provided herein is a method of screening a cereblon modifying compound for treating a disease or disorder, comprising: (a) administering the compound to a sample; (b) determining the level of ubiquitination of SALL4 in the sample; (c) selecting the compound that shows reduced levels of ubiquitination of SALL4. In one embodiment, the SALL4 ubiquitination is reduced compared to the SALL4 ubiquitination by a reference compound. In one embodiment, the reference compound is thalidomide. In other embodiments, the reference compound is pomalidomide. In yet other embodiments, the reference compound is lenalidomide. In a specific embodiment, the SALL4 ubiquitination is reduced compared to the SALL4 ubiquitination by thalidomide.

In some embodiments, provided herein is a method of determining if a cereblon modifying compound induces a teratogenic effect, comprising: (a) administering the compound to a sample; (b) determining the level of ubiquitination of SALL4 in the sample, thereby determining the teratogenicity of the compound. Ubiquitination of SALL4 induced by a compound indicates the potential for teratogenicity. In some embodiments a higher degree of ubiquitination of SALL4 indicates that the compound is more likely to induce a teratogenic effect.

In yet another aspect, the methods provided herein are based on determining the interaction (or binding) between SALL4 and cereblon.

Cereblon has been identified as a key molecular target that binds to certain cereblon modifying compounds, e.g., thalidomide, pomalidomide, and lenalidomide. These compounds target cereblon, and alter the substrate specificity of the ubiquitin ligase, driving the clinical activity in certain cancer cells. Bound substrates are ubiquitinated by the cereblon-CRL4 complex, leading to their degradation by the 26S proteasome. Thus, degradation of SALL4 can also be determined by analyzing the interaction (or binding) between SALL4 and cereblon upon treatment with a cereblon modifying compound, and/or ubiquitination of SALL4 upon treatment with a cereblon modifying compound.

In certain embodiments, provided herein is a method of screening a cereblon modifying compound for treating a disease or disorder, comprising: (a) administering the cereblon modifying compound to a sample; (b) determining the interaction between SALL4 and cereblon; (c) selecting the cereblon modifying compound that does not induce the interaction between SALL4 and cereblon or the cereblon modifying compound that induces reduced interaction between SALL4 and cereblon as compared with a reference compound.

In some embodiments, provided herein is a method of screening a cereblon modifying compound for treating a disease or disorder, comprising: (a) administering the compound to a sample; (b) determining the interaction between SALL4 and cereblon in the sample; (c) selecting the compound that does not induce the interaction between SALL4 and cereblon.

In other embodiments, provided herein is a method of screening a cereblon modifying compound for treating a disease or disorder, comprising: (a) administering the compound to a sample; (b) determining the interaction between SALL4 and cereblon; (c) selecting the compound that results in reduced interaction between SALL4 and cereblon. In one embodiment, the interaction between SALL4 and cereblon is reduced compared to the interaction between SALL4 and cereblon in the presence of a reference compound. In one embodiment, the reference compound is thalidomide. In other embodiments, the reference compound is pomalidomide. In yet other embodiments, the reference compound is lenalidomide. In a specific embodiment, the interaction between SALL4 and cereblon is reduced compared to the SALL4 and cereblon interaction in the presence of thalidomide.

In certain embodiments, provided herein is a method of determining if a cereblon modifying compound induces a teratogenic effect, comprising: (a) administering the cereblon modifying compound to a sample; (b) determining the interaction between SALL4 and cereblon, thereby determining the teratogenicity of the compound.

In yet other embodiments, provided herein is a method of determining if a cereblon modifying compound induces a teratogenic effect, comprising: (a) administering the compound to a sample; (b) determining the interaction between SALL4 and cereblon, wherein the interaction between SALL4 and CRBN indicates the potential for teratogenicity. In certain embodiments, determining the interaction between SALL4 and cereblon includes determining the physical interaction or binding between SALL4 and cereblon.

As shown in the examples of Section 6 below, the present disclosure identifies the amino acid residues 405-432 of SALL4 protein (SEQ ID NO: 3) or a fragment thereof (e.g., amino acid residues 410-432 of SALL4 protein (SEQ ID NO: 11)) as at least a portion of the SALL4 protein that is directly involved in binding to cereblon in the presence of the cereblon modifying compound; and demonstrates that mutations within this region (e.g., G416A) are likely to disrupt the interaction between cereblon and SALL4 upon treatment with a compound. Therefore, the interaction between amino acid residues 405-432 of SALL4 protein (SEQ ID NO: 3) or a fragment thereof (e.g., amino acid residues 410-432 of SALL4 protein (SEQ ID NO: 11)) and cereblon in the presence of cereblon modifying compound can be used to determine if SALL4 can be degraded by treatment with a cereblon modifying compound. In certain embodiments, an amino acid fragment comprising amino acid residues 405-432 of the SALL4 protein is used. In certain embodiments, an amino acid fragment comprising amino acid residues 410-432 of the SALL4 protein is used.

In certain assays, one or more amino acids within amino acid residues 405-432 of the SALL4 protein or a fragment thereof (e.g., amino acid residues 410-432 of SALL4 protein) are analyzed with respect to their binding to certain amino acids of cereblon in the presence of a cereblon modifying compound. In some embodiment, the amino acid analyzed is G416. In other embodiments, the amino acid is T405. In other embodiments, the amino acid is G406. In other embodiments, the amino acid is E407. In other embodiments, the amino acid is R408. In other embodiments, the amino acid is P409. In other embodiments, the amino acid is F410. In other embodiments, the amino acid is V411. In other embodiments, the amino acid is C412. In other embodiments, the amino acid is S413. In other embodiments, the amino acid is V414. In other embodiments, the amino acid is H417. In other embodiments, the amino acid is R418. In other embodiments, the amino acid is F419. In other embodiments, the amino acid is T420. In other embodiments, the amino acid is T421. In other embodiments, the amino acid is K422. In other embodiments, the amino acid is G423. In other embodiments, the amino acid is N424. In other embodiments, the amino acid is L425. In yet other embodiments, the amino acid is K426. In yet other embodiments, the amino acid is V427. In yet other embodiments, the amino acid is H428. In yet other embodiments, the amino acid is F429. In yet other embodiments, the amino acid is H430. In yet other embodiments, the amino acid is R431. In yet other embodiments, the amino acid is H432.

In some embodiments of the various methods provided herein, determination of protein degradation can be performed by any conventional methods known to those skilled in the art. In some embodiments of the various methods provided herein, whether the cereblon modifying compound induces the degradation of SALL4 is determined by comparing the protein level of SALL4 after administration of the cereblon modifying compound to a reference level. The reference can be prepared by using a control sample, and the control sample is from the same source as the sample. In other embodiments of the various methods provided herein, the reference level is determined by measuring the protein level of SALL4 in the sample prior to the administration of the cereblon modifying compound. In some embodiments, the reference level is a pre-determined level. In some embodiments, the reference level is the SALL4 level in the presence of reference cereblon modifying compound, for example thalidomide, lenalidomide or pomalidomide.

In some embodiments, the method provided herein further comprises determining the first protein level of SALL4 prior to the administration of the cereblon modifying compound to the sample, determining the second protein level of SALL4 after the administration of the cereblon modifying compound to the sample, comparing the first level to the second protein level, and determining if the second level is not significantly lower than the first level (which indicates that the compound does not induce the degradation of the SALL4 protein).

In some embodiments of the methods provided herein, administering the cereblon modifying treatment compound to the sample is performed in vitro. In other embodiments, administering the cereblon modifying treatment compound to the sample is performed in vivo. In one embodiment, the samples are contacted with the compound for a period of time, e.g., 5, 10, 15, 20, 25, 30, 35, 40, 45, 50, or 55 minutes, or 1, 2, 3, 4, 5, 6, 7, 8, 9, 10, 11, 12, 13, 14, 15, 16, 17, 18, 19, 20, 21, 22, 23, or 24 hours, or 2, 3, 4, 5, 6, 7, 10, 20, or more days.

In some embodiments, the sample provided here may be a sample of biological tissue or fluid origin, obtained, or collected in vivo or in situ. In some embodiments, the sample may be obtained from a region of a patient containing diseased cells or tissues, for example, precancerous or cancer cells or tissues, for example a tumor. Such samples can be, but are not limited to, organs, tissues, and cells isolated from the patient. Exemplary samples include but are not limited to cell lysate, a cell culture, a tissue, oral tissue, gastrointestinal tissue, an organ, an organelle, a biological fluid, a blood sample, a urine sample, a skin sample, a bone marrow sample, circulating tumor cells, and the like. In other embodiments, the sample provided herein may be a sample selected from a cell lysate, a cell culture, a cell line, an isolated protein, a synthetic protein, a cell extract, an engineered cell, a bacterial cell, an insect cell, a fetal cell, a fetal tissue, a zebrafish, and the like, and combinations of one or more thereof.

In certain embodiments, the various methods provided herein use samples (e.g., biological samples) from subjects or individuals (e.g., patients). The subject can be a patient, such as, a patient with a cancer (e.g., lymphoma, MM, or leukemia). The subject can be a mammal, for example, a human. The subject can be male or female, and can be an adult, a child, an infant, or a fetus. Samples can be analyzed at a time during an active phase of a cancer (e.g., lymphoma, MM, or leukemia), or when the cancer (e.g., lymphoma, MM, or leukemia) is inactive. In certain embodiments, more than one sample from a subject can be obtained.

In certain embodiments, the sample used in the methods provided herein comprises body fluids from a subject. Non-limiting examples of body fluids include blood (e.g., whole blood), blood plasma, amniotic fluid, aqueous humor, bile, cerumen, cowper's fluid, pre-ejaculatory fluid, chyle, chyme, female ejaculate, interstitial fluid, lymph, menses, breast milk, mucus, pleural fluid, pus, saliva, sebum, semen, serum, sweat, tears, urine, vaginal lubrication, vomit, water, feces, internal body fluids (including cerebrospinal fluid surrounding the brain and the spinal cord), synovial fluid, intracellular fluid (the fluid inside cells), and vitreous humour (the fluid in the eyeball). In some embodiments, the sample is a blood sample. The blood sample can be obtained using conventional techniques as described in, e.g., Innis et al, eds., *PCR Protocols* (Academic Press, 1990). White blood cells can be separated from blood samples using conventional techniques or commercially available kits, e.g., RosetteSep kit (Stein Cell Technologies, Vancouver, Canada). Sub-populations of white blood cells, e.g., mono-nuclear cells, B cells, T cells, monocytes, granulocytes, or lymphocytes, can be further isolated using conventional techniques, e.g., magnetically activated cell sorting (MACS) (Miltenyi Biotec, Auburn, Calif.) or fluorescently activated cell sorting (FACS) (Becton Dickinson, San Jose, Calif.).

In one embodiment, the blood sample is from about 0.1 mL to about 10.0 mL, from about 0.2 mL to about 7 mL, from about 0.3 mL to about 5 mL, from about 0.4 mL to about 3.5 mL, or from about 0.5 mL to about 3 mL. In another embodiment, the blood sample is about 0.3, about 0.4, about 0.5, about 0.6, about 0.7, about 0.8, about 0.9, about 1.0, about 1.5, about 2.0, about 2.5, about 3.0, about 3.5, about 4.0, about 4.5, about 5.0, about 6.0, about 7.0, about 8.0, about 9.0, or about 10.0 ml.

In some embodiments, the sample used in the present methods comprises a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a sample from a subject, for instance, open biopsy, close biopsy, core biopsy, incisional biopsy, excisional biopsy, or fine needle aspiration biopsy.

In one embodiment, the sample used in the methods provided herein is obtained from the subject prior to the subject receiving a treatment for the disease or disorder. In another embodiment, the sample is obtained from the subject during the subject receiving a treatment for the disease or disorder. In another embodiment, the sample is obtained from the subject after the subject receiving a treatment for the disease or disorder. In various embodiments, the treatment comprises administering a cereblon modifying compound provided herein to the subject.

In certain embodiments, the sample used in the methods provided herein comprises a plurality of cells, such as cancer (e.g., lymphoma, MM, or leukemia) cells. Such cells can include any type of cells, e.g., stem cells, blood cells (e.g., peripheral blood mononuclear cells (PBMC)), lymphocytes, B cells, T cells, monocytes, granulocytes, immune cells, or cancer cells.

B cells (B lymphocytes) include, for example, plasma B cells, memory B cells, B1 cells, B2 cells, marginal-zone B cells, and follicular B cells. B cells can express immunoglobulins (antibodies) and B cell receptor.

Specific cell populations can be obtained using a combination of commercially available antibodies (e.g., antibodies from Quest Diagnostic (San Juan Capistrano, Calif.) or Dako (Denmark)).

In certain embodiments, the cells in the methods provided herein are PBMC. In certain embodiments, the sample used in the methods provided herein is from a disease tissue, e.g., from an individual having cancer (e.g., lymphoma, MM, or leukemia).

In certain embodiments, samples from cell lines are used as disease models for evaluating effects of compounds, studying mechanisms of action, or establishing reference levels, etc. In some embodiments, the cells used in the methods provided herein are from a cancer cell line.

For example, in some embodiments, leukemia cell lines are used as samples. For example, in one embodiment, AML cell lines are used as samples. In one embodiment, the AML cell line is KG-1 cell line. In another embodiment, the AML cell line is KG-1a cell line. In yet another embodiment, the AML cell line is KASUMI-1 cell line. In still another embodiment, the AML cell line is NB4 cell line. In one embodiment, the AML cell line is MV-4-11 cell line. In another embodiment, the AML cell line is MOLM-13 cell line. In yet another embodiment, the AML cell line is HL-60 cell line. In still another embodiment, the AML cell line is U-937 cell line. In one embodiment, the AML cell line is OCI-AML2 cell line. In another embodiment, the AML cell line is OCI-AML3 cell line. In yet another embodiment, the AML cell line is HNT-34 cell line. In still another embodiment, the AML cell line is ML-2 cell line. In one embodiment, the AML cell line is AML-193 cell line. In another embodiment, the AML cell line is F36-P cell line. Other exemplary leukemia cell lines include but not limited to 8E5 cell line, CCRF-CEM cell line, CCRF-HSB-2 cell line, MOLT-3 cell line, CEM/C2 cell line, CEM/C1 cell line, TALL-104 cell line, THP-1 cell line, Kasumi-3 cell line, BDCM cell line, NCI-BL2122 cell line, JAA-F11 cell line, 31E9 cell line, RBL-2H3 cell line, MV-4-11 cell line, BCP-1 cell line, JVM-13 cell line, KU812 cell line, MYA-1 cell line, Mo-B cell line, MM.1S cell line, RBL-1 cell line, and WEHI-3 cell line.

For another example, lymphoma and blood cell lines are used as samples. Exemplary cell lines include but not limited to Daudi cell line, GA-10 cell line, HCC38BL cell line, HCC2218BL cell line, HH cell line, Toledo cell line, FeT-J cell line, NK-92 cell line, Mino cell line, JVM-2 cell line, EML-3C cell line, D34 cell line, 63D3 cell line, C1R-B7 cell line, OKT5 cell line, and 1H3 cell line.

In other embodiments, bladder cancer cell lines, such as HT-1376 cell line, SCaBER cell line, T24 cell line, RT4 cell line, TMB-54 cell line, and HT1197.T cell line are used as samples.

In other embodiments, bone cancer cell lines, such as SUP-B15 cell line, Hs 696 cell line, K-562 cell line, MEG-01 cell line, TF-1 cell line, RD-ES cell line, SAML-2 cell line, FDC-P1 cell line, D-17 cell line, HOS cell line, UMR-106 cell line, SK-ES-1 cell line, KM703 cell line, and BBm cell line, are used as samples.

In other embodiments, brain cancer cell lines, such as SW1088 cell line, CHLA-02-ATRT cell line, U-118 MG cell line, HCN-2 cell line, RG2 cell line, LN-229 cell line, C6 cell line, 3G5 cell line, M059K cell line, X22 cell line, SCP cell line, OA1 cell line, and NE-GFP-4C cell line, are used as samples.

In yet other embodiments, breast cancer cell lines, such as Hs 281.T cell line, MDA-MB-468 cell line, CAMA-1 cell line, SK-BR-3 cell line, RBA cell line, UACC-1179 cell line, NMU cell line, BT-483 cell line, T-47D cell line, ZR-75-30 cell line, MCF10A cell line, and EMT6 cell line, are used as samples.

In yet other embodiments, colon cancer cell lines such as RKO are used as samples. In yet other embodiments, gynecological cancer cell lines such as HeLa 229 are used as samples. In yet other embodiments, head and neck cancer cell lines such as FaDu are used as samples. In yet other embodiments, liver cancer cell lines such as Capan-1 are used as samples. In yet other embodiments, lung cancer cell lines such as Calu-3 are used as samples. In yet other embodiments, pancreatic cancer cell lines such HPAC are used as samples. In yet other embodiments, sarcoma cell lines such as SK-LMS-1 are used as samples. Cell lines from other cancer models are also included in the present disclosure.

In certain embodiments, the number of cells used in the methods provided herein can range from a single cell to about $10^9$ cells. In some embodiments, the number of cells used in the methods provided herein is about $1\times10^4$, about $5\times10^4$, about $1\times10^5$, about $5\times10^5$, about $1\times10^6$, about $5\times10^6$, about $1\times10^7$, about $5\times10^7$, about $1\times10^8$, about $5\times10^8$, or about $1\times10^9$.

The number and type of cells can be monitored, for example, by measuring changes in cell surface markers using standard cell detection techniques such as flow cytometry, cell sorting, immunocytochemistry (e.g., staining with tissue specific or cell-marker specific antibodies), fluorescence activated cell sorting (FACS), magnetic activated cell sorting (MACS), by examining the morphology of cells using light or confocal microscopy, and/or by measuring changes in gene expression using techniques well known in the art, such as PCR and gene expression profiling. These techniques can be used, too, to identify cells that are positive for one or more particular markers.

In certain embodiments, subsets of cells are used in the methods provided herein. Methods of sorting and isolating specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimentation, affinity adsorption, affinity extraction, density gradient centrifugation, laser capture microdissection, etc. Fluorescence activated cell sorting (FACS) is a well-known method for separating particles, including cells, based on the fluorescent properties of the particles (Kamarch, *Methods Enzymol.* 151:150-165 (1987)). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

The level of SALL4 protein can be determined using the methods known to those skilled in the art.

In certain embodiments, provided herein are methods of detecting and quantifying the protein level of SALL4, from a sample, for example, a biological sample.

Several protein detection and quantization methods can be used to measure the level of SALL4. Any suitable protein quantization method can be used. In some embodiments, antibody-based methods are used. Exemplary methods that can be used include, but are not limited to, immunoblotting (Western blot), point of care techniques/platforms, ELISA, immunohistochemistry, flow cytometry, cytometry bead array, mass spectroscopy, chromatography, such as high performance liquid chromatography (HPLC), and the like. Several types of ELISA are commonly used, including direct ELISA, indirect ELISA, and sandwich ELISA.

For detection of protein levels, there are numerous well-known method for detecting polypeptide products in a sample, e.g., by means of a probe (e.g., a binding protein, e.g., an antibody capable of interacting specifically with SALL4). Labeled antibodies, binding portions thereof, or other binding partners can be used. The antibodies can be monoclonal or polyclonal in origin, or may be biosynthetically produced. The binding partners may also be naturally occurring molecules or synthetically produced. The amount of complexed proteins is determined using standard protein detection methodologies described in the art. A detailed review of immunological assay design, theory and protocols can be found in numerous texts in the art, including *Practical Immunology*, Butt, W. R., ed., Marcel Dekker, New York, 1984.

A variety of immunohistochemistry assays are available for detecting proteins with labeled antibodies. Direct labels include fluorescent or luminescent tags, metals, dyes, radionucleides, and the like, attached to the antibody. Indirect labels include various enzymes well known in the art, such as alkaline phosphatase, hydrogen peroxidase and the like. In a one-step assay, the target protein SALL4 is immobilized and incubated with a labeled antibody. The labeled antibody binds to the immobilized target molecule. After washing to remove unbound molecules, the sample is assayed for the presence of the label. Numerous immunohistochemical methods are incorporated into point-of-care formats and hand-helds, all of which may be used for determining levels of protein.

The use of immobilized antibodies specific for the proteins or polypeptides is also contemplated by the present disclosure. The antibodies can be immobilized onto a variety of solid supports, such as magnetic or chromatographic matrix particles, the surface of an assay place (such as microtiter wells), pieces of a solid substrate material (such as plastic, nylon, paper), and the like. An assay strip can be prepared by coating the antibody or a plurality of antibodies in an array on solid support. This strip can then be dipped into the test sample and processed through washes and detection steps to generate a measurable signal, e.g., a colored spot.

In a two-step assay, an immobilized target protein SALL4 may be incubated with an unlabeled antibody. The unlabeled antibody complex, if present, is then bound to a second, labeled antibody that is specific for the unlabeled antibody. The sample is washed and assayed for the presence of the label. The choice of marker used to label the antibodies will vary depending upon the application. However, the choice of the marker is readily determinable to one skilled in the art.

The antibodies may be labeled with a radioactive atom, an enzyme, a chromophoric or fluorescent moiety, or a colorimetric tag. The choice of tagging label also will depend on the detection limitations desired. Enzyme assay's (ELISAs) typically allow detection of a colored product formed by interaction of the enzyme-tagged complex with an enzyme substrate. Some examples of radioactive atoms include 32P, 125I, 3H, and 14P. Some examples of enzymes include horseradish peroxidase, alkaline phosphatase, beta-galactosidase, and glucose-6-phosphate dehydrogenase. Some examples of chromophoric moieties include fluorescein and rhodamine. The antibodies may be conjugated to these labels by methods known in the art. For example, enzymes and chromophoric molecules may be conjugated to the antibodies by means of coupling agents, such as dialdehydes, carbodiimides, dimaleimides, and the like. Alternatively, conjugation may occur through a ligand-receptor pair. Some suitable ligand-receptor pairs include, e.g., biotin-avidin or -streptavidin, and antibody-antigen.

In one aspect, the present disclosure contemplates the use of a sandwich technique for detecting the level of a target protein SALL4 in biological samples. The technique requires two antibodies capable of binding the protein of interest: e.g., one immobilized onto a solid support and one free in solution, but labeled with some easily detectable chemical compound. Examples of chemical labels that may be used for the second antibody include but are not limited to radioisotopes, fluorescent compounds, and enzymes or other molecules which generate colored or electrochemically active products when exposed to a reactant or enzyme substrate. When samples containing SALL4 protein are placed in this system, the polypeptide binds to both the immobilized antibody and the labeled antibody. The result is a "sandwich" immune complex on the support's surface. The complexed protein is detected by washing away nonbound sample components and excess labeled antibody, and measuring the amount of labeled antibody complexed to protein on the support's surface. A sandwich immunoassay is highly specific and very sensitive when labels with good limits of detection are used.

Dot blotting is routinely practiced by the skilled artisan to detect a desired protein using an antibody as a probe (*Promega Protocols and Applications Guide*, Second Edition, 1991, Page 263, Promega Corporation). Samples are applied to a membrane using a dot blot apparatus. A labeled probe is incubated with the membrane, and the presence of the protein is detected. Western blot analysis is well known to the skilled artisan (Sambrook et al., *Molecular Cloning, A Laboratory Manual,* 1989, Vol. 3, Chapter 18, Cold Spring Harbor Laboratory). In Western blot, the sample is separated by SDS-PAGE. The gel is transferred to a membrane. The membrane is incubated with labeled antibody for detection of the desired protein.

The assays described above involve steps such as, but not limited to, immunoblotting, immunodiffusion, immunoelectrophoresis, or immunoprecipitation. Specific immunological binding of the antibody to the protein or polypeptide can be detected directly or indirectly. In some embodiments, an automatic analyzer (e.g., an automatic sequencing machine) is used to determine the level of SALL4. All such methods are well known by skilled artisans.

In some embodiments, the level or the presence of SALL4 protein is analyzed and/or determined by mass spectrometry (MS). Typically, mass spectrometry (MS) analysis of proteins measures the mass-to-charge ratio of ions to identify and quantify molecules in simple and complex mixtures. Mass spectrometers have an ion source, a mass analyzer and an ion detector. The nature of these components varies based on the purpose of the mass spectrometer, the type of data required, and the physical properties of the sample. Samples are loaded into the mass spectrometer in liquid, gas or dried form and then vaporized and ionized by the ion source (e.g., APCI, DART, ESI). The charge that these molecules receive allows the mass spectrometer to accelerate the ions throughout the remainder of the system. The ions encounter electric and/or magnetic fields from mass analyzers, which deflect the paths of individual ions based on their m/z. Commonly used mass analyzers include time-of-flight [TOF], orbitraps, quadrupoles and ion traps, and each type has specific characteristics. Mass analyzers can be used to separate all analytes in a sample for global analysis, or they can be used like a filter to deflect only specific ions towards the detector. Ions that have successfully been deflected by the mass analyzers then hit the ion detector. Most often, these detectors are electron multipliers or microchannel plates that emit a cascade of electrons when each ion hits the detector plate. This cascade results in amplification of each ion hit for improved sensitivity. This entire process is performed under an extreme vacuum to remove gas molecules and neutral and contaminating non-sample ions, which can collide with sample ions and alter their paths or produce non-specific reaction products. Mass spectrometers are typically connected to computer-based software platforms that measure ion oscillation frequencies and acquire mass spectra using image current detection. Data analysis programs detect ions and organize them by their individual m/z values and relative abundance. These ions can then be identified via established databases that predict the identity of the molecule based on its m/z value.

In certain embodiments, provided herein are methods of detecting and quantifying the RNA (e.g., mRNA) level of SALL4 from a sample, for example, a biological sample.

Several methods of detecting or quantitating mRNA levels are known in the art. Exemplary methods include, but are not limited to, northern blots, ribonuclease protection assays, PCR-based methods, and the like. The mRNA sequence can be used to prepare a probe that is at least partially complementary to the mRNA sequence. The probe can then be used to detect the mRNA in a sample, using any suitable assay, such as PCR-based methods, northern blotting, a dipstick assay, and the like.

In other embodiments, a nucleic acid assay in a sample, for example a biological sample, can be prepared. An assay typically contains a solid support and at least one nucleic acid contacting the support, where the nucleic acid corresponds to at least a portion of an mRNA that has altered expression during a compound treatment in a patient. The assay can also have a means for detecting the altered expression of the mRNA in the sample.

The assay method can be varied depending on the type of mRNA information desired. Exemplary methods include but are not limited to Northern blots and PCR-based methods (e.g., qRT-PCR). Methods such as qRT-PCR can also accurately quantitate the amount of the mRNA in a sample.

Any suitable assay platform can be used to determine the presence of mRNA in a sample. For example, an assay may be in the form of a dipstick, a membrane, a chip, a disk, a test strip, a filter, a microsphere, a slide, a multi-well plate, or an optical fiber. An assay system may have a solid support on which a nucleic acid corresponding to the mRNA is attached. The solid support may comprise, for example, a plastic, silicon, a metal, a resin, glass, a membrane, a particle, a precipitate, a gel, a polymer, a sheet, a sphere, a polysaccharide, a capillary, a film, a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.). See, e.g., Ausubel et al., *Short Protocols in Molecular Biology* (Wiley & Sons, 3rd ed. 1995); Sambrook et al., *Molecular Cloning: A Laboratory Manual* (Cold Spring Harbor, N.Y., 3rd ed. 2001). In some embodiments, the sample is labeled with fluorescent label. Exemplary fluorescent dyes include, but are not limited to, xanthene dyes, fluorescein dyes (e.g., fluorescein isothiocyanate (FITC), 6-carboxyfluorescein (FAM), 6 carboxy-2',4',7',4,7-hexachlorofluorescein (HEX), 6-carboxy-4',5'-dichloro-2',7'-dimethoxyfluorescein (JOE)), rhodamine dyes (e.g., rhodamine 110 (R110), N,N,N',N'-tetramethyl-6-carboxyrhodamine (TAMRA), 6-carboxy-X-rhodamine (ROX), 5-carboxyrhodamine 6G (R6G5 or G5), 6-carboxyrhodamine 6G (R6G6 or G6)), cyanine dyes (e.g., Cy3, Cy5 and Cy7), Alexa dyes (e.g., Alexa-fluor-555), coumarin, Diethylaminocoumarin, umbelliferone, benzimide dyes (e.g., Hoechst 33258), phenanthridine dyes (e.g., Texas Red), ethidium dyes, acridine dyes, carbazole dyes, phenoxazine dyes, porphyrin dyes, polymethine dyes, BODIPY dyes, quinoline dyes, Pyrene, Fluorescein Chlorotriazinyl, eosin dyes, Tetramethylrhodamine, Lissamine, Napthofluorescein, and the like.

A typical mRNA assay method can contain the steps of 1) obtaining surface-bound subject probes; 2) hybridizing a population of mRNAs to the surface-bound probes under conditions sufficient to provide for specific binding; (3) post-hybridization washing to remove nucleic acids not specifically bound to the surface-bound probes; and (4) detecting the hybridized mRNAs. The reagents used in each of these steps and their conditions for use may vary depending on the particular application.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions may be employed.

Hybridization is typically performed under stringent hybridization conditions. Standard hybridization techniques (e.g., under conditions sufficient to provide for specific binding of target mRNAs in the sample to the probes) are described in Kallioniemi et al., *Science* 1992, 258:818-821 and International Patent Application Publication No. WO 93/18186. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al., *Meth. Enzymol.* 1981, 21:470-480; Angerer et al., *Genetic Engineering: Principles and Methods*, Vol 7, pgs 43-65 (Plenum Press, New York, Setlow and Hollaender, eds. 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art.

Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

Other methods, such as PCR-based methods, can also be used to detect the expression of SALL4. Examples of PCR methods can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

In some embodiments, quantitative Reverse Transcription-PCR (qRT-PCR) can be used for both the detection and quantification of RNA targets (Bustin et al., *Clin. Sci.* 2005, 109:365-379). Quantitative results obtained by qRT-PCR are generally more informative than qualitative data. Thus, in some embodiments, qRT-PCR-based assays can be useful to measure mRNA levels during cell-based assays. The qRT-PCR method is also useful to monitor patient therapy. Examples of qRT-PCR-based methods can be found, for example, in U.S. Pat. No. 7,101,663, which is incorporated by reference herein in its entirety.

In contrast to regular reverse transcriptase-PCR and analysis by agarose gels, qRT-PCR gives quantitative results. An additional advantage of qRT-PCR is the relative ease and convenience of use. Instruments for qRT-PCR, such as the Applied Biosystems 7500, are available commercially, so are the reagents, such as TaqMan® Sequence Detection Chemistry. For example, TaqMan® Gene Expression Assays can be used, following the manufacturer's instructions. These kits are pre-formulated gene expression assays for rapid, reliable detection and quantification of human, mouse, and rat mRNA transcripts. An exemplary qRT-PCR program, for example, is 50° C. for 2 minutes, 95° C. for 10 minutes, 40 cycles of 95° C. for 15 seconds, then 60° C. for 1 minute.

To determine the cycle number at which the fluorescence signal associated with a particular amplicon accumulation crosses the threshold (referred to as the CT), the data can be analyzed, for example, using 7500 Real-Time PCR System Sequence Detection software vs. using the comparative CT relative quantification calculation method. Using this method, the output is expressed as a fold-change of expression levels. In some embodiments, the threshold level can be selected to be automatically determined by the software. In some embodiments, the threshold level is set to be above the baseline but sufficiently low to be within the exponential growth region of an amplification curve.

The cereblon modifying compound induced interaction between SALL4 and cereblon can be analyzed using the methods commonly known to those skilled in the art. While the various methods and approaches to analyze protein-protein interactions are too numerous to describe here, exemplary methods are briefly described below.

In some embodiments of the various methods provided herein, physical methods like co-immunoprecipitation (Co-IP) and pull-down assays are used to determine the interaction between SALL4 and cereblon. Co-IP is conducted in essentially the same manner as an immunoprecipitation (IP) of a single protein, except that the target protein precipitated by the antibody is used to co-precipitate a binding partner/protein complex from a lysate. The interacting protein is bound to the target antigen, which is bound by the antibody that is immobilized to the support. Immunoprecipitated proteins and their binding partners are commonly detected by sodium dodecyl sulfate-polyacrylamide gel electrophoresis (SDS-PAGE) and western blot analysis.

Pull-down assays are similar in methodology to co-immunoprecipitation. One difference between these two approaches is that while co-IP uses antibodies to capture protein complexes, pull-down assays use a "bait" protein to purify any proteins in a lysate that bind to the bait.

In other embodiments, methods useful for determining transient protein-protein interaction, for example, those interactions occurring only briefly as part of a single cascade or other metabolic function within cells, are used herein to determine the interaction between SALL4 and cereblon.

For example, crosslinking interacting proteins is an approach to stabilize or permanently adjoin the components of interaction complexes. Once the components of an interaction are covalently crosslinked, other steps (e.g., cell lysis, affinity purification, electrophoresis or mass spectrometry) can be used to analyze the protein-protein interaction while maintaining the original interacting complex. Homobifunctional, amine-reactive crosslinkers can be added to cells to crosslink potentially interacting proteins together, which can then be analyzed after lysis by western blotting. Crosslinkers can be membrane permeable, such as DSS, for crosslinking intracellular proteins, or they can be non-membrane permeable, such as BS3, for crosslinking cell-surface proteins. Furthermore, some crosslinkers can be cleaved by reducing agents, such as DSP or DTSSP, to reverse the crosslinks. Alternatively, heterobifunctional crosslinkers that contain a photoactivatable group, such as SDA product or Sulfo-SDA, can be used to capture transient interactions that may occur, such as after a particular stimulus. Photoactivation can also be also be after metabolic labeling with photoactivatable amino acids such as L-Photo-Leucine or L-Photo-Methionine. Crosslinking sites between proteins can be mapped by high precision using mass spectrometry, especially if a MS-cleavable crosslinker such as DSSO or DSBU is used.

In certain embodiments, label transfer protein interaction analysis can be used in the present methods. Label transfer involves crosslinking interacting molecules (i.e., bait and prey proteins) with a labeled crosslinking agent and then cleaving the linkage between the bait and prey so that the label remains attached to the prey. New non-isotopic reagents and methods continue to make this technique more accessible and simple to perform by any researcher.

In other embodiments, far-western blot analysis is used in the present methods. In a far-western blot analysis, protein-protein interactions are detected by incubating electrophoresed proteins with a purified, tagged bait protein instead of a target protein-specific antibody, respectively. See "Overview of Protein-Protein Interaction Analysis," *Pierce Protein Methods* (available from Thermo Fisher Scientific website).

In yet another embodiment, fluorescence resonance energy transfer (FRET) assay (or resonance energy transfer (RET) assay or electronic energy transfer (EET) assay) is used for determining the interaction between two proteins. Briefly, the assay is based on that energy can transfer between two light-sensitive molecules. A donor chromophore, initially in its electronic excited state, may transfer energy to an acceptor chromophore through nonradiative dipole-dipole coupling. The efficiency of this energy transfer is inversely proportional to the sixth power of the distance between donor and acceptor, making FRET extremely sensitive to small changes in distance. Measurements of FRET efficiency can be used to determine if two fluorophores are within a certain distance of each other, and thus be used to determine the interaction between two molecules.

In certain embodiments, a combination of various methods can be used to determine and/or confirm the interaction between SALL4 and cereblon.

In some embodiments of the various methods provided herein, a ubiquitination assay is used to determine the ubiquitination level of SALL4 protein. Any method known to those skilled in the art can be used and is included in the present disclosure. One exemplary ubiquitination assay uses Cisbio Bioassays's HTRF® reagents for investigating ubiquitin pathway targets. HTRF Ubiquitin assays use ubiquitin labeled with either Eu3+-Cryptate or biotin. Upon the addition of XL665 conjugate, the HTRF signal is proportional to the level of ubiquitination, and remains stable for more than 24 hours. HTRF ubiquitin assays have two basic phases, the enzymatic and the HTRF detection steps. In the enzymatic step, the target protein is incubated with the ubiquitin enzymes (E2 & E3) and Eu3+-labeled ubiquitin. The reaction starts with the addition of E1 enzyme. In the detection step, the ubiquitinated target protein is then detected by the addition of an XL665-labeled reagent that contains EDTA to stop the enzymatic reaction. Another exemplary ubiquitination assay is provided in Section 6.1 below.

In some embodiments of the various methods provided herein, the cereblon modifying compound is used to treat a cancer. In some embodiments, the screening method provided herein is for identifying a cereblon modifying compound for treating a cancer. The cancers provided herein include all cancer types treatable by any cereblon modifying compound. The cancers provided herein include (but are not limited to) cancers of the bladder, bone, blood, brain, breast, cervix, chest, colon, endrometrium, esophagus, eye, head, kidney, liver, lymph nodes, lung, mouth, neck, ovaries, pancreas, prostate, rectum, skin, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, colorectal cancer, including stage 3 and stage 4 colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma.

In some embodiments of the various methods provided herein, the cancer is solid cancer or blood borne cancer. In some embodiments, the cancer is solid cancer. In some embodiments, the solid cancer is metastatic. In some embodiments, the solid cancer is hepatocellular carcinoma, melanoma, prostate cancer, ovarian cancer, or glioblastoma.

In other embodiments, the cancer is blood borne tumor or hematological cancer. In certain embodiments, the blood borne tumor is metastatic. Such cancers include myelomas, leukemias, lymphomas (Non-Hodgkin's Lymphoma), and Hodgkin's disease (also called Hodgkin's Lymphoma). In one embodiment, the myeloma is multiple myeloma (MM). In some embodiments, the leukemia is, for example, acute myelogenous leukemia (AML), acute lymphocytic leukemia (ALL), adult T-cell leukemia, chronic lymphocytic leukemia (CLL), hairy cell leukemia, myelodysplasia, myeloproliferative disorders, chronic myelogenous leukemia (CIVIL), myelodysplastic syndrome (MDS), human lymphotropic virus-type 1 (HTLV-1) leukemia, mastocytosis, or B-cell acute lymphoblastic leukemia. In some embodiments, the lymphoma is, for example, diffuse large B-cell lymphoma (DLBCL), B-cell immunoblastic lymphoma, small non-cleaved cell lymphoma, human lymphotropic virus-type 1 (HTLV-1) leukemia/lymphoma, adult T-cell lymphoma, peripheral T-cell lymphoma (PTCL), cutaneous T-cell lymphoma (CTCL), mantle cell lymphoma (MCL), Hodgkin lymphoma (HL), non-Hodgkin lymphoma (NHL), AIDS-related lymphoma, follicular lymphoma, small lymphocytic lymphoma, T-cell/histiocyte rich large B-cell lymphoma, transformed lymphoma, primary mediastinal (thymic) large B-cell lymphoma, splenic marginal zone lymphoma, Richter's transformation, nodal marginal zone lymphoma, or ALK-positive large B-cell lymphoma. In one embodiment, the hematological cancer is indolent lymphoma including, for example, DLBCL, follicular lymphoma, or marginal zone lymphoma.

In some embodiments of the various methods provided herein, the cereblon modifying compound is used to treat a disease or disorder that is not cancer. In some such embodiments embodiment, the disease or disorder is a disease or disorder requiring a non-teratogenic treatment, for example treatment with a cereblon modifying compound that is non-teratogenic or with reduced teratogenicity compared to treatment with a reference compound. In some embodiments, the reference compound is thalidomide. In other embodiments, the reference compound is pomalidomide. In yet other embodiments, the reference compound is lenalidomide. In a specific embodiment, the teratogenicity is reduced compared to treatment with thalidomide.

In another embodiment, the disease or disorder is a disease or disorder requiring a treatment with a cereblon modifying compound that does not induce SALL4 cereblon interaction, or induces a reduced SALL4 cereblon interaction, compared to treatment with a reference compound. In some embodiments, the reference compound is thalidomide. In other embodiments, the reference compound is pomalidomide. In yet other embodiments, the reference compound is lenalidomide. In a specific embodiment, the SALL4 cereblon interaction is reduced compared to treatment with thalidomide.

In another embodiment, the disease or disorder is a disease or disorder requiring a treatment with a cereblon modifying compound that does not induce a SALL4 ubiquitination, or induces a reduced SALL4 ubiquitination, compared to treatment with a reference compound. In some embodiments, the reference compound is thalidomide. In other embodiments, the reference compound is pomalidomide. In yet other embodiments, the reference compound is lenalidomide. In a specific embodiment, the SALL4 ubiquitination is reduced compared to treatment with thalidomide.

In another embodiment, the disease or disorder is a disease or disorder requiring a treatment with a cereblon modifying compound that does not induce SALL4 degradation, or induces a reduced SALL4 degradation, compared to treatment with a reference compound. In some embodiments, the reference compound is thalidomide. In other embodiments, the reference compound is pomalidomide. In yet other embodiments, the reference compound is lenalidomide. In a specific embodiment, the SALL4 degradation is reduced compared to treatment with thalidomide.

The cereblon modifying compound (or treatment compound) provided herein can directly or indirectly regulate cereblon and/or the binding of cereblon with its substrates. In some embodiments, the cereblon modifying treatment compound directly binds to cereblon. In some embodiments, the cereblon modifying treatment compound induces conformational change in the cereblon protein. In some embodiments, the cereblon modifying treatment compound changes the substrate specificity or affinity of the cereblon protein. In some embodiments, the cereblon modifying treatment compound changes the properties of the cereblon protein surface.

In some embodiments, the cereblon modifying compound is an immunomodulatory compound. In some embodiments, the cereblon modifying treatment compound is thalidomide, or an enantiomer or a mixture of enantiomers thereof or a pharmaceutically acceptable salt, solvate, hydrate, co-crystal, clathrate, or polymorph thereof. In some embodiments, the cereblon modifying treatment compound is lenalidomide, or an enantiomer or a mixture of enantiomers thereof; or a pharmaceutically acceptable salt, solvate, hydrate, co-crystal, clathrate, or polymorph thereof. In some embodiments, the cereblon modifying treatment compound is pomalidomide, or an enantiomer or a mixture of enantiomers thereof or a pharmaceutically acceptable salt, solvate, hydrate, co-crystal, clathrate, or polymorph thereof.

In certain embodiments, the method provided herein is for screening a compound that has been determined to be a cereblon modifying compound or to further select or identify one or more cereblon modifying compounds that have reduced teratogenic effects. In some embodiments, the cereblon modifying compound binds directly to cereblon. Thus, in certain embodiments, the methods provided herein further comprise determining or confirming the binding of a compound to cereblon. The binding of a compound to cereblon can be determined by methods known to those skilled in the art. In some embodiments, the cereblon modifying compound binds to human cereblon. In other embodiments, the cereblon modifying compound binds to mouse cereblon. Cereblon modifying compounds binding to cereblon from other species are also included in the present disclosure.

In some embodiments, the cereblon modifying compound has been determined to induce a cereblon conformational change (e.g., within the compound-binding pocket of the cereblon) or to otherwise alter the properties of a cereblon surface.

In certain embodiments, the method for determining if a compound is a cereblon modifying compound or if a compound binds to cereblon comprises (a) (i) obtaining a first crystal structure of cereblon and a reference compound, and (ii) determining a three-dimensional structure of the first crystal by x-ray diffraction to obtain a first set of atomic coordinates; (b) (i) obtaining a second crystal comprising CRBN and the compound, and (ii) determining a three-dimensional structure of the second crystal by x-ray diffraction to obtain a second set of atomic coordinates; and (c) comparing said first set of atomic coordinates with said second set of atomic coordinates; wherein a difference in atomic coordinates is indicative of a compound that induces a cereblon conformational change or otherwise alters the properties of a cereblon surface. In some embodiments, the first set of atomic coordinates and/or said second set of atomic coordinates define a compound binding domain. In certain embodiments, the difference in atomic coordinates is determined by assessing differences in atomic distances.

In certain embodiments, the reference compound is not a cereblon modifying compound. In certain embodiments, the reference compound does not bind to cereblon, and thus the crystal structure of cereblon and the reference compound represent a control crystal structure in which the conformation of cereblon is not changed by a compound.

In certain embodiments, the method for determining if a compound is a cereblon modifying compound or if a compound binds to cereblon comprises (a) obtaining a first three-dimensional structure of cereblon and a reference compound; (b) obtaining a second three-dimensional structure of cereblon and the compound; and (c) comparing said first three-dimensional structure with said second three-dimensional structure; wherein a difference in the first and second three-dimensional structures is indicative of a compound that induces a CRBN conformational change or otherwise alters the properties of a CRBN surface. In certain embodiments, the reference compound is not a cereblon modifying compound and the first three-dimensional structure is a control structure of a cereblon that is not bound to a compound.

In an embodiment, the conformational change or alteration is assessed by x-ray crystallography. In other embodiments, the three-dimensional structure is assessed by NMR spectroscopy, dual polarization interferometry, vibrational spectroscopy, or cryo-electron microscopy. In some embodiments, the cereblon is further bound to DDB1, Cul4, Roc1, or any combination thereof.

In certain embodiments, the method provided herein further comprises analyzing, characterizing, and testing the cereblon modifying compound (or the selected compound) in one or more assays (e.g., biological assays). In certain embodiments, the method provided herein further comprises testing the therapeutic effects of the cereblon modifying compound (or the selected compound).

In certain embodiments of the various methods provided herein, the method provided herein further comprises administering the cereblon modifying compound selected and/or characterized based on the methods provided herein to a subject to evaluate its therapeutic effects.

In yet other embodiments, the method provided herein further comprises administering the cereblon modifying compound selected and/or characterized based on the methods provided herein to a subject to treat a disease or disorder, such as a cancer. Thus, in certain aspect, provided herein are methods of treating patients who have been previously treated for cancer but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not.

In certain embodiments, the disease or disorder is a cancer. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day.

In certain embodiments, the therapeutically or prophylactically effective amount is about 0.1, about 0.2, about 0.5, about 1, about 2, about 5, about 10, about 15, about 20, about 25, about 30, about 40, about 45, about 50, about 60, about 70, about 80, about 90, about 100, or about 150 mg per day.

In one embodiment, the recommended daily dose range of the treatment compound, or a stereoisomer or a mixture of stereoisomers, tautomer, pharmaceutically acceptable salt, solvate, isotopologue, prodrug, hydrate, co-crystal, clathrate, or a polymorph thereof, for the conditions described herein lie within the range of from about 0.1 mg to about 50 mg per day, for example, given as a single once-a-day dose, or in divided doses throughout a day. In some embodiments, the dosage ranges from about 1 mg to about 50 mg per day. In other embodiments, the dosage ranges from about 0.5 mg to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg per day.

In a specific embodiment, the recommended starting dosage may be 0.5, 1, 2, 3, 4, 5, 10, 15, 20, 25, or 50 mg per day. In another embodiment, the recommended starting dosage may be 0.5, 1, 2, 3, 4, or 5 mg per day. The dose may be escalated to 10, 15, 20, 25, 30, 35, 40, 45, or 50 mg per day.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both. For example, a dose of 1 mg/kg/day for a 65 kg human is approximately equal to 38 mg/m$^2$/day.

In certain embodiments, the amount of the cereblon modifying compound administered is sufficient to provide a plasma concentration of the compound at steady state, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In other embodiments, the amount of the cereblon modifying compound administered is sufficient to provide a plasma concentration of the compound at steady state, ranging from about 5 to about 100 nM, about 5 to about 50 nM, about 10 to about 100 nM, about 10 to about 50 nM, or from about 50 to about 100 nM.

As used herein, the term "plasma concentration at steady state" is the concentration reached after a period of administration of a cereblon modifying compound, or a stereoisomer or a mixture of stereoisomers, tautomer, pharmaceutically acceptable salt, solvate, isotopologue, prodrug, hydrate, co-crystal, clathrate, or a polymorph thereof. Once steady state is reached, there are minor peaks and troughs on the time-dependent curve of the plasma concentration of the compound.

In certain embodiments, the amount of the cereblon modifying compound administered is sufficient to provide a maximum plasma concentration (peak concentration) of the compound, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In certain embodiments, the amount of the cereblon modifying compound administered is sufficient to provide a minimum plasma concentration (trough concentration) of the compound, ranging from about 0.001 to about 500 μM, about 0.002 to about 200 μM, about 0.005 to about 100 μM, about 0.01 to about 50 μM, from about 1 to about 50 μM, about 0.01 to about 25 μM, from about 0.01 to about 20 μM, from about 0.02 to about 20 μM, from about 0.02 to about 20 μM, or from about 0.01 to about 20 μM.

In certain embodiments, the amount of the cereblon modifying compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

Depending on the disease to be treated and the subject's condition, the cereblon modifying compound provided herein may be administered by parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The compound provided herein may be formulated, alone or together, in suitable dosage unit with pharmaceutically acceptable excipients, carriers, adjuvants, and vehicles, appropriate for each route of administration.

In one embodiment, the cereblon modifying compound provided herein is administered parenterally. In another embodiment, the compound is administered intravenously.

The cereblon modifying compound can be delivered as a single dose (e.g., a single bolus injection), or over time (e.g., continuous infusion over time or divided bolus doses over time). The cereblon modifying compound can be administered repeatedly if necessary, for example, until the patient experiences stable disease or regression, or until the patient experiences disease progression or unacceptable toxicity. For example, stable disease for solid cancers generally means that the perpendicular diameter of measurable lesions has not increased by 25% or more from the last measurement (Therasse et al., *J. Natl. Cancer Inst.*, 92(3):205-216 (2000)). Stable disease or lack thereof is determined by methods known in the art such as evaluation of patient symptoms, physical examination, and visualization of the tumor that has been imaged using X-ray, CAT, PET, MRI scan, or other commonly accepted evaluation modalities.

The cereblon modifying compound provided herein can be administered once daily (QD) or divided into multiple daily doses such as twice daily (BID), three times daily (TID), and four times daily (QID). In addition, the administration can be continuous (i.e., daily for consecutive days or every day) or intermittent, e.g., in cycles (i.e., including days, weeks, or months of rest without compound). As used herein, the term "daily" is intended to mean that a treatment compound is administered once or more than once each day, for example, for a period of time. The term "continuous" is intended to mean that a treatment compound is administered daily for an uninterrupted period of at least 10 days to 52 weeks. The term "intermittent" or "intermittently" as used herein is intended to mean stopping and starting at either regular or irregular intervals. For example, intermittent administration of the cereblon modifying compound is administration for one to six days per week, administration in cycles (e.g., daily administration for two to eight consecutive weeks, then a rest period with no administration for up to one week), or administration on alternate days. The term "cycling" as used herein is intended to mean that a cereblon modifying compound is administered daily or continuously but with a rest period. In certain embodiments, the rest period is the same length as the treatment period. In other embodiments, the rest period has different length from the treatment period. In some embodiments, the length of cycling is 1, 2, 3, 4, 5, 6, 7, 8, 9, or 10 weeks. In some embodiments of cycling, the cereblon modifying compound is administered daily for a period of 1, 2, 3, 4, 5, 6, 7, 8, 9, 10, 15, 20, 25, or 30 days, followed by a rest period. In a particular embodiment, the cereblon modifying compound is administered daily for a period of 5 days of a 4 week cycle. In another particular embodiment, the cereblon modifying compound is administered daily for a period of 10 days of a 4 week cycle.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the cereblon modifying compound is administered once a day. In another embodiment, the cereblon modifying compound is administered twice a day. In yet another embodiment, the compound is administered three times a day. In still another embodiment, the cereblon modifying compound is administered four times a day.

In certain embodiments, the cereblon modifying compound is administered once per day from one day to six months, from one week to three months, from one week to four weeks, from one week to three weeks, or from one week to two weeks. In certain embodiments, the cereblon modifying compound is administered once per day for one week, two weeks, three weeks, or four weeks. In one embodiment, the cereblon modifying compound is administered once per day for one week. In another embodiment, the cereblon modifying cereblon modifying compound is administered once per day for two weeks. In yet another embodiment, the cereblon modifying compound is administered once per day for three weeks. In still another embodiment, the cereblon modifying compound is administered once per day for four weeks.

In certain embodiments, the cereblon modifying compound is formulated in a pharmaceutical composition and is administered to a patient in the form of a pharmaceutical composition In some embodiments of the various methods provided herein, the method further comprises administering a therapeutically effective amount of a second active agent or a support care therapy. The second active agents can be large molecules (e.g., proteins) or small molecules (e.g., synthetic inorganic, organometallic, or organic molecules). In some embodiments, the second active agent is a hematopoietic growth factor, cytokine, anti-cancer agent (e.g., a checkpoint inhibitor), antibiotic, cox-2 inhibitor, immunomodulatory agent, immunosuppressive agent, corticosteroid, therapeutic antibody that specifically binds to a cancer antigen or a pharmacologically active mutant, or derivative thereof. In certain embodiments, the anti-cancer agent is a checkpoint inhibitor.

In some embodiments, the second active agents are small molecules that can alleviate adverse effects associated with the administration of a cereblon modifying compound, or a stereoisomer or a mixture of stereoisomers, tautomer, pharmaceutically acceptable salt, solvate, isotopologue, prodrug, hydrate, co-crystal, clathrate, or a polymorph thereof. Many small molecule second active agents are believed to be capable of providing a synergistic effect when administered with (e.g., before, after, or simultaneously) a cereblon modifying compound, or a stereoisomer or a mixture of stereoisomers, tautomer, pharmaceutically acceptable salt, solvate, isotopologue, prodrug, hydrate, co-crystal, clathrate, or a polymorph thereof. Examples of small molecule second active agents include, but are not limited to, anti-cancer agents, antibiotics, immunosuppressive agents, and steroids.

5.3 Kits

Also provided herein are kits for performing any methods provided herein. In another aspect, provided herein is a kit comprising an agent for determining the level of SALL4 (or a variant thereof). In some embodiments, the kit is for determining the degradation of SALL4 after treatment with a cereblon modifying compound.

In another aspect, provided herein is a kit comprising an agent for determining the ubiquitination of SALL4 (or a variant thereof). In some embodiments, the kit is for determining the ubiquitination of SALL4 after treatment with a cereblon modifying compound.

In yet another aspect, provided herein is a kit comprising an agent for determining the interaction between SALL4 or a fragment thereof with cereblon or a fragment thereof. In some embodiments, the kit is for determining the interaction between SALL4 or a fragment thereof and cereblon or a fragment thereof after treatment with a cereblon modifying compound.

For example, the kit can comprise a probe (e.g., an oligonucleotide, antibody, labeled compound or other agent) capable of detecting the presence (or absence) or amount of SALL4. The kit may also comprise instructions.

Probes may specifically hybridize to genomic sequences, nucleic acid products, or polypeptide products. The disclosed kits can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for use.

In certain embodiments of various kits provided herein, the kit may also include tools or agents for obtaining a sample. In some embodiments, the tool or agent is for obtaining samples from a tumor biopsy, a node biopsy, blood, or a biopsy from the bone marrow, spleen, liver, brain, or breast. The biological sample can be, for example, a cell culture, a cell line, a tissue, an organ, an organelle, a biological fluid, a blood sample, a urine sample, or a skin sample.

In certain embodiments, the kit comprises one or more probes that bind specifically to the nucleic acid (e.g., mRNA) of a SALL4. In certain embodiments, the kit further comprises a washing solution. In certain embodiments, the kit further comprises reagents for performing a hybridization assay, nucleic acid isolation or purification means, detection means, as well as positive and negative controls. In certain embodiments, the kit further comprises an instruction for using the kit. The kit can be tailored for in-home use, clinical use, or research use.

In certain embodiments, provided herein is a kit for detecting the protein level of SALL4. In certain embodiments, the kits comprises a dipstick coated with an antibody that recognizes a specific protein, washing solutions, reagents for performing the assay, protein isolation or purification means, detection means, as well as positive and negative controls. In certain embodiments, the kit further comprises an instruction for using the kit. The kit can be tailored for in-home use, clinical use, or research use.

Such a kit can employ, for example, a dipstick, a membrane, a chip, a disk, a test strip, a filter, a microsphere, a slide, a multi-well plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide.

In another embodiment, the kit comprises a solid support, nucleic acids attached to the support, where the nucleic acids are complementary to at least 20, 50, 100, 200, 350, or more bases of nucleic acid, and a means for detecting the expression of gene in a biological sample.

In a specific embodiment, the pharmaceutical or assay kit comprises, in a container, a compound or a pharmaceutical composition thereof, and further comprises, in one or more containers, components for isolating nucleic acid. In another specific embodiment, the pharmaceutical or assay kit comprises, in a container, a compound or a pharmaceutical composition, and further comprises, in one or more containers, components for conducting RT-PCR, qRT-PCR, deep sequencing, or microarray.

In certain embodiments, the kits provided herein employ means for detecting the expression of a protein by quantitative real-time PCR (qRT-PCR), microarray, flow cytometry, or immunofluorescence. In other embodiments, the expression of the protein is measured by ELISA-based methodologies or other similar methods known in the art.

In another specific embodiment, the pharmaceutical or assay kit comprises, in a container, a compound or a pharmaceutical composition thereof, and further comprises, in one or more containers, components for isolating protein. In another specific embodiment, the pharmaceutical or assay kit comprises, in a container, a compound or a pharmaceutical composition, and further comprises, in one or more containers, components for conducting flow cytometry or ELISA.

In another aspect, provided herein are kits for measuring SALL4 that supply the materials necessary to measure the abundance of one or more gene products. In some embodiments, such kits may comprise materials and reagents required for measuring RNA or protein. In some embodiments, such kits include microarrays, wherein the microarray is comprised of oligonucleotides and/or DNA and/or RNA fragments which hybridize to one or more gene products. In some embodiments, such kits may include primers for PCR of either the RNA product or the cDNA copy of the RNA product. In some embodiments, such kits may include primers for PCR as well as probes for qPCR. In some embodiments, such kits may include multiple primers and multiple probes, wherein some of the probes have different fluorophores so as to permit simultaneously measuring multiple gene products. In some embodiments, such kits may further include materials and reagents for creating cDNA from RNA. In some embodiments, such kits may include antibodies specific for the protein products. Such kits may additionally comprise materials and reagents for isolating RNA and/or proteins from a biological sample. In addition, such kits may include materials and reagents for synthesizing cDNA from RNA isolated from a biological sample.

For nucleic acid microarray kits, the kits generally comprise probes attached to a solid support surface. In one such embodiment, probes can be either oligonucleotides or longer probes including probes ranging from 150 nucleotides to 800 nucleotides in length. The probes may be labeled with a detectable label. In a specific embodiment, the probes are specific for one or more of the gene products. The microarray kits may comprise instructions for performing the assay and methods for interpreting and analyzing the data resulting from performing the assay.

For quantitative PCR, the kits generally comprise preselected primers specific for particular nucleic acid sequences. The quantitative PCR kits may also comprise enzymes suitable for amplifying nucleic acids (e.g., polymerases such as Taq polymerase), deoxynucleotides, and buffers needed for amplification reaction. The quantitative PCR kits may also comprise probes specific for the nucleic acid sequences associated with or indicative of a condition. The probes may or may not be labeled with a fluorophore. The probes may or may not be labeled with a quencher molecule. In some embodiments, the quantitative PCR kits also comprise components suitable for reverse-transcribing RNA, including enzymes (e.g., reverse transcriptases such as AMV, MMLV, and the like) and primers for reverse transcription along with deoxynucleotides and buffers needed for reverse transcription reaction. Each component of the quantitative PCR kit is generally in its own suitable container. Thus, these kits generally comprise distinct containers suitable for each individual reagent, enzyme, primer and probe. Further, the quantitative PCR kits may comprise instructions for performing the reaction and methods for interpreting and analyzing the data resulting from performing the reaction.

For antibody-based kits, the kit can comprise, for example: (1) a first antibody (which may or may not be attached to a solid support) that binds to a peptide, polypeptide or protein of interest; and, optionally, (2) a second, different antibody that binds to either the first antibody or the peptide, polypeptide, or protein, and is conjugated to a detectable label (e.g., a fluorescent label, radioactive isotope, or enzyme). The antibody-based kits may also comprise beads for conducting immunoprecipitation. Each component of the antibody-based kits is generally in its own suitable container. Thus, these kits generally comprise distinct containers suitable for each antibody and reagent. Further, the antibody-based kits may comprise instructions for performing the assay and methods for interpreting and analyzing the data resulting from performing the assay.

In one embodiment, a kit provided herein comprises a cereblon modifying compound, or a pharmaceutically acceptable salt, solvate, stereoisomer, isotopologue, prodrug, hydrate, co-crystal, clathrate, or a polymorph thereof. Kits may further comprise additional active agents, including but not limited to those disclosed herein.

Kits provided herein may further comprise devices that are used to administer the compound. Examples of such devices include, but are not limited to, syringes, drip bags, patches, and inhalers.

Kits may further comprise cells or blood for transplantation, as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to, water for injection USP; aqueous vehicles (such as, but not limited to, sodium chloride injection, Ringer's injection, dextrose injection, dextrose and sodium chloride injection, and lactated Ringer's injection); water-miscible vehicles (such as, but not limited to, ethyl alcohol, polyethylene glycol, and polypropylene glycol); and non-aqueous vehicles (such as, but not limited to, corn oil, cottonseed oil, peanut oil, sesame oil, ethyl oleate, isopropyl myristate, and benzyl benzoate).

In certain embodiments of the methods and kits provided herein, solid phase supports are used for purifying proteins, labeling samples, or carrying out the solid phase assays. Examples of solid phases suitable for carrying out the methods disclosed herein include beads, particles, colloids, single surfaces, tubes, multi-well plates, microtiter plates, slides, membranes, gels, and electrodes. When the solid phase is a particulate material (e.g., a bead), it is, in one embodiment, distributed in the wells of multi-well plates to allow for parallel processing of the solid phase supports.

The disclosed kits may be multiplex kits useful for simultaneously measuring the presence or absence of genetic components and the presence or absence of proteins or the levels thereof.

5.4 Compounds

The compounds provided herein include cereblon modifying compounds. In some embodiments, the cereblon modifying compounds provided herein directly or indirectly modulate the CRBN E3 ubiquitin-ligase complex. In some embodiments, the cereblon modifying compounds provided herein can bind directly to cereblon and induce a conformational change in the CRBN protein. In other embodiments, the cereblon modifying compounds provided herein can bind directly to other subunits in the CRBN E3 ubiquitin-ligase complex.

Compounds for the methods provided herein include, but are not limited to, the immunomodulatory compounds, a group of compounds that can be useful to treat several types of human diseases, including certain cancers.

As used herein and unless otherwise indicated, the term "immunomodulatory compound" or "immunomodulatory agent" can encompass certain small organic molecules that inhibit LPS induced monocyte TNF-α, IL-1ß, IL-12, IL-6, MIP-1α, MCP-1, GM-CSF, G-CSF, and COX-2 production. Without being limited by a particular theory, one of the biological effects exerted by the immunomodulatory compounds disclosed herein is the reduction of myeloid cell TNF-α production. Immunomodulatory compounds disclosed herein may enhance the degradation of TNF-α mRNA. Further, without being limited by theory, immunomodulatory compounds disclosed herein may also be potent co-stimulators of T cells and increase cell proliferation dramatically in a dose dependent manner. Immunomodulatory compounds disclosed herein may also have a greater co-stimulatory effect on the CD8+ T cell subset than on the CD4+ T cell subset. In addition, the compounds may have anti-inflammatory properties against myeloid cell responses, yet efficiently co-stimulate T cells to produce greater amounts of IL-2, IFN-γ, and to enhance T cell proliferation and CD8+ T cell cytotoxic activity. Further, without being limited by a particular theory, immunomodulatory compounds disclosed herein may be capable of acting both indirectly through cytokine activation and directly on Natural Killer ("NK") cells and Natural Killer T ("NKT") cells, and increase the NK cells' ability to produce beneficial cytokines such as, but not limited to, IFN-γ, and to enhance NK and NKT cell cytotoxic activity.

Exemplary immunomodulatory compounds provided herein include but are not limited to thalidomide, lenalidomide, and pomalidomide, or an enantiomer or a mixture of enantiomers thereof; or a pharmaceutically acceptable salt, solvate, hydrate, co-crystal, clathrate, or polymorph thereof.

Various immunomodulatory compounds disclosed herein contain one or more chiral centers, and can exist as racemic mixtures of enantiomers or mixtures of diastereomers. Thus, also provided herein is the use of stereomerically pure forms of such compounds, as well as the use of mixtures of those forms. For example, mixtures comprising equal or unequal amounts of the enantiomers of a particular immunomodulatory compounds may be used. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., Tetrahedron 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

All of the compounds described can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

In certain embodiments of the various compositions and methods provided herein, a cereblon modifying compound is an immunomodulatory compound provided herein. In other embodiments, a cereblon modifying compound is not an immunomodulatory compound.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

It is noted that any combination of the above-listed embodiments, for example, with respect to one or more reagents, such as, without limitation, nucleic acid primers, solid support, and the like, are also contemplated in relation to any of the various methods and/or kits provided herein.

Certain embodiments of the invention are illustrated by the following non-limiting examples.

6. EXAMPLES

The examples below are carried out using standard techniques, which are well known and routine to those of skill in the art, except where otherwise described in detail. The examples are intended to be merely illustrative.

6.1 Methods

Protein Expression and Purification

MBP-fused WT and mutant protein were expressed in *E. coli* BL21 (DE3) Star cells (Life Technologies) using 2XYT media (Teknova). Cells were induced at $OD_{600}$ 0.6 for 18 hours at 16° C. Cells were pelleted, frozen, thawed for purification, and resuspended in B-PER Bacterial Protein Extraction buffer (Thermo Fisher) containing 150 μM zinc acetate, 40,000 U benzonase (Novagen), and 1× protease inhibitor cocktail (San Diego Bioscience). Lysates were incubated with amylose resin (NEB) at 4° C. for 1 hour before beads were washed. Protein was eluted with buffer containing 200 mM NaCl, 50 mM Tris pH 7.5, 3 mM TCEP, 10% glycerol, 150 μM zinc acetate, and 10 mM maltose.

Cereblon-DDB1 Purification

ZZ-domain-6×His-thrombin-tagged human cereblon (amino acids 40-442) and full length human DDB1 were co-expressed in SF9 insect cells in ESF921 medium (Expression Systems), in the presence of 50 uM zinc acetate. Cells were resuspended in buffer containing 50 mM Tris-HCl pH 7.5, 500 mM NaCl, 10 mM imidazole, 10% glycerol, 2 mM TCEP, 1× Protease Inhibitor Cocktail (San Diego Bioscience), and 40,000 U Benzonase (Novagen), and sonicated for 30 s. Lysate was clarified by high speed spin at 30,000 rpm for 30 minutes, and clarified lysate was incubated with Ni-NTA affinity resin (Qiagen) for 1 hour. Complex was eluted with buffer containing 500 mM imidazole, and the ZZ-domain-6×His tag removed by thrombin cleavage (Enzyme Research) overnight, combined with dialysis in 10 mM imidazole buffer. Cleaved eluate was incubated with Ni-NTA affinity resin (Qiagen), and the flow-through diluted to 200 mM NaCl for further purification over an ANX HiTrap ion exchange column (GE Healthcare). The ANX column was washed with 10 column volumes 50 mM Tris-HCl pH 7.5, 200 mM NaCl, 3 mM TCEP, followed by 10 column volumes of 50 mM Bis-Tris pH 6.0, 200 mM NaCl, 3 mM TCEP, and the cereblon-DDB1 peak eluted at 210 mM NaCl. This peak was collected and further purified by size exclusion chromatography using a Sephacryl S-400 16/60 column (GE Healthcare) in buffer containing 10 mM HEPES pH 7.0, 240 mM NaCl, and 3 mM TECP. The cereblon-DDB1 complex was concentrated to 30 mg/mL.

Full length human cereblon, full length mouse cereblon, and full length rabbit cereblon were co-expressed with full length human DDB1 in SF9 insect cells in ESF921 medium in the presence of 50 uM zinc acetate. Cells were resuspended in buffer containing 50 mM Tris-HCl pH 7.5, 500 mM NaCl, 10 mM imidazole, 10% glycerol, 2 mM TCEP, 1× Protease Inhibitor Cocktail (San Diego Bioscience), and 40,000 U Benzonase (Novagen), and sonicated for 30 s. Lysate was clarified by high speed spin at 30,000 rpm for 30 minutes, and clarified lysate was incubated with Ni-NTA affinity resin (Qiagen) for 1 hour. Complex was eluted with buffer containing 500 mM imidazole, and the ZZ-domain-6×His tag removed by thrombin cleavage (Enzyme Research) overnight, combined with dialysis in 10 mM imidazole buffer. Cleaved eluate was incubated with Ni-NTA affinity resin (Qiagen), and the flow-through diluted to 200 mM NaCl for further purification over a Sephacryl S-400 16/60 column (GE Healthcare) in buffer containing 10 mM HEPES pH 7.0, 240 mM NaCl, and 3 mM TECP.

Zinc Finger Protein Purification

Domain boundaries for the individually purified MBP-fused zinc finger domains always include the 5 amino acids N-terminal and one amino acid C-terminal to the zinc finger domains as named in the text (all numbering from Uniprot Isoform 1). MBP-fused WT and mutant SALL4, Ikaros, and ZFP91 zinc finger domain protein were expressed in E. coli BL21 (DE3) Star cells (Life Technologies) using 2XYT media (Teknova). Cells were induced at $OD_{600}$ 0.6 for 18 hours at 16° C. Cells were pelleted, frozen, thawed for purification, and resuspended in B-PER Bacterial Protein Extraction buffer (Thermo Fisher) containing 150 μM zinc acetate, 40,000 U benzonase (Novagen), and 1× protease inhibitor cocktail (San Diego Bioscience). Lysates were incubated with amylose resin (NEB) at 4° C. for 1 hour before beads were washed. Protein was eluted with buffer containing 200 mM NaCl, 50 mM Tris pH 7.5, 3 mM TCEP, 10% glycerol, 150 μM zinc acetate, and 10 mM maltose.

In Vitro Ubiquitination Assays

Purified E1, E2, ubiquitin, Cul4A-Rbx1, cereblon-DDB1, and GSPT1 proteins were used to reconstitute the ubiquitination of MBP-fused WT and mutant proteins in vitro. Substrate proteins purified by maltose affinity resin (NEB) were incubated at an approximate concentration of 30 uM. Ubiquitination components described briefly: Human cereblon-DDB1 (cereblon amino acids 40-442 and full length DDB1) and 6×his-DDB1 alone were co-expressed in SF9 insect cells in the presence of 50 μM zinc acetate, and purified by nickel affinity resin (Qiagen), HiTrap ANX column ion exchange (GE Healthcare), and Sephacryl 400 16/60 size exclusion chromatography (GE healthcare). Human full length Cul4A and Rbx1 were co-expressed in SF9 insect cells and purified by nickel affinity resin and Superdex 200 16/60 size exclusion chromatography. Purified recombinant human Ube1 E1 (E-305), UbcH5a E2 (E2-616), and ubiquitin (U-100H) were purchased from R&D systems. Components were mixed to final concentrations of 10 mM ATP, 1 μM Ube1, 25 μM UbcH5a, 200 μM Ub, 1 μM Cul4-Rbx1, 25 μM GSPT1, and 1 μM cereblon-DDB1, with or without 100 μM compound as indicated in ubiquitination assay buffer (20 mM HEPES pH 7.5, 150 mM NaCl, 10 mM $MgCl_2$). After preincubation of E1, E2, ATP and ubiquitin for 30 minutes, and separate pre-incubation of MBP-substrate, CRBN-DDB1, Cul4-Rbx1, and compound for 5 minutes at room temperature, ubiquitination reactions were started by mixing the two pre-incubations. Reactions were incubated at 30 C for 2 hours before separation by SDS-PAGE followed by coomassie staining or immunoblot analysis.

Human iPS Cell Culture

Human iPS cell lines ACS-1019 and ACS-1011 (derived from healthy donors) were obtained from ATCC. The hiPSCs were maintained in mTESR-1 medium (Stem Cell Technologies) in cell culture plates coated with a thin layer of Matrigel (BD Biosciences) incubated at 37° C. in a humidified 5% CO2 incubator according to the manufacturer's instruction. Cells were split through mechanic passaging with a glass pipet and enzymatically digestion with Dispase or Accutase every 2 to 3 days.

CRISPR-Mediated Cereblon Knockout

Human iPSCs, ACS-1019 was transduced with lentiviral vectors expressing CRISPR-Cas9 and small guide RNA targeting cereblon for 4 days. The resulting colonies were amplified and screened for cereblon knockout by immunoblot analysis with anti-CRBN65 antibody (Celgene).

Real-Time PCR

Total RNA was extracted from human iPS cells using RNeasy Mini Kit (Qiagen) according to manufacturer's instruction, and reverse-transcribed into first-strand cDNA with random primer using SuperScript™ IV First-Strand Synthesis System (ThermoFisher). Real-time PCR was performed in triplicate using ViiA 7 Real-Time PCR System with TaqMan Gene Expression Assay probes (ThermoFisher) for SALL4 (#4351372), POU5F1(#4331182) and GAPDH (#4326317E).

Plasmids

The coding sequence of human SALL4 was in vitro synthesized by Genscript, and subcloned into pDONR223 via BP recombination to generate pDONR223-SALL4. Then, site directed mutagenesis via overlapping PCR was carried out to generate pDONR223-SALL4 -G416A and pDONR223-SALL4-G600A. Next, pDONR223-SALL4, pDONR223-SALL4 -G416A and pDONR223-SALL4-G600A were shuttled into pLOC-EF1α-3×HA-gateway-IRES-Pur through gateway recombination to generate pLOC-EF1α-3×HA-SALL4 -IRES-Pur, pLOC-EF1α-3×HA-SALL4 -G416A-IRES-Pur and pLOC-EF1α-3×HA-SALL4 -G600A-IRES-Pur. The coding sequence of human CRBN was PCR-amplified from a human cDNA clone (Dharmacon), and shuttled into pDONR223 via BP recombination to generate pDONR223-CRBN. Then, pDONR223-CRBN was shuttled into pDEST27 (Invitrogen) to generate pDEST27-CRBN.

Lentiviral Production and Infection

Lentiviral plasmid was cotransfected with the 2nd Generation packaging system (ABM) into lenti-X-293 cells (Clontech) using Lipofectamine® 2000. After 16 hours of incubation, media was changed to fresh DMEM media supplemented with 20% FBS. Two days post transfection, viral supernatant was collected and cleared via centrifugation at 2000 rpm for 5 minutes, and then filtered through a 0.45 micron cellulose acetate or nylon filter unit. Cells were infected with lentivirus at a multiplicity of infection of ~0.5. After twelve hours, viral supernatant was removed and complete culture media was added to the cells. Forty-eight hours later, cells were incubated with 1-2 μg/mL puromycin or 10-20 μg/mL blasticidin for an additional 3 days to select cells stably integrated with lentiviral vectors.

Co-Immunoprecipitation of CRBN and SALL4

Lenti-X-293 cells were cotransfected with pDEST27-CRBN, which encodes GST-CRBN, and pLOC empty vector (Thermo Fisher), which contains a blasticidin resistant gene. Two days after transfection, cells were trypsinized and seeded into 96-well plates through limiting dilution. After selectin with blasticidin (20 μg/mL) for 2 weeks, single clones were picked, expanded and screened for overexpression of GST-CRBN via immunoblot analysis with anti-CRBN65 antibody. Next, lenti-X-293 cells stably expressing GST-CRBN Human were infected with lentiviruses expressing SALL4 wild-type and variants to generate lenti-x-293 cells stably expressing GST-CRBN and SALL4. Then, cells were treated with DMSO or 40 μM thalidomide for 8 hours in the presence of 1 μM MLN4924, and lysed in Buffer B [50 mM Tris (pH 7.4), 150 mM NaCl, 0.5% NP-40, 10% glycerol, 1× Complete Ultra protease inhibitor (Roche), and 1× PhosphoSTOP (Roche)]. Whole cell extracts were cleared via centrifugation at 14,000 rpm for 10 minutes, followed by incubation with anti-HA affinity resin (Roche) at 4° C. overnight. After washing the anti-HA resin with Buffer B for 6 times, anti-HA immunoprecipitates were eluted by boiling in 2×LDS loading buffer at 90° C. for 5 minutes, and then subjected to immunoblot analysis.

Cellular Degradation of SALL4

Lenti-x-293 cells stably expressing GST-CRBN and SALL4 variants were treated with DMSO or 40 μM thalidomide for 16 hours. Cells were then wished with ice-cold 1×PBS twice, lysed in buffer A [50 mM Tris. CL, 150 mM NaCl, 1% triton-x 100, complete protease inhibitor tablet (Roche), phosphatase inhibitor tablet (Roche)]. Whole cell extracts were harvested and subjected to immunoblot analysis.

Thalidomide Treatment in Male New Zealand White Rabbits

Male New Zealand white rabbits were treated with vehicle (1% Carboxymethylcellulose in deionized water), or Thalidomide at either 30 or 150 mg/kg/day for 56 days to investigate testicular degeneration. Testis were collected 24 hours after the last dose, fixed in 10% NBF, processed, embedded in paraffin and sectioned at 4 microns for immunohistochemistry.

In Vivo Rabbit Embryo Studies

All animals were housed and fed according to IACUC approved procedures. The rabbits either remained untreated (n=4 per time point) or received 180 mg/kg of Thalidomide per day (n=5 per time point) starting on GD7. Dose levels and sensitive gestation windows were selected based on previously reported finding in Thalidomide teratogenicity studies (Christian M S, birth defect research, 2007)

There were no significant differences in implantation frequency in control and Thalidomide treated rabbits during early gestation (GD 8-12). The average number of implantation sites for the Thal treated group were 8.2, 10.4, 8.75, 7.4, and 8.8 for Day 8, Day 9, Day 10, Day 11, and Day 12, respectively. The average number of implantation sites for the control group were 8.5, 7.25, 7, 9.5, and 7.5 for Day 8, Day 9, Day 10, Day 11, and Day 12, respectively.

Resorption sites, embryo mortality and gross observations were recorded during embryo collection. Embryo mortality was based on the absence of a heartbeat. There were no resorption sites or embryo and placental abnormalities in the control group. Resorptions and embryo mortality were noted on GD9, 10, 11 and 12 in Thalidomide treated rabbits and were most pronounced on GD12. On Day 8, all 41 implantation sites from 5 rabbits appeared normal. On Day 9, 1/5 rabbits were affected and there was 1 resorption site out of a total of 52 implantation sites. On Day 10, 1/5 rabbit was affected and there was 1 resorption site out of a total of 38 implantation sites. On Day 11, 3/5 rabbits were affected, with 2 resorptions sites (5.41%) and 2 dead embryos (5.41%) out of 37 implantation sites. On Day 12, 5/5 rabbits were affected, with 3 resorption sites (6.98%) and 11 dead embryos (25.58%) out of 45 implantation sites.

Cesarean sections were performed in each rabbit 3 hours after the last Thalidomide dose to ensure maximum plasma concentration of Thalidomide (CMax=3 hours) (Hui et al, Reproductive Toxicology, 2014). The uteri were removed, the implantation sites were counted and mortality and resorptions noted during embryo dissection. GD8 embryos were not dissected and were fixed in situ attached to the placental site and uterine wall. The entire implantation site was processed, embedded in paraffin and sectioned at 4 microns for immunohistochemistry. GD 9-12 embryos were collected with fetal membranes, fixed in 10% Neutral Buffered Formalin for 24 hours and transferred to 70% Ethanol. After fixation fetal membranes were removed and embryos processed, embedded in paraffin and sectioned at 4 microns for immunohistochemistry and in situ hybridization procedures.

Rabbit embryos were stained for SALL4, and mouse testis were stained for SALL4 and ZFP91. Immunohistochemistry (IHC) was performed on the Bond-III automated slide stainer (Leica Microsystems, Buffalo Grove, Ill.) using the Bond Polymer Refine Detection system (Leica Microsystems, DS9800). Formalin fixed paraffin embedded (FFPE) tissues were sectioned at four micron thick and deparaffinized on the Bond-Max instrument. Antigen retrieval was performed with Epitope Retrieval 2 (ER2, pH 9.0) for 20 min at 100° C. The slides were blocked for endogenous peroxidase activity with Peroxide Block for 5 minutes at room temperature. Sections were then incubated with the mouse monoclonal anti-SALL4 EE-30 antibody (Santa Cruz, sc-101147) at a 1:100 dilution for 60 min at room temperature, or with the rabbit monoclonal anti-ZFP91 antibody (Celgene custom clone 122-8-6) at 0.25 ug/ml. For mouse testis, primary antibodies were incubated for 15 min at room temperature, and Post-Primary and horseradish peroxidase (HRP) labeled Polymer were incubated at the instrument's default conditions. For rabbit tissue, SALL4 primary antibody was incubated for 60 min and the post-primary-HRP conjugated goat anti-mouse IgG (H+L) (Bethyl Laboratories, A90-116P) was incubated at a 1:200 dilution for 30 min at room temperature. For ZAFP91 staining on rabbit tissues, the following blocking steps were included: 1% T-X100 in TBS for 30 min, 2% normal goat serum plus 1% BSA in TBS for 30 min, goat anti-rabbit Fab fragments-unconjugated (JacksonImmunoResearch; cat#111-007-003) diluted 1/10 in TBS 1% NGS for 60 minutes, followed by primary ZFP91 antibody diluted in TBS with 2% NGS plus 1% BSA for 45 min incubation. A biotinylated secondary goat anti-rabbit Fab fragments (JacksonImmunoResearch; cat#111-067-003) was used at a 1/800 dilution in TBS with 1% NGS for 15 min followed by Streptavidin-HRP detection with Bond Intense R system. Antigen-antibody complexes was then visualized with hydrogen peroxide substrate and diaminobenzidine tetrahydrochloride (DAB) chromogen. Slides were counterstained with hematoxylin, dehydrated and coverslipped by the Tissue-Tek Film Automated Coverslipper.

In Situ Hybridization (ISH) for SALL4 RNA

A fully automated SALL4 ISH assay was performed on Leica BOND RX IHC & ISH stainer with the BOND Research Detection System (Leica, Cat. No. DS9455). Formalin fixed paraffin embedded (FFPE) rabbit embryos were sectioned at four micron thickness, baked at 60° C. for 1 hour and then deparaffinized in Dewax solution at 72° C. Antigen retrieval was performed in Epitope Retrieval 2 (ER2, pH 9.0) for 15 min at 95° C. Custom-designed rabbit SALL4 target probe was applied on the slides and incubated at 42° C. for 2 hours. SALL4 signal was then amplified with the RNAscope LS Multiplex Fluorescent Reagent Kit (ACD, Cat. No. 322800) using the BOND RX default ACD ISH protocol. SALL4 signal was detected with Opal TSA fluorophore 570 (PerkinElmer, Cat. No. FP1488001KT) at a 1:1500 dilution for a 30 min incubation. Slides were then coverslipped manually using ProLong Diamond Antifade Mountant with DAPI (Life Technology, Catalog No. P36966). After whole slide scan at 4× magnification was completed, 40× magnification images were acquired using Perkin Elmer Vectra 3.0 multispectral image platform.

Humanized Cereblon Mouse

C57Bl/6Ntac mice were used in this study and were maintained at Taconic under specific pathogen-free conditions.

Human CRBN expressing mice were generated via electroporation of C57Bl/6Ntac JM8 ES cells with the CRBN donor vector consisting of the human cDNA from exon 2 (Glu24), bGHpA and the neomycin selection cassette together with the XTN™ 2 TALEN, designed to target the neomycin cassette insertions site to enhance targeting (Transposogen). The vector was designed to enable CRBN to be driven by the endogenous murine promoter and the transcript terminated at the bGHpA, to disrupt the splicing of the mouse CRBN gene.

Sequencing of the PCR products from the clones confirmed targeting on both the 5' and 3' ends. Targeted clones were injected into blasts and the resulting chimeras bred to Cre recombinase deleter mice (Taconic) to achieve deletion of the neomycin resistance cassette. Colonies were then bred to homozygosity.

Determining Embryopathy in Humanized Cereblon Mouse

Thalidomide was administered to female HOM huCRBN mice by oral gavage at dose levels of 0 (1.0% [w/v] carboxymethylcellulose [1500-3000 cP] in RO deionized water), 100, 300, or 1000 mg/kg/day once daily on Gestation Day [GD] 6 through 15. On GD 15, blood samples were collected from the submandibular vein of mice assigned to study at 0.5, 1, 3, 6, and 24 hours postdose for bioanalytical and toxicokinetic evaluation. All animals survived to scheduled necropsy on GD 18. Mice were euthanized and examined, and a gross necropsy was performed. The ovaries and uterus were examined for number and distribution of corpora lutea, implantation sites, placentae (size, color, and shape), live and dead fetuses, and early and late resorptions. Fetuses were euthanized by an intraperitoneal injection of sodium pentobarbital (390 mg/mL). Fetuses were weighed and examined for sex and external abnormalities. Late resorptions were examined for external abnormalities and sex to the extent possible. The body weight of each fetus was recorded. Fetuses were individually identified with the study number, litter number and uterine distribution. Approximately one-half of the fetuses in each litter were examined for visceral abnormalities by using an adaptation of the sectioning technique of Wilson. Each fetus was fixed in Bouin's solution; sections were stored in alcohol. The remaining fetuses (approximately one-half of the fetuses in each litter) were examined for skeletal abnormalities after staining with alizarin red S. Following examination, skeletal preparations were retained in glycerin with thymol added as a preservative.

6.2 SALL4 is a Direct Substrate of Thalidomide and Cereblon-CRL4 In Vitro

SALL4 contains 7 zinc finger domains, 4 of which have a glycine at the same position as cereblon substrates Ikaros and Aiolos. In this example, four domains containing these 4 glycine-containing zinc fingers were tested for compound-dependent ubiquitination by cereblon-CRL4 in a fully purified, in vitro ubiquitination system (see FIG. 1). The first zinc finger domain encompasses amino acid residues 405-432, which has a sequence of TGERPFVCSVCGHRFTTKGNLKVHFHRH (SEQ ID NO: 3). The second zinc finger domain encompasses amino acid residues 589-616, which has a sequence of TGERPFQCKICGRAFSTKGNLKTHLGVH (SEQ ID NO: 4). The third zinc finger domain encompasses amino acid residues 865-892, which has a sequence of RQAKQHGCTRCGKNFSSASALQIHERTH (SEQ ID NO: 5). The fourth zinc finger domain encompasses amino acid residues 893-920, which has a sequence of TGEKPFVCNICGRAFTTKGNLKVHYMTH (SEQ ID NO: 6). Ikaros zinc finger domain (amino acid residues 140-168) was used as a control, which has a sequence of (SEQ ID NO: 7)
TGERPFQCNQCGASFTQKGNLLRHIKLHS.

More specifically, individual zinc finger domains of SALL4 were expressed in *E. coli* and purified via an MBP tag. Purified zinc fingers were then tested in an in vitro ubiquitination assay for cereblon binding and ubiquitination. Purified zinc fingers were incubated with purified cereblon-CRL4 ubiquitin ligase complex and purified ubiquitination cascade components Uba1, UbcH5a, UbcH5b, ATP, and ubiquitin. Ubiquitination was observed only in the presence of cereblon modifying compound (thalidomide, "thal") and not DMSO alone.

As shown in FIG. 1A, one zinc finger domain, amino acids 405 to 432, was ubiquitinated in a thalidomide-dependent manner quite strongly, to a degree similar as Ikaros. In vitro ubiquitination in a purified system demonstrates that the SALL4 protein can interact directly with thalidomide-bound cereblon for ubiquitination, and that zinc finger a.a. 405-432 (SEQ ID NO: 3) is the main driver of SALL4 binding to cereblon.

In a separate experiment, the SALL4 protein is further analyzed for the presence of the structural feature that has been shown to mediate the binding of known neosubstrates to cereblon, a beta-hairpin motif containing a glycine at a key position. Ikaros and Aiolos harbor this motif within a zinc finger domain. The 7 zinc finger domains of SALL4 analyzed in this experiment are shown in FIG. 1B. 4 of them contain a glycine at the position necessary to mediate cereblon binding (see FIG. 1B). The human version of these four individual zinc fingers were expressed and purified for testing in our in vitro cereblon-CRL4 ubiquitination assay (see FIG. 1C). One zinc finger domain (ZF2, amino acids 410-432 (SEQ ID NO: 11)) was robustly ubiquitinated in a thalidomide-dependent manner, and a second zinc finger domain (ZF4, amino acids 594-616) was also ubiquitinated in the presence of thalidomide, but more weakly. ZF2 was ubiquitinated to a similar degree as the Ikaros and ZFP91 zinc finger domains which have been shown to bind cereblon (see FIG. 1D). The existence of preferred zinc finger domains is highly reminiscent of the cereblon substrates Ikaros and Aiolos, where a single zinc finger motif mediates cereblon recruitment and degradation.

Additional experiments were performed to test whether the ubiquitination of these zinc fingers is dependent upon the glycine residue (G416 in ZF2 and G600 in ZF4), as has been established for other neosubstrates (see FIG. 1C and FIG. 1D). Ubiquitination of both zinc fingers was significantly reduced upon mutation of the glycine to alanine, consistent with the abrogated ubiquitination observed upon mutation of G151 to alanine in Ikaros and G406 to alanine in ZFP91 (see FIG. 1D) and indicating that these SALL4 zinc fingers bind cereblon using the glycine-containing beta-hairpin motif. Thus these ubiquitination experiments in a purified system demonstrate that SALL4 zinc fingers can interact directly with thalidomide-bound cereblon for ubiquitination, that ZF2 (amino acids 410-432) is the most significant cereblon interacting zinc finger, and that these zinc fingers appear to bind through the glycine-containing beta hairpin motif.

To explore the role of SALL4 ubiquitination in mediating thalidomide-induced teratogenicity, we next examined whether sequence differences could explain the differential sensitivity to thalidomide-induced teratogenicity between rabbits and mice. Mouse cereblon contains two amino acid variations around the thalidomide binding pocket that have been previously shown to disrupt cereblon neosubstrate binding, while rabbit cereblon does not contain these mutations, and its cereblon is 100% conserved with human cereblon in the area surrounding the neosubstrate binding site (see FIGS. 1E and 1G). An alignment of human SALL4 with mouse and rabbit orthologs indicates that while ZF2 is 100% conserved between human and rabbit, there are sequence variations in the mouse (see FIGS. 1F and 1G).

We then tested whether the rabbit and mouse SALL4 zinc fingers could be ubiquitinated by rabbit and mouse cereblon, respectively, upon thalidomide treatment. As shown in FIG. 1C, the rabbit zinc finger amino acids 357-385 (orthologous to human ZF2) could be ubiquitinated by rabbit cereblon in a thalidomide-dependent manner, with an efficiency comparable to the human proteins. In contrast, the mouse SALL4 zinc finger amino acids 410-438 (orthologous to human ZF2) could not be ubiquitinated by mouse cereblon. Given the known mutations in mouse cereblon that disrupt substrate binding, we then tested whether human cereblon could recognize the mouse SALL4. Human cereblon was found to be not able to ubiquitinate the mouse SALL4 zinc finger, demonstrating that the mutations in mouse SALL4 are detrimental to cereblon binding and thus SALL4 degradation will be impaired in both WT and human cereblon (huCRBN) transgenic mice. Indeed, when all 4 mouse SALL4 zinc fingers that harbor the glycine-containing beta-hairpin motif were tested, none of them were efficiently ubiquitinated by either mouse cereblon or human cereblon (see FIG. 1H).

6.3 SALL4 is a Direct Substrate of Thalidomide and Cereblon-CRL4 In Vivo and the Binding of SALL4 to Cereblon and Degradation of SALL4 Depend on Residue G416 of SALL4

Given the direct binding of SALL4 to cereblon and ubiquitination of SALL4 shown in the in vitro analysis, this example further tested the binding and ubiquitination in cells. Ubiquitination and proteasomal degradation of full length SALL4 in human tissue culture cells was analyzed.

Cells stably expressing full length human SALL4 were treated with thalidomide, lenalidomide, or pomalidomide in the presence or absence of cereblon. More specifically, a Lenti-x 293 cell line with CRISPR-cas9 cereblon knock-out and stable expression of HA-tagged SALL4 or SALL4 mutants was transfected with either GST-cereblon or empty vector. Cells were then treated with thalidomide (THAL), lenalidomide (LEN), or pomalidomide (POM) to monitor the compound-dependent degradation of SALL4. ZFP91 was monitored as a control compound-dependent cereblon substrate that exhibited compound-dependent degradation in all cell lines expressing cereblon. Actin was used as a loading control.

A compound-dependent reduction in SALL4 protein levels was observed and was found to be dependent upon cereblon expression (see FIG. 2). SALL4 that had been mutated to alanine at either G416 (the glycine present in the zinc finger at a.a. 405-432) or G600 (the glycine present in the zinc finger at a.a. 589-616) was then monitored for compound-dependent degradation. Mutation of G416A was sufficient to stabilize SALL4, preventing compound-induced SALL4 degradation, while mutation of G600A was not sufficient to stabilize SALL4, consistent with the zinc finger at a.a. 405-432 being the main driver of cereblon binding and compound-dependent ubiquitination in cells.

Binding of full length SALL4 to cereblon in cells was then tested by co-immunoprecipitation (see FIG. 3). HA-tagged WT, G416A, or G600A SALL4 was immunoprecipitated from cells, and the level of co-purifying cereblon was assessed by western blot. Briefly, a Lenti-x 293 cell line with a CRISPR-cas9 knock-out of cereblon and stable expression of HA-tagged SALL4 or SALL4 mutants was transfected with either GST-cereblon or empty vector. Cells were then treated with thalidomide (THAL), lenalidomide (LEN), or pomalidomide (POM), and SALL4 was pulled down using anti-HA beads. The amount of co-purifying GST-cereblon was then assessed by western blot. WT SALL4 and G600A SALL4 both showed strong, compound-dependent binding to cereblon, while the G416A mutant SALL4 disrupted the binding significantly, confirming that the SALL4 zinc finger at a.a. 405-432 is the main driver of SALL4 binding to cereblon.

6.4 Degradation of SALL4 Depends on the Compound Treatment

The compound-dependent degradation of endogenous SALL4 was then confirmed (see FIG. 4). Cultured NCCIT, NETRA-2 cl.D1 and AN3-CA cancer cell lines were treated with thalidomide, lenalidomide, or pomalidomide at the indicated concentration for 16 hours before cell samples were analyzed by western blot with an anti-SALL4 antibody (EE-30, Santa Cruz). Both a short exposure (S.E.) and a long exposure (L.E.) of the anti-SALL4 western blot are shown for comparison, along with an anti-cereblon blot confirming the presence of cereblon, and an anti-actin loading control.

Endogenous SALL4 can be observed by western blot in these cell lines, and drug-dependent degradation was monitored after a 16 hour treatment with either thalidomide, lenalidomide, or pomalidomide. Significant compound-dependent degradation of endogenous SALL4 was observed.

6.5 In Vivo Degradation of SALL4

Thalidomide dependent downregulation of SALL4 was also observed in rabbits in vivo. Rabbits have previously been demonstrated to be a sensitive species to thalidomide-induced teratogenicity. In this example, adult male rabbits were treated with 30 or 150 mg/kg thalidomide. Testis were dissected and subsequently examined by immunohistochemistry for SALL4 expression levels, and the result is shown in FIG. 5.

In a separate experiment, pregnant rabbits were treated with thalidomide at 180 mg/kg. Embryos were subsequently probed for SALL4 levels by immunohistochemistry, and the result is shown in FIG. 6.

More specifically, adult female New Zealand white rabbits between 5 and 8 months of age were time mated for embryo collection at Gestation Days (GD) 8, 9, 10, 11 and 12 as shown in Table 1 below.

CRISPR-mediated gene editing completely blocked the downregulation of SALL4 induced by thalidomide in human iPS cells (FIG. 7A). The thalidomide-induced reduction in SALL4 protein levels was prevented by the proteasome inhibitor MG132 and the nedd8 activating enzyme inhibitor MLN4924 (which leads to the inactivation of all CRLs), indicating that reduction in SALL4 protein levels occurs through ubiquitin-mediated proteasomal degradation (FIG. 7B). To rule out any transcriptional effect on SALL4 levels, we confirmed that SALL4 mRNA levels were not reduced by thalidomide treatment (FIG. 7E), and are instead increased, presumably owing to homeostatic regulation upon protein depletion as reported for the neosubstrate

TABLE 1

Implantations Sites in Thalidomide Treated Rabbits

| | Control | | | | Thal | | | |
|---|---|---|---|---|---|---|---|---|
| Age | Sites/Rabbit | Total Sites | Resorbed | Dead | Sites/Rabbit | Total Sites | Resorbed | Dead |
| GD8 | 6, 8, 10, 10 | 34 | 0 | 0 | 9, 9, 8, 7, 8 | 41 | 0 | 0 |
| GD9 | 6, 6, 9, 8 | 29 | 0 | 0 | 8, 11, 12, 10, 11 (1R) | 52 | 1 (1.92%) | 0 |
| GD10 | 4, 6, 10, 8 | 28 | 0 | 0 | 9, 12, 0, 8 (1D), 9 | 38 | 0 | 1 (0.03%) |
| GD11 | 9, 9, 9, 11 | 38 | 0 | 0 | 9, 8 (1R), 9 (1R, 1D), 9 (1D), 2 | 37 | 2 (5.41%) | 2 (5.41%) |
| GD12 | 11, 6, 8, 5 | 30 | 0 | 0 | 9 (2D), 9 (4D), 8 (2R), 9 (4D), 8 (1R, 1D) | 43 | 3 (6.98%) | 11 (25.58%) |

R = Resorbed;
D = Dead.

SALL4 immunohistochemistry was performed on whole sections of uterus containing GD8 embryos and on sagittal sections of GD9-12 untreated rabbit embryos and revealed SALL4 protein expression in all germ layers, with a distinct pattern of distribution (see FIG. 6). Nuclear SALL4 was noted in fetal membranes on GD8 but not in the placenta, endometrium or uterine wall. In GD9-12 embryos, SALL4 was similarly distributed with high levels observed in embryonic structures that are frequently affected in thalidomide teratogenicity studies. Highest SALL4 levels were observed in the neural tube and optic vesicles (ectoderm), limb buds, and mesonephron (mesoderm) and liver and lung bud (endoderm) (see FIG. 6). SALL4 levels were overall high on GD9, 10 and 11 and started to drop on GD12.

In thalidomide treated embryos, there was a significant decrease in SALL4 levels which was most pronounced on GD12 (see FIG. 6). Gross abnormalities in thalidomide treated embryos were observed from GD9 onwards indicating adequate thalidomide exposure in embryos across the susceptible gestation period. Most common findings included hemorrhage in the placenta, fetal membranes and in the abdominal region of embryos near the liver and lung buds, misshapen head, dilated optic vesicles, dilated and folded neural tubes, shortened limb buds and twisted tails. Thus, SALL4 protein levels are reduced by thalidomide in the relevant tissues during fetal development in an organism exhibiting thalidomide-induced teratogenicity Therefore, treatment with thalidomide was demonstrated to cause a dose-dependent decrease in SALL4 levels in the testis of male rabbits (see FIG. 5), and in rabbit embryos (see FIG. 6).

6.6 SALL4 is Degraded in Human iPS Cells in a Cereblon- and Proteasome-Dependent Manner Thalidomide induced degradation of endogenous SALL4 protein was also observed in human iPS cells. SALL4 levels were reduced upon exposure to thalidomide in a dose dependent fashion, and the knockout of cereblon via CRISPR-mediated gene editing completely blocked the downregulation of SALL4 induced by thalidomide in human iPS cells (FIG. 7A). The thalidomide-induced reduction in SALL4 protein levels was prevented by the proteasome inhibitor MG132 and the nedd8 activating enzyme inhibitor MLN4924 (which leads to the inactivation of all CRLs), indicating that reduction in SALL4 protein levels occurs through ubiquitin-mediated proteasomal degradation (FIG. 7B). To rule out any transcriptional effect on SALL4 levels, we confirmed that SALL4 mRNA levels were not reduced by thalidomide treatment (FIG. 7E), and are instead increased, presumably owing to homeostatic regulation upon protein depletion as reported for the neosubstrate GSPT1. To examine if the glycine containing degron in ZF2, identified as the most efficient substrate by in vitro ubiquitination, was responsible for the depletion of SALL4 protein in cells, the degradation of SALL4 wild-type, G416A, and G600A mutant proteins ectopically expressed in HEK 293 cells treated with thalidomide were tested (see FIG. 7C). Consistent with the in vitro results, the G416A mutation blocked the thalidomide dependent degradation of SALL4, while G600A had no effect on SALL4 degradation, confirming that ZF2 is the main zinc finger mediating cereblon binding and ubiquitination of SALL4. Similarly, the ability of wild-type, G416A, and G600A mutant proteins to bind cereblon was tested by co-immunoprecipitation (co-IP) (see FIG. 7D). Wild-type and G600A mutant SALL4 were able to bind cereblon, while the G416A mutation disrupted cereblon binding in cells. Taken together, these results indicate that the SALL4 protein is recruited to the CRL4-CRBN E3 ligase in a manner consistent with the other neosubstrates, and the 'G-motif' degron is located in zinc finger 2 around the critical residue G416.

6.7 SALL4 is Degraded in Rabbit Testis but not in huCRBN Mouse Testis

This example further tests and compares the degradation of SALL4 by thalidomide in vivo. SALL4 is expressed during fetal development, but expression remains in a limited number of adult tissues such as stem cells found in the testis. As a positive control, we wanted to compare SALL4 downregulation to that of a known cereblon neosubstrate. Thalidomide is only moderately active in triggering the degradation of Ikaros, and does not trigger the degradation of CK1α (data not shown here). We therefore sought a cereblon neosubstrate that was sensitive to thalidomide, and which also has broader tissue distribution than Ikaros to enable direct comparison by immunohistochemistry. As described above, ZFP91 was confirmed to be a direct substrate of CRL4-CRBN in the in vitro ubiquitination analysis.

Therefore, adult male rabbits and mice were tested and looked for changes in SALL4 and ZFP91 expression in the testis by immunohistochemistry. In rabbits and mice, SALL4 is highly expressed in the nucleus of a subset of cells located along the basal-most layer of the seminiferous tubules with morphologic features of spermatogonia. In thalidomide-treated rabbits there is a dose-dependent reduction of SALL4 protein levels in the testis with a marked decrease noted at 150 mg/kg/day (see FIG. 8, left panel). The ZFP91 degron is conserved between rabbits and human, and ZFP91 is correspondingly depleted in the treated rabbits (see FIG. 8, left panel). In situ hybridization showed that SALL4 mRNA levels were not altered upon thalidomide treatment, consistent with a degradation mechanism (see FIG. 9).

Mice are known to exhibit species-specific amino acid differences in cereblon that block neosubstrate recruitment and degradation, and have been shown to be resistant to the teratogenic effects of thalidomide. Upon treatment with thalidomide, WT mice exhibited no depletion of SALL4 or ZFP91 (see FIG. 8, middle panel). With the aim of conferring sensitivity to cereblon modulators we constructed a transgenic mouse engineered to express human cereblon (see FIG. 10). The sequence of ZFP91 is conserved between humans and mice in the region around the glycine containing neosubstrate degron, and accordingly ZFP91 is robustly downregulated in the huCRBN mice (see FIG. 8, right panel). In contrast, SALL4 protein levels remain unchanged in the testis after treatment with up to 1000 mg/kg of thalidomide for 7 days (see FIG. 8, right panel). These findings are consistent with the in vitro ubiquitination data which demonstrated that differences in ubiquitination rates can be explained by differences in SALL4 protein sequence between mice and rabbit.

6.8 Human Cereblon Transgenic Mice do not Exhibit Thalidomide Teratogenicity Knowing that human cereblon would cause the degradation of conserved neosubstrate proteins such as ZFP91 in mice, but not SALL4 due to the sequence differences in the mouse SALL4 protein (see Section 6.7), the teratogenic effects of thalidomide on the human transgenic mouse (huCRBN) are characterized in this example. Oral administration of thalidomide to time-mated homozygous huCRBN mice (10/group), at dosages of 0 (control), 100, 300 and 1000 mg/kg/day, during the period of major organogenesis (gestation days 6-15) did not result in any developmental abnormalities in the fetuses. There were 7, 9, 7 and 8 live fetuses in the control, 100, 300 and 1000 mg/kg/day groups, respectively. During the study the pharmacokinetics was assessed to ensure that thalidomide exposure levels were sufficient, and the corresponding mean plasma exposures (areas under the curve) in the drug-treated groups were 35,100, 78,600 and 143,000 ng·hr/mL. Fetuses were subsequently examined for manifestations of developmental abnormalities, and none were reported, a comparison of skeletal preparations from thalidomide treated and untreated huCRBN mice are shown in FIG. 11.

These results evidence that SALL4 is a direct, compound-dependent substrate of cereblon-CRL4 ubiquitination. Loss of SALL4 during development is known to cause limb malformations in Okihiro, IVIC, Holt-Oram, and Acrorenal-ocular syndromes. Thus, the present results indicate that SALL4 downregulation is a major driver of the teratogenic effects of certain compound treatment, e.g., thalidomide. Therefore, SALL4 can be used to determine the toxicity of cereblon modulating compounds, thereby allowing the screening and selection of compounds with reduced risk of reproductive toxicities. The presence of SALL4 or its mutants can also be used to select patients for treatment with cereblon modulating compounds.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed is:

1. A method of screening a cereblon modifying compound, comprising:
   (a) obtaining a sample containing Sal-like protein 4 (SALL4) and cereblon;
   (b) administering the cereblon modifying compound to the sample;
   (c) determining an interaction between the SALL4 and the cereblon after step (b), wherein the interaction between the SALL4 and the cereblon is determined by determining the interaction between amino acid residues 405-432 of the SALL4 protein (SEQ ID NO: 3) and the cereblon or by determining the interaction between amino acid residues 410-432 of the SALL4 protein (SEQ ID NO: 11) and the cereblon; and
   (d) selecting the cereblon modifying compound that does not induce the interaction between the SALL4 and the cereblon as determined in step (c).

2. The method of claim 1, further comprising
   (i) determining a first protein level of SALL4 in the sample prior to the administration of the cereblon modifying compound;
   (ii) determining a second protein level of SALL4 in the sample after the administration of the cereblon modifying compound;
   (iii) comparing the first protein level and the second protein level of SALL4 to determine if the cereblon modifying compound induces degradation of SALL4; and
   (iv) selecting the cereblon modifying compound that does not induce the degradation of SALL4 as determined in step (iii).

* * * * *